US010323084B2

(12) United States Patent
Hillen et al.

(10) Patent No.: US 10,323,084 B2
(45) Date of Patent: Jun. 18, 2019

(54) MONOCLONAL ANTIBODIES AGAINST AMYLOID BETA PROTEIN AND USES THEREOF

(71) Applicants: ABBVIE INC., North Chicago, IL (US); ABBVIE DEUTSCHLAND GMBH & CO KG, Wiesbaden (DE)

(72) Inventors: Heinz Hillen, Hassloch (DE); Stefan Barghorn, Mannheim (DE); Boris Labkovsky, Wales, MA (US); Ulrich Ebert, Mannheim (DE); Andreas Striebinger, Speyer (DE); Patrick Keller, Darmstadt (DE)

(73) Assignees: ABBVIE INC., North Chicago, IL (US); ABBVIE DEUTSCHLAND GMBH & CO. KG, Wiesbaden (DE)

(*) Notice: Subject to any disclaimer, the term of this patent is extended or adjusted under 35 U.S.C. 154(b) by 0 days.

(21) Appl. No.: 15/662,224

(22) Filed: Jul. 27, 2017

(65) Prior Publication Data
US 2018/0066044 A1   Mar. 8, 2018

Related U.S. Application Data

(62) Division of application No. 13/188,034, filed on Jul. 21, 2011, which is a division of application No. 11/574,847, filed as application No. PCT/US2006/046148 on Nov. 30, 2006, now Pat. No. 8,497,072.

(60) Provisional application No. 60/778,950, filed on Mar. 3, 2006, provisional application No. 60/740,866, filed on Nov. 30, 2005.

(51) Int. Cl.
*A61K 39/395*   (2006.01)
*C07K 16/18*    (2006.01)
*G01N 33/68*    (2006.01)
*G01N 33/577*   (2006.01)
*A61K 39/00*    (2006.01)

(52) U.S. Cl.
CPC .......... *C07K 16/18* (2013.01); *A61K 39/3955* (2013.01); *G01N 33/577* (2013.01); *G01N 33/6896* (2013.01); *A61K 2039/505* (2013.01); *C07K 2317/14* (2013.01); *C07K 2317/20* (2013.01); *C07K 2317/21* (2013.01); *C07K 2317/24* (2013.01); *C07K 2317/56* (2013.01); *C07K 2317/565* (2013.01); *C07K 2317/92* (2013.01); *G01N 2333/4709* (2013.01); *G01N 2500/20* (2013.01); *G01N 2800/2821* (2013.01)

(58) Field of Classification Search
CPC .......................... C07K 16/18; C07K 2317/92; C07K 2317/56; C07K 2317/565; C07K 2317/24; C07K 2317/21; C07K 2317/20; C07K 2317/14; C07K 2317/34; A61K 39/3955
See application file for complete search history.

(56) References Cited

U.S. PATENT DOCUMENTS

| | | |
|---|---|---|
| 4,399,216 A | 8/1983 | Axel et al. |
| 4,510,245 A | 4/1985 | Cousens et al. |
| 4,526,039 A | 7/1985 | Ceccon et al. |
| 4,582,788 A | 4/1986 | Erlich |
| 4,634,665 A | 1/1987 | Axel et al. |
| 4,666,829 A | 5/1987 | Glenner et al. |
| 4,683,194 A | 7/1987 | Saike et al. |
| 4,683,202 A | 7/1987 | Mullis |
| 4,757,506 A | 7/1988 | Heichler |
| 4,816,397 A | 3/1989 | Boss et al. |
| 4,816,567 A | 3/1989 | Cabilly et al. |
| 4,880,078 A | 11/1989 | Inoue et al. |
| 4,946,778 A | 8/1990 | Ladner et al. |
| 4,968,615 A | 11/1990 | Koszinowski et al. |
| 4,980,286 A | 12/1990 | Morgan et al. |
| 5,107,065 A | 4/1992 | Shewmaker et al. |
| 5,128,326 A | 7/1992 | Balazs et al. |
| 5,134,062 A | 7/1992 | Blass |
| 5,168,062 A | 12/1992 | Stinski |
| 5,179,017 A | 1/1993 | Axel et al. |
| 5,218,100 A | 6/1993 | Muller-Hill et al. |
| 5,223,409 A | 6/1993 | Ladner et al. |
| 5,225,539 A | 7/1993 | Winter |
| 5,231,000 A | 7/1993 | Majocha et al. |
| 5,231,020 A | 7/1993 | Jorgensen et al. |
| 5,231,170 A | 7/1993 | Averback |
| 5,234,814 A | 8/1993 | Card et al. |
| 5,258,498 A | 11/1993 | Huston et al. |
| 5,262,332 A | 11/1993 | Selkoe |
| 5,290,540 A | 3/1994 | Prince et al. |
| 5,403,484 A | 4/1995 | Ladner et al. |
| 5,427,908 A | 6/1995 | Dower et al. |
| 5,441,870 A | 8/1995 | Seubert et al. |
| 5,455,169 A | 10/1995 | Mullan |

(Continued)

FOREIGN PATENT DOCUMENTS

| | | |
|---|---|---|
| AU | 2007200047 A1 | 1/2007 |
| CA | 2514582 A1 | 8/2004 |

(Continued)

OTHER PUBLICATIONS

Acha-Orbea et al. "Anti-T-Cell Receptor V Beta Antibodies in Autoimmunity," *Immunol. Ser.* 59:193-202, (1993).

(Continued)

*Primary Examiner* — Kimberly Ballard
(74) *Attorney, Agent, or Firm* — Morrison & Foerster LLP

(57) ABSTRACT

The subject invention relates to monoclonal antibodies (e.g., 8F5 and 8C5) that may be used, for example, in the prevention, treatment and diagnosis of Alzheimer's Disease or other neurodegenerative disorders.

16 Claims, 14 Drawing Sheets

Specification includes a Sequence Listing.

(56) References Cited

U.S. PATENT DOCUMENTS

| | | |
|---|---|---|
| 5,516,637 A | 5/1996 | Huang et al. |
| 5,530,101 A | 6/1996 | Queen et al. |
| 5,538,845 A | 7/1996 | Knops et al. |
| 5,545,806 A | 8/1996 | Lonberg et al. |
| 5,565,332 A | 10/1996 | Hongenboom et al. |
| 5,565,352 A | 10/1996 | Hochstrasser et al. |
| 5,567,720 A | 10/1996 | Averback |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,593,846 A | 1/1997 | Schenk et al. |
| 5,605,811 A | 2/1997 | Seubert et al. |
| 5,624,821 A | 4/1997 | Winter et al. |
| 5,625,126 A | 4/1997 | Lonberg et al. |
| 5,627,052 A | 5/1997 | Schrader |
| 5,633,425 A | 5/1997 | Lonberg et al. |
| 5,648,260 A | 7/1997 | Winter et al. |
| 5,658,727 A | 8/1997 | Barbas et al. |
| 5,661,016 A | 8/1997 | Lonberg et al. |
| 5,665,355 A | 9/1997 | Primi |
| 5,679,377 A | 10/1997 | Bernstein et al. |
| 5,679,531 A | 10/1997 | Koenig et al. |
| 5,693,753 A | 12/1997 | Koenig et al. |
| 5,693,762 A | 12/1997 | Queen et al. |
| 5,698,426 A | 12/1997 | Huse |
| 5,705,330 A | 1/1998 | Shah et al. |
| 5,705,401 A | 1/1998 | Masters et al. |
| 5,714,350 A | 2/1998 | Co et al. |
| 5,714,352 A | 2/1998 | Jakobovits |
| 5,721,130 A | 2/1998 | Seubert et al. |
| 5,723,323 A | 3/1998 | Kauffman et al. |
| 5,733,743 A | 3/1998 | Johnson et al. |
| 5,750,349 A | 5/1998 | Suzuki et al. |
| 5,750,753 A | 5/1998 | Kimae et al. |
| 5,763,192 A | 6/1998 | Kauffman et al. |
| 5,766,846 A | 6/1998 | Schlossmacher et al. |
| 5,766,886 A | 6/1998 | Studnicka et al. |
| 5,770,429 A | 6/1998 | Lonberg et al. |
| 5,780,225 A | 7/1998 | Wigler et al. |
| 5,786,180 A | 7/1998 | Konig et al. |
| 5,807,715 A | 9/1998 | Morrison et al. |
| 5,814,318 A | 9/1998 | Lonberg et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,837,500 A | 11/1998 | Ladner et al. |
| 5,855,913 A | 1/1999 | Hanes et al. |
| 5,874,064 A | 2/1999 | Edwards et al. |
| 5,877,397 A | 3/1999 | Lonberg et al. |
| 5,879,909 A | 3/1999 | Perl |
| 5,882,644 A | 3/1999 | Chang et al. |
| 5,885,793 A | 3/1999 | Griffiths et al. |
| 5,912,015 A | 6/1999 | Bernstein et al. |
| 5,912,120 A | 6/1999 | Goldstein et al. |
| 5,916,597 A | 6/1999 | Lee et al. |
| 5,916,771 A | 6/1999 | Hort et al. |
| 5,934,272 A | 8/1999 | Lloyd et al. |
| 5,939,598 A | 8/1999 | Kucherlapati et al. |
| 5,955,285 A | 9/1999 | Averback |
| 5,955,317 A | 9/1999 | Suzuki et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,615 A | 11/1999 | Jakobovits et al. |
| 5,989,463 A | 11/1999 | Tracy et al. |
| 5,998,209 A | 12/1999 | Jakobovits et al. |
| 6,010,913 A | 1/2000 | Vandermeeren et al. |
| 6,018,024 A | 1/2000 | Seubert et al. |
| 6,019,968 A | 2/2000 | Platz et al. |
| 6,075,181 A | 6/2000 | Kucherlapati et al. |
| 6,091,001 A | 7/2000 | Jakobovits et al. |
| 6,114,133 A | 9/2000 | Seubert et al. |
| 6,114,598 A | 9/2000 | Kucherlapati et al. |
| 6,130,364 A | 10/2000 | Jakobovits et al. |
| 6,180,370 B1 | 1/2001 | Queen et al. |
| 6,204,023 B1 | 3/2001 | Robinson et al. |
| 6,218,506 B1 | 4/2001 | Finch et al. |
| 6,284,221 B1 | 9/2001 | Schenk et al. |
| 6,287,793 B1 | 9/2001 | Schenk et al. |
| 6,294,171 B2 | 9/2001 | McMichael |
| 6,309,892 B1 | 10/2001 | Averback |
| 6,316,456 B1 | 11/2001 | Meijer et al. |
| 6,323,218 B1 | 11/2001 | Bush et al. |
| 6,333,034 B1 | 12/2001 | Gupta-Bansal et al. |
| 6,350,861 B1 | 2/2002 | Co et al. |
| 6,387,674 B1 | 5/2002 | Trasciatti et al. |
| 6,582,945 B1 | 6/2003 | Raso |
| 6,610,493 B1 | 8/2003 | Citron et al. |
| 6,660,843 B1 | 12/2003 | Feige et al. |
| 6,664,442 B2 | 12/2003 | McConlogue et al. |
| 6,699,658 B1 | 3/2004 | Wittrup et al. |
| 6,710,226 B1 | 3/2004 | Schenk |
| 6,713,450 B2 | 3/2004 | Frangione et al. |
| 6,743,427 B1 | 6/2004 | Schenk |
| 6,750,324 B1 | 6/2004 | Schenk et al. |
| 6,761,888 B1 | 7/2004 | Schenk et al. |
| 6,785,434 B2 | 8/2004 | Castoldi et al. |
| 6,787,138 B1 | 9/2004 | Schenk |
| 6,787,139 B1 | 9/2004 | Schenk |
| 6,787,140 B1 | 9/2004 | Schenk |
| 6,787,143 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk |
| 6,815,175 B2 | 11/2004 | Weksler et al. |
| 6,849,416 B2 | 2/2005 | Wiltfang et al. |
| 6,866,849 B2 | 3/2005 | Schenk |
| 6,866,850 B2 | 3/2005 | Schenk |
| 6,872,554 B2 | 3/2005 | Raso |
| 6,875,434 B1 | 4/2005 | Schenk |
| 6,886,154 B2 | 4/2005 | Okuyama |
| 6,905,686 B1 | 6/2005 | Schenk |
| 6,913,745 B1 | 7/2005 | Schenk |
| 6,919,075 B1 | 7/2005 | Solomon et al. |
| 6,972,127 B2 | 12/2005 | Schenk |
| 6,982,084 B1 | 1/2006 | Schenk |
| 7,014,855 B2 | 3/2006 | Schenk |
| 7,022,500 B1 | 4/2006 | Queen et al. |
| 7,045,531 B1 | 5/2006 | Bush et al. |
| 7,060,270 B2 | 6/2006 | Nicolau et al. |
| 7,067,133 B2 | 6/2006 | Nicolau |
| 7,094,884 B2 | 8/2006 | Scholz et al. |
| 7,122,374 B1 | 10/2006 | Saido et al. |
| 7,135,181 B2 | 11/2006 | Jensen et al. |
| 7,169,389 B2 | 1/2007 | Di Padova et al. |
| 7,179,463 B2 | 2/2007 | Lannfelt et al. |
| 7,179,606 B2 | 2/2007 | Jackowski et al. |
| 7,179,892 B2 | 2/2007 | Basi et al. |
| 7,186,881 B2 | 3/2007 | Games et al. |
| 7,189,703 B2 | 3/2007 | Balin et al. |
| 7,189,819 B2 | 3/2007 | Basi et al. |
| 7,195,761 B2 | 3/2007 | Holtzman et al. |
| 7,195,881 B2 | 3/2007 | Geffard |
| 7,196,163 B2 | 3/2007 | Hazuda et al. |
| 7,226,730 B1 | 6/2007 | De La et al. |
| 7,238,488 B2 | 7/2007 | Maresh et al. |
| 7,238,788 B2 | 7/2007 | Lee |
| 7,247,301 B2 | 7/2007 | Van De Winkel et al. |
| 7,256,273 B2 | 8/2007 | Basi et al. |
| 7,270,818 B2 | 9/2007 | Averback |
| 7,279,165 B2 | 10/2007 | Bachmann et al. |
| 7,318,923 B2 | 1/2008 | Tsurushita et al. |
| 7,320,790 B2 | 1/2008 | Hinton et al. |
| 7,320,793 B2 | 1/2008 | Renner et al. |
| 7,335,491 B2 | 2/2008 | Drapeau et al. |
| 7,339,035 B2 | 3/2008 | Yanagisawa et al. |
| 7,342,091 B2 | 3/2008 | Kapurniotu et al. |
| 7,371,365 B2 | 5/2008 | Poduslo et al. |
| 7,375,190 B2 | 5/2008 | Cheng et al. |
| 7,413,884 B2 | 8/2008 | Raso |
| 7,427,342 B2 | 9/2008 | Barber |

(56) References Cited

U.S. PATENT DOCUMENTS

| | | |
|---|---|---|
| 7,432,363 B2 | 10/2008 | Horie et al. |
| 7,625,560 B2 | 12/2009 | Basi et al. |
| 7,741,448 B2 | 6/2010 | Yanagisawa et al. |
| 7,772,375 B2 | 8/2010 | Greferath et al. |
| 7,892,544 B2 | 2/2011 | Pfeifer et al. |
| 7,902,328 B2 | 3/2011 | Hillen et al. |
| 8,034,353 B2 | 10/2011 | Yano et al. |
| 8,263,558 B2 | 9/2012 | Holzman et al. |
| 8,318,707 B2 | 11/2012 | Timsit et al. |
| 8,398,981 B2 | 3/2013 | Iwatsubo et al. |
| 8,455,626 B2 | 6/2013 | Barghorn et al. |
| 8,497,072 B2 | 7/2013 | Hillen et al. |
| 8,691,224 B2 | 4/2014 | Barghorn et al. |
| 8,895,004 B2 | 11/2014 | Nimmrich et al. |
| 8,987,419 B2 | 3/2015 | Barghorn et al. |
| 9,062,101 B2 | 6/2015 | Barghorn et al. |
| 9,359,430 B2 | 6/2016 | Barghorn et al. |
| 9,394,360 B2 | 7/2016 | Barghorn et al. |
| 2001/0029293 A1 | 10/2001 | Gallatin et al. |
| 2002/0009445 A1 | 1/2002 | Du et al. |
| 2002/0015941 A1 | 2/2002 | Kim et al. |
| 2002/0086014 A1 | 7/2002 | Korman et al. |
| 2002/0086847 A1 | 7/2002 | Chain |
| 2002/0094335 A1 | 7/2002 | Chalifour et al. |
| 2002/0132758 A1 | 9/2002 | Shell et al. |
| 2002/0137134 A1 | 9/2002 | Gerngross |
| 2002/0162129 A1 | 10/2002 | Lannfelt et al. |
| 2002/0173552 A1 | 11/2002 | Cleland et al. |
| 2002/0182644 A1 | 12/2002 | Diamandis |
| 2002/0182660 A1 | 12/2002 | Fong |
| 2002/0188106 A1 | 12/2002 | Mandelkow et al. |
| 2002/0197258 A1 | 12/2002 | Ghanbari et al. |
| 2003/0065141 A1 | 4/2003 | Carter et al. |
| 2003/0068316 A1 | 4/2003 | Klein et al. |
| 2003/0073655 A1 | 4/2003 | Chain |
| 2003/0077278 A1 | 4/2003 | Gallatin et al. |
| 2003/0077757 A1 | 4/2003 | Andrews |
| 2003/0086938 A1 | 5/2003 | Jensen et al. |
| 2003/0100011 A1 | 5/2003 | Jackowski et al. |
| 2003/0100058 A1 | 5/2003 | Roschke et al. |
| 2003/0108551 A1 | 6/2003 | Nicolau et al. |
| 2003/0114510 A1 | 6/2003 | Roschke et al. |
| 2003/0147882 A1 | 8/2003 | Solomon et al. |
| 2003/0148356 A1 | 8/2003 | Cruts et al. |
| 2003/0157117 A1 | 8/2003 | Rasmussen et al. |
| 2003/0180722 A1 | 9/2003 | Godbole et al. |
| 2003/0185826 A1 | 10/2003 | Tobinick |
| 2003/0185827 A1 | 10/2003 | Rodriguez et al. |
| 2003/0186333 A1 | 10/2003 | Loring et al. |
| 2003/0186374 A1 | 10/2003 | Hufton et al. |
| 2003/0190689 A1 | 10/2003 | Crosby et al. |
| 2003/0194403 A1 | 10/2003 | Van De Winkel et al. |
| 2003/0195347 A1 | 10/2003 | Baker et al. |
| 2003/0228307 A1 | 12/2003 | Ramakrishnan et al. |
| 2003/0229907 A1 | 12/2003 | Hsaio et al. |
| 2003/0232758 A1 | 12/2003 | St. George-Hyslop et al. |
| 2004/0005307 A1 | 1/2004 | Findesi et al. |
| 2004/0013647 A1 | 1/2004 | Solomon et al. |
| 2004/0013680 A1 | 1/2004 | Bush et al. |
| 2004/0018590 A1 | 1/2004 | Gerngross et al. |
| 2004/0043418 A1 | 3/2004 | Holtzman et al. |
| 2004/0053371 A1 | 3/2004 | Maresh et al. |
| 2004/0058414 A1 | 3/2004 | Queen et al. |
| 2004/0081657 A1 | 4/2004 | Schenk |
| 2004/0116337 A1 | 6/2004 | Kapumiotu et al. |
| 2004/0127471 A1 | 7/2004 | Reisberg |
| 2004/0138296 A1 | 7/2004 | Robertson et al. |
| 2004/0142872 A1 | 7/2004 | Podusio et al. |
| 2004/0146512 A1 | 7/2004 | Rosenthal et al. |
| 2004/0157267 A1 | 8/2004 | Huang |
| 2004/0157779 A1 | 8/2004 | Schenk |
| 2004/0166119 A1 | 8/2004 | Schenk |
| 2004/0170641 A1 | 9/2004 | Schenk |
| 2004/0175394 A1 | 9/2004 | Schenk |
| 2004/0185039 A1 | 9/2004 | Kohler et al. |
| 2004/0191264 A1 | 9/2004 | Nielsen et al. |
| 2004/0192898 A1 | 9/2004 | Jia et al. |
| 2004/0213800 A1 | 10/2004 | Seubert et al. |
| 2004/0223912 A1 | 11/2004 | Montalto et al. |
| 2004/0223970 A1 | 11/2004 | Afar et al. |
| 2004/0228865 A1 | 11/2004 | Schenk |
| 2004/0241164 A1 | 12/2004 | Bales et al. |
| 2004/0242845 A1 | 12/2004 | Nicolau et al. |
| 2004/0248197 A1 | 12/2004 | Holtzman et al. |
| 2004/0265308 A1 | 12/2004 | Schenk |
| 2004/0265919 A1 | 12/2004 | Vanderstichele et al. |
| 2005/0009110 A1 | 1/2005 | Chang |
| 2005/0014821 A1 | 1/2005 | Tsai et al. |
| 2005/0019330 A1 | 1/2005 | Schenk |
| 2005/0019343 A1 | 1/2005 | Schenk |
| 2005/0031651 A1 | 2/2005 | Gervais et al. |
| 2005/0037026 A1 | 2/2005 | Schenk |
| 2005/0042664 A1 | 2/2005 | Wu et al. |
| 2005/0048584 A1 | 3/2005 | Lamping et al. |
| 2005/0053614 A1 | 3/2005 | Schenk |
| 2005/0057813 A1 | 3/2005 | Hasei et al. |
| 2005/0059591 A1 | 3/2005 | Schenk et al. |
| 2005/0059802 A1 | 3/2005 | Schenk et al. |
| 2005/0090439 A1 | 4/2005 | Chalifour et al. |
| 2005/0112543 A1 | 5/2005 | Bush et al. |
| 2005/0118651 A1 | 6/2005 | Basi et al. |
| 2005/0123544 A1 | 6/2005 | Schenk et al. |
| 2005/0124016 A1 | 6/2005 | LaDu et al. |
| 2005/0129691 A1 | 6/2005 | Gerlai |
| 2005/0129695 A1 | 6/2005 | Mercken et al. |
| 2005/0142131 A1 | 6/2005 | Hinton et al. |
| 2005/0142132 A1 | 6/2005 | Schenk et al. |
| 2005/0147613 A1 | 7/2005 | Raso |
| 2005/0153381 A1 | 7/2005 | Marusich et al. |
| 2005/0163744 A1 | 7/2005 | Rasmussen et al. |
| 2005/0163788 A1 | 7/2005 | Schenk |
| 2005/0169925 A1 | 8/2005 | Bardroff et al. |
| 2005/0175626 A1 | 8/2005 | Delacourte et al. |
| 2005/0181460 A1 | 8/2005 | Ohno et al. |
| 2005/0239808 A1 | 10/2005 | Schrader et al. |
| 2005/0249725 A1 | 11/2005 | Schenk et al. |
| 2005/0249727 A1 | 11/2005 | Schenk |
| 2005/0255122 A1 | 11/2005 | Schenk |
| 2005/0272025 A1 | 12/2005 | Suo et al. |
| 2006/0008458 A1 | 1/2006 | Solomon |
| 2006/0029603 A1 | 2/2006 | Ellis et al. |
| 2006/0029611 A1 | 2/2006 | Schenk |
| 2006/0034858 A1 | 2/2006 | Schenk |
| 2006/0039906 A1 | 2/2006 | Holtzman et al. |
| 2006/0057646 A1 | 3/2006 | Wiltfang et al. |
| 2006/0057701 A1 | 3/2006 | Rosenthal et al. |
| 2006/0057702 A1 | 3/2006 | Rosenthal et al. |
| 2006/0062786 A1 | 3/2006 | Salcedo et al. |
| 2006/0073149 A1 | 4/2006 | Bales et al. |
| 2006/0099211 A1 | 5/2006 | Monthe et al. |
| 2006/0104968 A1 | 5/2006 | Bookbinder et al. |
| 2006/0105394 A1 | 5/2006 | Pomara |
| 2006/0110388 A1 | 5/2006 | Davies et al. |
| 2006/0111301 A1 | 5/2006 | Mattner |
| 2006/0127954 A1 | 6/2006 | Mercken et al. |
| 2006/0141541 A1 | 6/2006 | McIntyre |
| 2006/0160161 A1 | 7/2006 | Pavliakova et al. |
| 2006/0165682 A1 | 7/2006 | Basi et al. |
| 2006/0166275 A1 | 7/2006 | Krafft et al. |
| 2006/0166311 A1 | 7/2006 | Okochi et al. |
| 2006/0188505 A1 | 8/2006 | Skurkovich et al. |
| 2006/0193850 A1 | 8/2006 | Warne et al. |
| 2006/0198851 A1 | 9/2006 | Basi et al. |
| 2006/0217536 A1 | 9/2006 | Matsumoto et al. |
| 2006/0162129 A1 | 10/2006 | Lannfelt et al. |
| 2006/0228349 A1 | 10/2006 | Acton et al. |
| 2006/0234947 A1 | 10/2006 | Gazit |
| 2006/0240007 A1 | 10/2006 | Sanders |
| 2006/0241038 A1 | 10/2006 | Watanabe et al. |
| 2006/0246075 A1 | 11/2006 | Mercken et al. |
| 2006/0257420 A1 | 11/2006 | Zimmerman |
| 2006/0257882 A1 | 11/2006 | Shimkets |
| 2006/0280733 A1 | 12/2006 | Kayed et al. |
| 2006/0292152 A1 | 12/2006 | Rosenthal et al. |

(56) References Cited

U.S. PATENT DOCUMENTS

| | | |
|---|---|---|
| 2007/0009931 A1 | 1/2007 | Kirsch |
| 2007/0010435 A1 | 1/2007 | Frangione et al. |
| 2007/0010657 A1 | 1/2007 | Klocke et al. |
| 2007/0015217 A1 | 1/2007 | Durham et al. |
| 2007/0015218 A1 | 1/2007 | Cao et al. |
| 2007/0021345 A1 | 1/2007 | Gazit |
| 2007/0031416 A1 | 2/2007 | Shoji et al. |
| 2007/0036789 A1 | 2/2007 | Chung et al. |
| 2007/0036794 A1 | 2/2007 | Devaux |
| 2007/0042424 A1 | 2/2007 | Ebinuma et al. |
| 2007/0048312 A1 | 3/2007 | Klein et al. |
| 2007/0054940 A1 | 3/2007 | Kondo |
| 2007/0071675 A1 | 3/2007 | Wu et al. |
| 2007/0072307 A1 | 3/2007 | Godavarti et al. |
| 2007/0081998 A1 | 4/2007 | Kinney et al. |
| 2007/0082350 A1 | 4/2007 | Landfield et al. |
| 2007/0086994 A1 | 4/2007 | Wallach et al. |
| 2007/0098721 A1 | 5/2007 | Hillen et al. |
| 2007/0105092 A1 | 5/2007 | Paul et al. |
| 2007/0110750 A1 | 5/2007 | Glabe et al. |
| 2007/0111252 A1 | 5/2007 | Suzuki et al. |
| 2007/0122405 A1 | 5/2007 | Roschke et al. |
| 2007/0128191 A1 | 6/2007 | Barrio |
| 2007/0134247 A9 | 6/2007 | Solomon |
| 2007/0135337 A2 | 6/2007 | Chalifour et al. |
| 2007/0140966 A1 | 6/2007 | Chang et al. |
| 2007/0148167 A1 | 6/2007 | Strohl |
| 2007/0160616 A1 | 7/2007 | Rosenthal et al. |
| 2007/0167522 A1 | 7/2007 | Imawaka et al. |
| 2007/0190046 A1 | 8/2007 | DeMaattos et al. |
| 2007/0196367 A1 | 8/2007 | Dinu |
| 2007/0213512 A1 | 9/2007 | Krafft et al. |
| 2007/0218069 A1 | 9/2007 | Gordon et al. |
| 2007/0218499 A1 | 9/2007 | Lambert et al. |
| 2007/0231331 A1 | 10/2007 | Dewji et al. |
| 2007/0248606 A1 | 10/2007 | Lannfelt et al. |
| 2007/0264276 A1 | 11/2007 | Chalifour et al. |
| 2007/0280953 A1 | 12/2007 | Rosenberg et al. |
| 2007/0292410 A1 | 12/2007 | Cashman et al. |
| 2007/0292895 A1 | 12/2007 | Shi et al. |
| 2008/0009467 A1 | 1/2008 | Henderson |
| 2008/0014194 A1 | 1/2008 | Schenk et al. |
| 2008/0014596 A1 | 1/2008 | Jerecic et al. |
| 2008/0025979 A1 | 1/2008 | Honjo et al. |
| 2008/0025988 A1 | 1/2008 | Yamaguchi et al. |
| 2008/0029911 A1 | 2/2008 | Jeon et al. |
| 2008/0044356 A1 | 2/2008 | Lesne et al. |
| 2008/0044406 A1 | 2/2008 | Johnson-Wood et al. |
| 2008/0051690 A1 | 2/2008 | Mattner et al. |
| 2008/0057053 A1 | 3/2008 | Stolen |
| 2008/0057593 A1 | 3/2008 | Vanderstichele et al. |
| 2008/0058276 A1 | 3/2008 | Lu et al. |
| 2008/0058330 A1 | 3/2008 | Paris et al. |
| 2008/0063636 A1 | 3/2008 | Mori et al. |
| 2008/0089885 A1 | 4/2008 | Smith et al. |
| 2008/0096818 A1 | 4/2008 | Schenk et al. |
| 2008/0102055 A1 | 5/2008 | Chiba et al. |
| 2008/0107601 A1 | 5/2008 | Lauwereys et al. |
| 2008/0107649 A1 | 5/2008 | Zurbriggen |
| 2008/0113444 A1 | 5/2008 | Pray |
| 2008/0131422 A1 | 6/2008 | Sugimura et al. |
| 2008/0199879 A1 | 8/2008 | Takayama et al. |
| 2008/0220449 A1 | 9/2008 | Vasan et al. |
| 2008/0292639 A1 | 11/2008 | Shen et al. |
| 2008/0299111 A1 | 12/2008 | Delacourte et al. |
| 2009/0004144 A1 | 1/2009 | Tabira et al. |
| 2009/0018084 A1 | 1/2009 | Krafft et al. |
| 2009/0023159 A1 | 1/2009 | Mendez |
| 2009/0035295 A1 | 2/2009 | Hillen |
| 2009/0074775 A1 | 3/2009 | Holtzman et al. |
| 2009/0155246 A1 | 6/2009 | Gellerfors et al. |
| 2009/0156471 A1 | 6/2009 | Gazit et al. |
| 2009/0162362 A1 | 6/2009 | Barrio |
| 2009/0162878 A1 | 6/2009 | Kim et al. |
| 2009/0175847 A1 | 7/2009 | Hillen |
| 2009/0191190 A1 | 7/2009 | Barghorn |
| 2009/0214515 A1 | 8/2009 | Holzman et al. |
| 2009/0232801 A1 | 9/2009 | Hillen et al. |
| 2009/0238831 A1 | 9/2009 | Hillen et al. |
| 2009/0291453 A1 | 11/2009 | Takayama |
| 2009/0304712 A1 | 12/2009 | Takeuchi et al. |
| 2010/0028333 A1 | 2/2010 | Getty et al. |
| 2010/0173828 A1 | 7/2010 | Hillen et al. |
| 2010/0209346 A1 | 8/2010 | Hillen et al. |
| 2011/0287005 A1 | 1/2011 | Hillen et al. |
| 2011/0092445 A1 | 4/2011 | Barghorn |
| 2011/0212109 A1 | 9/2011 | Barghorn |
| 2011/0256138 A1 | 10/2011 | Barghorn |
| 2012/0034166 A1 | 2/2012 | Hillen et al. |
| 2014/0127191 A1 | 5/2014 | Barghorn et al. |
| 2015/0071915 A1 | 3/2015 | Hillen et al. |
| 2015/0079096 A1 | 3/2015 | Nimmrich et al. |
| 2016/0000891 A1 | 1/2016 | Barghorn et al. |
| 2016/0159891 A1 | 6/2016 | Hillen et al. |

FOREIGN PATENT DOCUMENTS

| | | |
|---|---|---|
| CA | 2541522 A1 | 9/2007 |
| CN | 1396183 A | 2/2003 |
| CN | 1446581 A | 10/2003 |
| CN | 1673369 A | 9/2005 |
| CN | 1721437 A | 1/2006 |
| CN | 1803842 A | 7/2006 |
| CN | 101058608 A | 10/2007 |
| CN | 10184909 A | 12/2007 |
| CN | 101084909 A | 12/2007 |
| CN | 101152576 A | 4/2008 |
| DE | 19902550 A1 | 7/2000 |
| DE | 10055703 A1 | 5/2002 |
| DE | 10303974 A1 | 8/2004 |
| DE | 102004039326 A1 | 2/2006 |
| EP | 0 045 665 B1 | 2/1982 |
| EP | 0045665 A1 | 2/1982 |
| EP | 0 050 424 B1 | 9/1985 |
| EP | 0 285 159 A1 | 10/1988 |
| EP | 0 314 491 | 11/1989 |
| EP | 0 341 491 A2 | 11/1989 |
| EP | 0 084 796 B1 | 5/1990 |
| EP | 391714 A2 | 10/1990 |
| EP | 0 411 974 A1 | 2/1991 |
| EP | 411974 A1 | 2/1991 |
| EP | 0 415 801 A1 | 3/1991 |
| EP | 415801 A1 | 3/1991 |
| EP | 0 237 362 B1 | 3/1992 |
| EP | 0 201 184 B1 | 12/1992 |
| EP | 304013 B1 | 6/1993 |
| EP | 0 229 246 B1 | 8/1993 |
| EP | 0 368 684 B1 | 3/1994 |
| EP | 368684 B1 | 3/1994 |
| EP | 0 239 400 B1 | 8/1994 |
| EP | 0 613 007 A2 | 8/1994 |
| EP | 613007 A2 | 8/1994 |
| EP | 0 623 675 | 11/1994 |
| EP | 0 557 270 B1 | 5/1995 |
| EP | 557270 B1 | 5/1995 |
| EP | 0 519 598 B1 | 6/1995 |
| EP | 519598 B1 | 6/1995 |
| EP | 0 440 619 B1 | 1/1996 |
| EP | 440619 B1 | 1/1996 |
| EP | 0 304 013 B1 | 6/1996 |
| EP | 0 589 877 B1 | 11/1996 |
| EP | 589877 B1 | 11/1996 |
| EP | 0 436 597 B1 | 4/1997 |
| EP | 436597 B1 | 4/1997 |
| EP | 0 258 017 B1 | 6/1997 |
| EP | 2 580 017 B1 | 6/1997 |
| EP | 0 783 104 A1 | 7/1997 |
| EP | 783104 A1 | 7/1997 |
| EP | 0 444 856 B1 | 9/1997 |
| EP | 444856 B1 | 9/1997 |
| EP | 0 813 492 | 1/1998 |
| EP | 816492 A1 | 1/1998 |
| EP | 0 592 127 B1 | 4/1998 |
| EP | 592127 B1 | 4/1998 |

(56) References Cited

FOREIGN PATENT DOCUMENTS

| | | |
|---|---|---|
| EP | 0 274 826 B1 | 8/1998 |
| EP | 274826 B1 | 8/1998 |
| EP | 0 391 714 A2 | 10/1998 |
| EP | 285159 A1 | 10/1998 |
| EP | 0 527 839 B1 | 12/1998 |
| EP | 527839 B1 | 12/1998 |
| EP | 341491 A2 | 11/1999 |
| EP | 1 038 958 | 9/2000 |
| EP | 1 094 080 A2 | 4/2001 |
| EP | 1 130 032 | 11/2001 |
| EP | 1 172 378 A1 | 1/2002 |
| EP | 1 176 195 A1 | 1/2002 |
| EP | 0 877 939 B1 | 6/2002 |
| EP | 877939 B1 | 6/2002 |
| EP | 0 683 234 B1 | 5/2003 |
| EP | 1 308 461 A2 | 5/2003 |
| EP | 683234 B1 | 5/2003 |
| EP | 1 408 333 A2 | 4/2004 |
| EP | 1 420 032 | 5/2004 |
| EP | 1 270 592 B1 | 9/2004 |
| EP | 1 467 212 A1 | 10/2004 |
| EP | 0 592 106 B1 | 11/2004 |
| EP | 1 200 470 B1 | 11/2004 |
| EP | 0 519 596 B1 | 2/2005 |
| EP | 519596 B1 | 2/2005 |
| EP | 1 538 163 A2 | 6/2005 |
| EP | 1 632 242 A2 | 3/2006 |
| EP | 1 092 767 B1 | 10/2006 |
| EP | 1 717 250 A1 | 11/2006 |
| EP | 0 998 495 B1 | 12/2006 |
| EP | 1 731 913 A2 | 12/2006 |
| EP | 998495 B1 | 12/2006 |
| EP | 1 049 712 B1 | 1/2007 |
| EP | 1 741 783 A1 | 1/2007 |
| EP | 1 346 041 B1 | 2/2007 |
| EP | 1 752 472 A2 | 2/2007 |
| EP | 1 592 476 B1 | 4/2007 |
| EP | 0 970 203 B1 | 5/2007 |
| EP | 1 787 998 A1 | 5/2007 |
| EP | 970203 B1 | 5/2007 |
| EP | 0 948 536 B1 | 6/2007 |
| EP | 1 160 256 B1 | 6/2007 |
| EP | 1 379 546 B1 | 6/2007 |
| EP | 1 792 991 A1 | 6/2007 |
| EP | 948536 B1 | 6/2007 |
| EP | 1 842 859 A2 | 10/2007 |
| EP | 1 878 751 A2 | 1/2008 |
| EP | 1 434 053 B1 | 3/2008 |
| EP | 1 521 831 B1 | 4/2008 |
| EP | 1 778 837 B1 | 4/2008 |
| EP | 1 911 765 A2 | 4/2008 |
| EP | 1 781 644 B1 | 5/2008 |
| EP | 0 911 398 B1 | 6/2008 |
| EP | 911398 B1 | 6/2008 |
| EP | 1 976 877 A2 | 10/2008 |
| EP | 2 009 445 A1 | 12/2008 |
| EP | 1 623 719 B1 | 1/2009 |
| EP | 1 681 566 B1 | 8/2009 |
| EP | 1 861 422 B1 | 2/2010 |
| EP | 1 766 396 B1 | 8/2010 |
| EP | 1 720 909 B1 | 11/2011 |
| FR | 2740454 A1 | 4/1997 |
| FR | 2741881 A1 | 6/1997 |
| GB | 1 495 159 A | 12/1997 |
| GB | 2 371 303 A | 7/2002 |
| GR | 1 005 016 B | 10/2005 |
| JP | 4252195 A | 9/1992 |
| JP | 4320694 A | 11/1992 |
| JP | 7209295 A | 8/1995 |
| JP | 7209296 A | 8/1995 |
| JP | 07238096 A | 9/1995 |
| JP | 8245700 A | 9/1995 |
| JP | 7309900 A | 11/1995 |
| JP | 9067397 A | 3/1996 |
| JP | 10075781 A | 3/1998 |
| JP | 10210982 A | 8/1998 |
| JP | 63240797 A | 10/1998 |
| JP | 2000050885 A | 2/2000 |
| JP | 2000354487 A | 12/2000 |
| JP | 2001231578 A | 8/2001 |
| JP | 2002040023 A | 2/2002 |
| JP | 2002253252 A | 9/2002 |
| JP | 2004107260 A | 4/2004 |
| JP | 2005185281 A | 7/2005 |
| JP | 2006166879 A | 6/2006 |
| JP | 2006213621 A | 8/2006 |
| JP | 2006265189 A | 10/2006 |
| JP | 2007077103 A | 3/2007 |
| JP | 2007300856 A | 11/2007 |
| JP | 2007319127 A | 12/2007 |
| JP | 2008096311 A | 4/2008 |
| KR | 100806914 B1 | 2/2008 |
| WO | WO 89/06689 A1 | 7/1989 |
| WO | WO-89/07657 A1 | 8/1989 |
| WO | WO-90/02809 A1 | 3/1990 |
| WO | WO-90/005144 A1 | 5/1990 |
| WO | WO-1990/07861 A1 | 7/1990 |
| WO | WO-90/12870 A1 | 11/1990 |
| WO | WO-90/14424 A1 | 11/1990 |
| WO | WO-90/14430 A1 | 11/1990 |
| WO | WO-90/14443 A1 | 11/1990 |
| WO | WO-91/05548 A1 | 5/1991 |
| WO | WO-91/09967 A1 | 7/1991 |
| WO | WO-91/17271 A1 | 11/1991 |
| WO | WO-92/001047 A1 | 1/1992 |
| WO | WO-92/02551 A1 | 2/1992 |
| WO | WO-92/00969 A1 | 6/1992 |
| WO | WO-92/009690 A2 | 6/1992 |
| WO | WO-92/11018 A1 | 7/1992 |
| WO | WO-92/15679 A1 | 9/1992 |
| WO | WO-92/18619 A1 | 10/1992 |
| WO | WO-92/19244 A2 | 11/1992 |
| WO | WO-92/020791 A1 | 11/1992 |
| WO | WO-92/22324 A1 | 12/1992 |
| WO | WO-93/01288 A1 | 1/1993 |
| WO | WO-93/08302 A1 | 4/1993 |
| WO | WO-93/11236 A1 | 10/1993 |
| WO | WO-94/02602 A1 | 2/1994 |
| WO | WO-94/004679 A1 | 3/1994 |
| WO | WO-94/17197 A1 | 8/1994 |
| WO | WO-95/07707 A1 | 3/1995 |
| WO | WO-95/11311 A1 | 4/1995 |
| WO | WO-95/11994 A1 | 5/1995 |
| WO | WO-95/15982 A2 | 6/1995 |
| WO | WO-95/16787 A1 | 6/1995 |
| WO | WO-95/20401 A1 | 8/1995 |
| WO | WO-96/20218 A1 | 7/1996 |
| WO | WO-96/20698 A1 | 7/1996 |
| WO | WO-96/28187 A1 | 9/1996 |
| WO | WO-96/33735 A1 | 10/1996 |
| WO | WO-96/34096 A1 | 10/1996 |
| WO | WO-96/39512 A2 | 12/1996 |
| WO | WO-96/40731 A1 | 12/1996 |
| WO | WO-97/08320 A1 | 3/1997 |
| WO | WO-97/10505 A1 | 3/1997 |
| WO | WO-97/18476 A1 | 5/1997 |
| WO | WO-97/29131 A1 | 8/1997 |
| WO | WO-97/32572 A2 | 9/1997 |
| WO | WO-97/44013 A1 | 11/1997 |
| WO | WO-97/46678 A1 | 12/1997 |
| WO | WO-98/05350 A1 | 2/1998 |
| WO | WO-98/07850 A2 | 2/1998 |
| WO | WO-98/13490 A2 | 4/1998 |
| WO | WO-98/16654 A1 | 4/1998 |
| WO | WO-98/22120 A1 | 5/1998 |
| WO | WO-88/03951 A1 | 6/1998 |
| WO | WO-98/24884 A1 | 6/1998 |
| WO | WO-98/24893 A2 | 6/1998 |
| WO | WO-98/28445 A1 | 7/1998 |
| WO | WO-98/31346 A1 | 7/1998 |
| WO | WO-98/31700 A1 | 7/1998 |
| WO | WO-98/33815 A1 | 8/1998 |
| WO | WO-98/41201 A1 | 9/1998 |
| WO | WO-98/47343 A2 | 10/1998 |

(56) References Cited

FOREIGN PATENT DOCUMENTS

| | | |
|---|---|---|
| WO | WO-99/54342 A1 | 10/1998 |
| WO | WO-98/49286 A2 | 11/1998 |
| WO | WO-98/50433 A2 | 11/1998 |
| WO | WO-98/51793 A1 | 11/1998 |
| WO | WO-99/05175 A2 | 2/1999 |
| WO | WO-99/09150 A1 | 2/1999 |
| WO | WO-99/12870 A1 | 3/1999 |
| WO | WO-99/13908 A1 | 3/1999 |
| WO | WO-99/15154 A1 | 4/1999 |
| WO | WO-99/20253 A1 | 4/1999 |
| WO | WO-99/22024 A1 | 5/1999 |
| WO | WO-99/25044 A1 | 5/1999 |
| WO | WO-99/27944 A1 | 6/1999 |
| WO | WO-99/27949 A1 | 6/1999 |
| WO | WO-91/10737 A1 | 7/1999 |
| WO | WO-91/10741 A1 | 7/1999 |
| WO | WO-99/33815 A1 | 7/1999 |
| WO | WO-99/36569 A1 | 7/1999 |
| WO | WO-99/40909 A1 | 8/1999 |
| WO | WO-99/45031 A2 | 9/1999 |
| WO | WO-99/45962 A1 | 9/1999 |
| WO | WO-99/53049 A1 | 10/1999 |
| WO | WO-99/55842 A1 | 11/1999 |
| WO | WO-99/58157 A1 | 11/1999 |
| WO | WO-99/58564 A1 | 11/1999 |
| WO | WO-99/59571 A1 | 12/1999 |
| WO | WO-99/62505 A2 | 12/1999 |
| WO | WO-99/66903 A2 | 12/1999 |
| WO | WO-00/09560 A2 | 2/2000 |
| WO | WO-00/017345 A1 | 3/2000 |
| WO | WO-00/018805 A1 | 4/2000 |
| WO | WO-00/029446 A1 | 5/2000 |
| WO | WO-00/032805 A1 | 6/2000 |
| WO | WO-00/035939 A1 | 6/2000 |
| WO | WO-00/037504 A2 | 6/2000 |
| WO | WO-00/056772 A1 | 9/2000 |
| WO | WO-00/058344 A1 | 10/2000 |
| WO | WO-00/072870 A1 | 12/2000 |
| WO | WO-00/072876 A2 | 12/2000 |
| WO | WO-00/072880 A2 | 12/2000 |
| WO | WO-00/075328 A1 | 12/2000 |
| WO | WO-00/077178 A1 | 12/2000 |
| WO | WO-00/78807 A1 | 12/2000 |
| WO | WO-01/010900 A2 | 2/2001 |
| WO | WO-01/16364 A2 | 3/2001 |
| WO | WO-01/018169 A2 | 3/2001 |
| WO | WO-01/032712 A2 | 5/2001 |
| WO | WO-01/039796 A2 | 6/2001 |
| WO | WO-01/042306 A2 | 6/2001 |
| WO | WO-01/062284 A2 | 8/2001 |
| WO | WO-01/62801 A2 | 8/2001 |
| WO | WO-01/062801 A2 | 8/2001 |
| WO | WO-01/068860 A1 | 9/2001 |
| WO | WO-01/083519 A1 | 11/2001 |
| WO | WO-01/083525 A2 | 11/2001 |
| WO | WO-01/83525 A2 | 11/2001 |
| WO | WO-01/85093 A2 | 11/2001 |
| WO | WO-01/090182 A2 | 11/2001 |
| WO | WO-01/098361 A2 | 12/2001 |
| WO | WO-02/000245 A1 | 1/2002 |
| WO | WO-02/003911 A1 | 1/2002 |
| WO | WO-02/03911 A2 | 1/2002 |
| WO | WO-02/021141 A2 | 3/2002 |
| WO | WO-02/030980 A2 | 4/2002 |
| WO | WO-02/034777 A1 | 5/2002 |
| WO | WO-02/036614 A2 | 5/2002 |
| WO | WO-02/046237 | 6/2002 |
| WO | WO-02/055552 A2 | 7/2002 |
| WO | WO-02/059155 A2 | 8/2002 |
| WO | WO-02/062851 A1 | 8/2002 |
| WO | WO-02/074240 A2 | 9/2002 |
| WO | WO-02/081505 A2 | 10/2002 |
| WO | WO-02/085922 A2 | 10/2002 |
| WO | WO-02/088306 A2 | 11/2002 |
| WO | WO-02/088307 A2 | 11/2002 |
| WO | WO-02/094985 A2 | 11/2002 |
| WO | WO-02094870 A2 | 11/2002 |
| WO | WO-02/096350 A2 | 12/2002 |
| WO | WO-02/096937 A2 | 12/2002 |
| WO | WO-03/000714 A2 | 1/2003 |
| WO | WO-03/008626 A2 | 1/2003 |
| WO | WO-03/014162 A2 | 2/2003 |
| WO | WO-03/014329 A2 | 2/2003 |
| WO | WO-03/015617 A2 | 2/2003 |
| WO | WO-03/015691 A2 | 2/2003 |
| WO | WO-03/015812 A2 | 2/2003 |
| WO | WO-03/016466 A2 | 2/2003 |
| WO | WO-03/016467 A2 | 2/2003 |
| WO | WO-03/020212 A2 | 3/2003 |
| WO | WO-03/028668 A2 | 4/2003 |
| WO | WO-03/031475 A2 | 4/2003 |
| WO | WO-03/035835 A2 | 5/2003 |
| WO | WO-03/039467 A2 | 5/2003 |
| WO | WO-03/045128 A1 | 6/2003 |
| WO | WO-03/046012 A2 | 6/2003 |
| WO | WO-03/047499 A2 | 6/2003 |
| WO | WO-03/051374 A2 | 6/2003 |
| WO | WO-03/070760 A2 | 8/2003 |
| WO | WO-03/074081 A1 | 8/2003 |
| WO | WO-03/074004 A2 | 9/2003 |
| WO | WO-03/074569 A2 | 9/2003 |
| WO | WO-03/074715 A2 | 9/2003 |
| WO | WO-03/076455 A2 | 9/2003 |
| WO | WO-03/077858 A2 | 9/2003 |
| WO | WO-03/080672 A1 | 10/2003 |
| WO | WO-03/089460 A1 | 10/2003 |
| WO | WO-03/090772 A1 | 11/2003 |
| WO | WO-03/091734 A1 | 11/2003 |
| WO | WO-03/095429 A1 | 11/2003 |
| WO | WO-03/100419 A1 | 12/2003 |
| WO | WO-03/104437 A2 | 12/2003 |
| WO | WO-03/105658 A2 | 12/2003 |
| WO | WO-2004/001422 A2 | 12/2003 |
| WO | WO-2004/003019 A2 | 1/2004 |
| WO | WO-2004/003563 A2 | 1/2004 |
| WO | WO-2004/006861 A2 | 1/2004 |
| WO | WO-2004/009776 A2 | 1/2004 |
| WO | WO-2004/011674 A1 | 2/2004 |
| WO | WO-2004/011943 A1 | 2/2004 |
| WO | WO-2004/013172 A2 | 2/2004 |
| WO | WO-2004/014296 A2 | 2/2004 |
| WO | WO-2004/014367 A2 | 2/2004 |
| WO | WO-2004/016282 A2 | 2/2004 |
| WO | WO-2004/016655 A1 | 2/2004 |
| WO | WO-2004/018997 A2 | 3/2004 |
| WO | WO-2004/019045 A2 | 3/2004 |
| WO | WO-2004/024090 A2 | 3/2004 |
| WO | WO-2004/029093 A2 | 4/2004 |
| WO | WO-2004/029630 A1 | 4/2004 |
| WO | WO-2004/031241 A1 | 4/2004 |
| WO | WO-2004/031400 A2 | 4/2004 |
| WO | WO-2004/032868 A2 | 4/2004 |
| WO | WO-2004/033397 A2 | 4/2004 |
| WO | WO-2004/038411 A2 | 5/2004 |
| WO | WO-2004/041067 A2 | 5/2004 |
| WO | WO-2004/043989 A2 | 5/2004 |
| WO | WO-2004/044204 A2 | 5/2004 |
| WO | WO-2004/045525 A2 | 6/2004 |
| WO | WO-2004/050707 A2 | 6/2004 |
| WO | WO-2004/050850 A2 | 6/2004 |
| WO | WO-2004/050876 A1 | 6/2004 |
| WO | WO-2004/056318 A2 | 7/2004 |
| WO | WO-2004/058239 A1 | 7/2004 |
| WO | WO-2004/058258 A1 | 7/2004 |
| WO | WO-2004/058820 A2 | 7/2004 |
| WO | WO-2004/062556 A2 | 7/2004 |
| WO | WO-2004/065419 A2 | 8/2004 |
| WO | WO-2004/065569 A2 | 8/2004 |
| WO | WO-2004/067561 A1 | 8/2004 |
| WO | WO-2004/068931 A2 | 8/2004 |
| WO | WO-2004/069182 A2 | 8/2004 |
| WO | WO 2004/071408 A2 | 8/2004 |
| WO | WO-2004/072286 A1 | 8/2004 |
| WO | WO-2004/074837 A1 | 9/2004 |

(56) References Cited

FOREIGN PATENT DOCUMENTS

| | | |
|---|---|---|
| WO | WO-2004/078140 A2 | 9/2004 |
| WO | WO-2004/085712 A2 | 10/2004 |
| WO | WO-2004/087733 A2 | 10/2004 |
| WO | WO-2004/087735 A2 | 10/2004 |
| WO | WO-2004/090544 A2 | 10/2004 |
| WO | WO-2004/095031 A1 | 11/2004 |
| WO | WO-2004/098631 A1 | 11/2004 |
| WO | WO-2004/104597 A1 | 12/2004 |
| WO | WO-2004/108895 A2 | 12/2004 |
| WO | WO-2004/111250 A1 | 12/2004 |
| WO | WO-2005/000897 A2 | 1/2005 |
| WO | WO-2005/005638 A2 | 1/2005 |
| WO | WO-2005/011599 A2 | 2/2005 |
| WO | WO-2005/012330 A2 | 2/2005 |
| WO | WO-2005/014618 A2 | 2/2005 |
| WO | WO-2005/016236 A2 | 2/2005 |
| WO | WO-2005/018424 A2 | 3/2005 |
| WO | WO-2005/018536 A2 | 3/2005 |
| WO | WO-2005/025516 A2 | 3/2005 |
| WO | WO-2005/025592 A2 | 3/2005 |
| WO | WO-2005/025616 A1 | 3/2005 |
| WO | WO-2005-026360 A1 | 3/2005 |
| WO | WO-2005/027965 A1 | 3/2005 |
| WO | WO-2005/027968 A1 | 3/2005 |
| WO | WO-2005/028511 A2 | 3/2005 |
| WO | WO-2005/033142 A2 | 4/2005 |
| WO | WO-2005/033145 A1 | 4/2005 |
| WO | WO-2005/037209 A2 | 4/2005 |
| WO | WO-2005/040212 A2 | 5/2005 |
| WO | WO-2005/041650 A1 | 5/2005 |
| WO | WO-2005/044306 A2 | 5/2005 |
| WO | WO-2005/046605 A2 | 5/2005 |
| WO | WO-2005/047484 A2 | 5/2005 |
| WO | WO-2005/047860 A2 | 5/2005 |
| WO | WO-2005/051998 A2 | 6/2005 |
| WO | WO-2005/052002 A2 | 6/2005 |
| WO | WO-2005/053604 A2 | 6/2005 |
| WO | WO-2005/058815 A2 | 6/2005 |
| WO | WO-2005/058940 A2 | 6/2005 |
| WO | WO-2005/062967 A2 | 7/2005 |
| WO | WO-2005/120571 A2 | 7/2005 |
| WO | WO-2005/070965 A2 | 8/2005 |
| WO | WO-2005/072777 A2 | 8/2005 |
| WO | WO-2005/080986 A1 | 9/2005 |
| WO | WO-2005/081872 A2 | 9/2005 |
| WO | WO-2005/090971 A1 | 9/2005 |
| WO | WO-2005/095457 A2 | 10/2005 |
| WO | WO-2005/096730 A2 | 10/2005 |
| WO | WO-2005/100584 A2 | 10/2005 |
| WO | WO-2005/105841 A2 | 11/2005 |
| WO | WO-2005/105847 A2 | 11/2005 |
| WO | WO-2005/105998 A1 | 11/2005 |
| WO | WO-2005/108378 A2 | 11/2005 |
| WO | WO-2005/110056 A2 | 11/2005 |
| WO | WO-2005/123775 A1 | 11/2005 |
| WO | WO-2005/121177 A2 | 12/2005 |
| WO | WO-2005/123776 A1 | 12/2005 |
| WO | WO-2006/005588 A1 | 1/2006 |
| WO | WO-2006/005707 A2 | 1/2006 |
| WO | WO-2006/014478 A1 | 2/2006 |
| WO | WO-2006/015976 A1 | 2/2006 |
| WO | WO-2006/016644 A1 | 2/2006 |
| WO | WO-2006/033688 A2 | 3/2006 |
| WO | WO-2006/036291 A2 | 4/2006 |
| WO | WO-2006/037604 A1 | 4/2006 |
| WO | WO-2006/038729 A1 | 4/2006 |
| WO | WO-2006/039327 A2 | 4/2006 |
| WO | WO-2006/039470 A2 | 4/2006 |
| WO | WO-2006/040153 A2 | 4/2006 |
| WO | WO-2006/041934 A2 | 4/2006 |
| WO | WO-2006/047254 A1 | 5/2006 |
| WO | WO-2006/047670 A2 | 5/2006 |
| WO | WO-2006/050041 A2 | 5/2006 |
| WO | WO-2006/050667 A1 | 5/2006 |
| WO | WO-2006/052924 A2 | 5/2006 |
| WO | WO-2006/053428 A1 | 5/2006 |
| WO | WO-2006/055178 A2 | 5/2006 |
| WO | WO-2006/066049 A2 | 6/2006 |
| WO | WO-2006/066089 A1 | 6/2006 |
| WO | WO-2006/066118 A2 | 6/2006 |
| WO | WO-2006/066171 A1 | 6/2006 |
| WO | WO-2006/066233 A1 | 6/2006 |
| WO | WO-2006/067792 A2 | 6/2006 |
| WO | WO-2006/069081 A2 | 6/2006 |
| WO | WO-2006/069202 A2 | 6/2006 |
| WO | WO-2006/081171 A1 | 8/2006 |
| WO | WO-2006/083533 A2 | 8/2006 |
| WO | WO-2006/083689 A2 | 8/2006 |
| WO | WO-2006/087550 A2 | 8/2006 |
| WO | WO-2006/094192 A2 | 9/2006 |
| WO | WO-2006/094724 A2 | 9/2006 |
| WO | WO-2006/095041 A1 | 9/2006 |
| WO | WO-2006/096529 A2 | 9/2006 |
| WO | WO-2006/096653 A2 | 9/2006 |
| WO | WO-2006/099543 A2 | 9/2006 |
| WO | WO-2006/100679 A2 | 9/2006 |
| WO | WO-2006/103116 A1 | 10/2006 |
| WO | WO-2006/110748 A2 | 10/2006 |
| WO | WO-2006/116369 A2 | 11/2006 |
| WO | WO-2006/118959 A2 | 11/2006 |
| WO | WO-2006/119449 A2 | 11/2006 |
| WO | WO-2006/121656 A2 | 11/2006 |
| WO | WO-2006/125830 A2 | 11/2006 |
| WO | WO-2006/128163 A2 | 11/2006 |
| WO | WO-2006/133164 A2 | 12/2006 |
| WO | WO-2006/137354 A1 | 12/2006 |
| WO | WO-2007/005358 A2 | 1/2007 |
| WO | WO-2007/005359 A1 | 1/2007 |
| WO | WO-2007/008547 A2 | 1/2007 |
| WO | WO-2007/011639 A2 | 1/2007 |
| WO | WO-2007/011834 A2 | 1/2007 |
| WO | WO-2007/017686 A2 | 2/2007 |
| WO | WO-2007/019620 A1 | 2/2007 |
| WO | WO-2007/021886 A2 | 2/2007 |
| WO | WO-2007/022416 A2 | 2/2007 |
| WO | WO-2007/040437 A1 | 4/2007 |
| WO | WO-2007/042261 A2 | 4/2007 |
| WO | WO-2007/047967 A2 | 4/2007 |
| WO | WO-2007/047995 A2 | 4/2007 |
| WO | WO-2007/050359 A2 | 5/2007 |
| WO | WO-2007/053661 A2 | 5/2007 |
| WO | WO-2007/059135 A2 | 5/2007 |
| WO | WO-2007/059203 A2 | 5/2007 |
| WO | WO-2007/062088 A1 | 5/2007 |
| WO | WO-2007/062852 A2 | 6/2007 |
| WO | WO-2007/064917 A2 | 6/2007 |
| WO | WO-2007/064919 A2 | 6/2007 |
| WO | WO 2007/064972 A2 | 6/2007 |
| WO | WO-2007/067512 A2 | 6/2007 |
| WO | WO-2007/068411 A2 | 6/2007 |
| WO | WO-2007/068429 A1 | 6/2007 |
| WO | WO-2007/082750 A1 | 7/2007 |
| WO | WO-2007/068412 A3 | 8/2007 |
| WO | WO-2007/088399 A1 | 8/2007 |
| WO | WO-2007/088712 A1 | 8/2007 |
| WO | WO-2007/090872 A2 | 8/2007 |
| WO | WO-2007/092861 A2 | 8/2007 |
| WO | WO-2007/096076 A2 | 8/2007 |
| WO | WO-2007/097251 A1 | 8/2007 |
| WO | WO-2007/098417 A2 | 8/2007 |
| WO | WO-2007/103788 A2 | 9/2007 |
| WO | WO-2007/106617 A2 | 9/2007 |
| WO | WO-2007/108756 A1 | 9/2007 |
| WO | WO-2007/109107 A2 | 9/2007 |
| WO | WO-2007/109749 A2 | 9/2007 |
| WO | WO-2007/112288 A2 | 10/2007 |
| WO | WO-2007/113172 A2 | 10/2007 |
| WO | WO-2007/118984 A2 | 10/2007 |
| WO | WO-2007/119685 A1 | 10/2007 |
| WO | WO-2007/123345 A1 | 11/2007 |
| WO | WO-2007/125351 A1 | 11/2007 |
| WO | WO-2007/127393 A2 | 11/2007 |
| WO | WO-2007/127448 A2 | 11/2007 |
| WO | WO-2007/129457 A1 | 11/2007 |

(56) References Cited

FOREIGN PATENT DOCUMENTS

| | | |
|---|---|---|
| WO | WO-2007/144198 A2 | 12/2007 |
| WO | WO-2007/149032 A1 | 12/2007 |
| WO | WO-2008/002893 A2 | 1/2008 |
| WO | WO-2008/008939 A2 | 1/2008 |
| WO | WO-2008/011348 A2 | 1/2008 |
| WO | WO-2008/012101 A1 | 1/2008 |
| WO | WO-2008/015384 A1 | 2/2008 |
| WO | WO-2008/021296 A2 | 2/2008 |
| WO | WO-2008/022349 A2 | 2/2008 |
| WO | WO-2008/027526 A1 | 3/2008 |
| WO | WO-2008/028939 A1 | 3/2008 |
| WO | WO-2008/030251 A1 | 3/2008 |
| WO | WO-2008/030973 A2 | 3/2008 |
| WO | WO-2008/031911 A1 | 3/2008 |
| WO | WO-2008/045962 A2 | 4/2008 |
| WO | WO-2008/047111 A1 | 4/2008 |
| WO | WO-2008/051017 A1 | 5/2008 |
| WO | WO-2008/051326 A2 | 5/2008 |
| WO | WO-2008/057240 A2 | 5/2008 |
| WO | WO-2008/060364 A2 | 5/2008 |
| WO | WO-2008/061795 A2 | 5/2008 |
| WO | WO-2008/064244 A2 | 5/2008 |
| WO | WO-2008/067464 A2 | 6/2008 |
| WO | WO-2008/070229 A2 | 6/2008 |
| WO | WO-2008/071394 A1 | 6/2008 |
| WO | WO-2008/084402 A2 | 7/2008 |
| WO | WO-2008/104385 A1 | 9/2008 |
| WO | WO-2008/104385 A8 | 9/2008 |
| WO | WO-2008/104386 A2 | 9/2008 |
| WO | WO-2008/104386 A3 | 9/2008 |
| WO | WO-2008/107677 A2 | 9/2008 |
| WO | WO-2008/110885 A2 | 9/2008 |
| WO | WO-2008/122441 A2 | 10/2008 |
| WO | WO-2008/124940 A2 | 10/2008 |
| WO | WO-2008/129023 A2 | 10/2008 |
| WO | WO-2008/130449 A2 | 10/2008 |
| WO | WO-2008/131298 A2 | 10/2008 |
| WO | WO-2008/134034 A2 | 11/2008 |
| WO | WO-2008/143708 A2 | 11/2008 |
| WO | WO-2008/150467 A2 | 12/2008 |
| WO | WO-2008/150946 A1 | 12/2008 |
| WO | WO-2008/150949 A1 | 12/2008 |
| WO | WO-2008/156621 A1 | 12/2008 |
| WO | WO-2008/156622 A1 | 12/2008 |
| WO | WO-2009/008890 A1 | 1/2009 |
| WO | WO-2009/008891 A1 | 1/2009 |
| WO | WO-2009/009768 A2 | 1/2009 |
| WO | WO-2009/044160 A1 | 4/2009 |
| WO | WO-2009/048537 A2 | 4/2009 |
| WO | WO-2009/048538 A2 | 4/2009 |
| WO | WO-2009/048539 A2 | 4/2009 |
| WO | WO-2009/134711 A1 | 11/2009 |
| WO | WO-2009/134711 A8 | 11/2009 |
| WO | WO-2010/011947 A2 | 1/2010 |
| WO | WO-2010/011947 A3 | 1/2010 |
| WO | WO-2010/097012 A1 | 9/2010 |
| WO | WO-2011/157285 A1 | 12/2011 |
| WO | WO-2012/024187 A1 | 2/2012 |
| WO | WO-2006/014638 A2 | 2/2016 |

OTHER PUBLICATIONS

Aisen. et al. "The Development of Anti-Amyloid Etherapy for Alzheimer's Disease: From Secretase Modulators to Polymerisation Inhibitors," *CNS Drugs* 19(12):989-996, (2005).
Albert et al. "Time-Dependent Induction of Protective Anti-Influenza Immune Responses in Human Peripheral Blood Lymphocyte/ SCID Mice," *J. Immunol.* 153(3):1393-1403, (1997).
Almquist et al. "Synthesis and Biological Activity of a Ketomethylene Analogue of a Tripeptide Inhibitor of Angiotensin Converting Enzyme," *J. Med. Chem.* 23:1392-1398, (1980).
Altschul et al. "Gapped BLAST and PSI_BLAST: a New Generation of Protein Database Search Programs," *Nucl. Acids Res.* 25(17):3389-3402, (1997).

Ames, R.S. et al. "Conversion of Murine Fabs Isolated from a Combinatorial Phage Display Library to Full Length Immunoglobulins," *J. Immunol. Meth.* 184:177-186, (1995).
Anderson et al. "Characterization of Beta Amyloid Assemblies in Drusen: The Deposits Associated With Aging and Age-Related Macular Degeneration," *Experimental Eye Research* 78:243-256, (2004).
Arai et al. "An ELISA to Determine the Biodistribution of Human Monoclonal Antibody in Tumor-Xenografted Scid Mice," *J. Immunol. Meth.* 217:79-85, (1998).
Ardaillou, R. "An Ang II Antagonist Improves the Alzheimer's Disease of the Mouse," *Medicine/Sciences* 24(1):41-47, (2008).
Arispe et al. "Alzheimer Disease Amyloid Beta Protein Forms Calcium Channels in Bilayer membranes: Blockage by Tromethamine and Aluminum," *Proc. Natl. Acad. Sci. USA* 90:567-571, (1993).
Armstrong, J. et al. "Familial Alzheimer Disease Associated with a 713T Mutation in APP," *Neurosci. Letters* 370:241-243, (2004).
Asakura et al. "Alpha-Eudesmol, a P/Q-type Ca2+ Channel Blocker, Inhibits Neurogenic Vasodilatation and Extravasation Following Electrical Stimulation of Trigeminal Gangion," *Brain Res.* abstract 873:94-101, (2000).
Asakura et al. "P/Q-Type Ca2+ Channel Blocker Game-Agatoxin IV A Protects Against Brain Injury After Focal Ischemia in Rats," *Brain Res.* abstract 776:140-145, (1997).
Askanas et al., "Inclusion-Body Myositis: a Myodegenerative Conformational Disorder Associated with Abeta, Protein Misfolding, and Proteasome Inhibition," *Neurology* 66(2) Supp I:S39-48, (2006).
Askanas et al. "Molecular Pathology and Pathogenesis of Inclusion-Body Myositis," *Microscopy Res. Technique* 67:114-120, (2005).
Askanas et al. "Proposed Pathogenetic Cascade of Inclusion-Body Myositis: Importance of Amyloid-Beta, Misfolded Proteins, Predisposing Genes, and Aging," *Curr. Opin. Rheumatol.* 15(6):737-744, (2003).
Atherton et al. "The Fluorenylmethoxycarbonyl Amino Protecting Group," *The Peptides: Analysis, Synthesis, Biology Academic Press* 9:1-38, (1987).
Ausubel et al. *Current Protocols in Molecular Biology* Table of Contents, (1993).
Ausubel et al. *Short Protocols in Molecular Biology, 3rd Edition* Table of Contents, (1995).
Ausubel et al. *Current Protocols in Molecular Biology*, (1989).
Author Guidelines, *Journal of Neurochemistry*, 13:1-14, (Jun. 2012).
Auvynet et al. "Structural Requirements for Antimicrobial Versus Chemoattractant Activities for Dermaseptin S9," *FEBS J.* 2754134-4151, (2008).
Awasthi et al. "Amyloid-Beta Causes Apoptosis of Newronal Cells Via Caspase Cascade, Which Can Be Prevented by Amyloid-Beta-Derived Short Peptides," *Exp. Neurology* (2005) 196(2):282-289, (2005).
Azzazy et al. "Phage Display Technology: Clinical Applications and Recent Innovations," *Clin. Biochem.* 35:425-445, (2002).
Babcock et al. "A Novel Strategy for Generating Monoclonal Antibodies From Single, Isolated Lymphocytes Producing Antibodies of Defined Specificities," *Proc. Natl. Acad. Sci. USA* 93:7843-7848, (1996).
Bagriantsev et al. "Modulation of Abeta SUB 42 Low-N Oligomerization Using a Novel Yeast Reporter System," *BMC Biol.* 4:32, 12 pages, (2006).
Banker et al. "Rat Hippocahmpal Neurons in Dispersed Cell Culture," *Brain Res.* 126(3):397-425, (1977).
Barany et al. "Solid-Phase Peptide Synthesis," *The Peptides: Analysis, Synthesis, Biology, Academic Press*, Gross editor, 2:1-284, (1980).
Barbas, III et al. "Assembly of Combinatorial Antibody Libraries on Phage Surfaces: The Gene III Site," *Proc. Natl. Acad. Sci. USA* 88:7978-7982, (1991).
Bard et al. "Epitope and Isotype Specificities of Antibodies to Beta-Amyloid Peptide for Protection Against Alzheimer's Disease-Like Neuropathology," *Proc. Natl. Acad. Sci. USA* 100(4):2023-2028, (2003).

(56) References Cited

OTHER PUBLICATIONS

Bard et al. "Peripherally Administered Antibodies Against Amyloid Bipeptide Enter the Central Nervous System and Reduce Pathology in a Mouse Model of Alzheimer Disease," *Nature Med.* 6:916-919, (2000).
Barghorn et al., "Globular Amyloid Beta-Peptide Oligomer—A Homogeneous and Stable Neuropathological Protein in Alzheimer's Disease", *J. Neurochem.*, 95(3):834-847, (Aug. 31, 2005).
Barghorn 168,760et al. "Abeta-Oligomer Selective Antibody A-887755 Exhibits a Favorable Profile for Alzheimer's Disease Immunotherapy Compared to Abeta-Peptide Unselective Antibodies," *Alzheimer's & Dementia: The Journal of the Alzheimer's & Association* 5(4):P424, (2009).
Barrow et al. "Solution Conformations and Aggregational Properties of Synthetic Amyloid Beta-Peptides of Alzheimer's Disease. Analysis of Circular Dichroism Spectra," *J. Mol. Biol.* 225(4): 1075-1093, (1992).
Bartolini et al. "Insight Into the Kinetic of Amyloid Beta (1-42) Peptide Self-Aggregation: Elucidation of Inhibitors' Mechanism of Action," *Chembiochem.* 8(17):2152-61, (2007).
Bateman et al. "Specific Binding of Alzheimer Amyloid Peptides to the Cell Surface Implicates the Presence of a Membrane Receptor," *Neurobiol. of Aging 9th International Conf. on Alzheimers Disease and Related Disorders*, Philadelphia, PA, Jul. 17-22, 2004.
Bateman et al. "Human Amyloid-Beta Synthesis and Clearance Rates as Measured in Cerebrospinal Fluid In Vivo," *Nature Med.* 12(7):856-861, (2006).
Bates et al. "Clearance Mechanisms of Alzheimer's Amyloid-Beta Peptide: Implications for Therapeutic Design and Diagnostic Tests," *Mol. Psych.* 14(5):469-486, (2009).
Bayer et al. "Review on the APP/PS Lkl Mouse Model: Intraneuronal A Beta Accumulation Triggers Axonopathy, Neuron Loss and Working Memory Impairment," *Genes Brain Behav.* 7:6-11, (2008).
Bedzyk et al. "Active Site Structure and Antigen Binding Properties of Idiotypically Cross-Reactive Anti-Fluorescein Monoclonal Antibodies," *J. Biol. Chem.* 265(1):133-138, (1990).
Bell et al. "MAPK Recruitment by Beta-Amyloid in Organotypid Hippocampal Slice Cultures Depends on Physical State and Exposure Time," *J. Neurochem.* 91(2):349-361, (2004).
Belokon et al. "Improved Procedures for the Synthesis of (S)-2-[N-(N'-Benzyl-Prolyl)Amino]Benzophenoe (BPB) and Ni(II) Complexes of Schiff's Bases Derived From BPB and Amino Acids," *Tetrahedron: Asymmetry* 9:4249-4252, (1998).
Bendig et al. "Humanization of Rodent Monoclonal Antibodies by CDR Grafting," *Methods: A Companion to Methods in Enzymology* 8:83-93, (1995).
Benevenuti et al. "Crystallization of Soluble Proteins in Vapor Diffusion for Xray Crystallography," *Nature Protocols* 2(7):1633-1651, (2007).
Bennett, et al. "Immunization Therapy for Alzheimer Disease?," *Neurology* 64:10-12, (2005).
Berman et al. "Oligomeric Amyloid-Beta Peptide Disrupts Phosphatidylinositol-4,5-Bisphosphate Metabolism," *Nat. Neurosci.* 11(5):547-554, (2008).
Bernstein et al. "Amyloid Beta-Protein: Monomer Structure and Early Aggregation States of Abeta42 and Its Pro SUP 19 Alloform," *J. Am. Chem. Soc.* 127(7):2075-2084, (2005).
Bernstein et al. "Amyloid-Beta Protein Oligomerization and the Importance of Tetramers and Dodecamers in the Aetiology of Alzheimer's Disease," *Nature Chem.* 1:326-331, (2009).
Better et al. "*Escherichia Coli* Secretion of an Active Chimeric Antibody Fragment," *Science* 240:1041-1043, (1988).
Bezprozvanny et al. "Neuronal calcium mishandling and the pathogenesis of Alzheimer's disease," *Trends Neurosci.* 31(9):454-463, (2008).
Bharadwaj et al. "A New Method to Measure Cellular Toxicity of Non-Fibrillar and Fibrillar Alzheimer's Abeta Using Yeast," *J. Alzheimer's Disease* 13(2):147-150, (2008).

Bhaskar et al. "The PI3K-Akt-Mtor Pathway Regulates a Oligomer Induced Neuronal Cell Cycle Events," *Mol. Neurodegeneration* 4:1, (2009).
Bieniarz et al. "Extended Length Heterobifunctional Coupling Agents for Protein Conjugations," *Bioconjug. Chem.* 7(1):88-95, (1996).
Bird et al. "Single-Chain Antigen-Binding Proteins," *Science* 242(4877):423-426, (Oct. 21, 1988).
Birren et al. Genome Analysis—A Laboratory Manual, vols. 1 & 2, Table of Contents, (1998).
Bitan et al., "A Molecular Switch in Amyloid Assembly: Met35 and Amyloid Beta-Protein Oligomerization," *J. Am. Chem. Soc.* 125:15359-15365, (2003).
Bitan et al., "Amyloid Beta-Protein (Abeta) Assembly: Abeta40 and Abeta42 Oligomerize Through Distinct Pathways," *Proc. Natl. Acad. Sci. USA* 100(1):330-335, (2003).
Bitan et al. "Primary-Quaternary Structure Relationships Controlling Early a Beta Oligomerizationpeptide Revolution: Genomics, Proteomics and Therapeutics," *18th American Peptide Symposium*, Boston, MA pp. 765-767, (Jul. 19-23, 2003).
Bitan et al. "Towards Inhibition of Amyloid Beta-Protein Oligomerization," *Biopolymers 80573, 19th American Peptide Symposium*, San Diego, CA, (Jun. 18-23, 2005).
Bobich et al. "Incubation of Nerve Endings With a Physiological Concentration of Abeta SUB 1-42 Activates Cav2.2(N-Type)-Voltage Operated Calcium Channels and Acutely Increases Glutamate and Noradrenaline Release," *J. Alzheimer's Dis.* 6(3):243-255, (2004).
Bocher et al. "Antigen-Specific Band T Cells in Human/Ouse Radiation Chimera Following Immunization In Vivo," *Immunol.* 96:634-641, (1999).
Bombil et al. "A Promising Model Ofprimaray Human Immunization in Human-SCID Mouse," *Immuolbiol.* 195:360-375, (1996).
Boridy et al. "The Binding of Pullalan Modified Cholesteryl Nanogels to Abeta Oligomers and Their Suppression of Cytotoxicity," *Biomaterials* 30(29):5583-5591, (2009).
Boss et al. "Genetically Engineered Antibodies," *Immunol.* 6(1):12-13, (1985).
Boutaud et al. "PGH SUB 2-Derived Levuglandin Adducts Increase the Neurotoxicity of Amyloid Beta 1-42," *J. Neurochem.* 96(4):917-923, (2006).
Boutaud et al. "Prostaglandin H2 (PGH2) Accelerates Formation of Amyloid Betal-42 Oligomers," *J. Neurochem.* 82:1003-1006, (2002).
Boyd-Kimball et al. "Neurotoxicity and Oxidative Stress in DIM-Substituted Alzheimer's Abeta(L-42): Relevance to N-Terminal Methionine Chemistry in Small Model Peptides," *Peptides* 26:665-673, (2005).
Bravo et al. "Sulfated Polysaccharides Promote the Assembly of Amyloid Beta 1-42 Peptide Into Stable Fibrils of Reduced Cytotoxicity," *J. Biol. Chem.* 283:32471-32483, (2008).
Brettschneider et al. "Decreased Serum Amyloid Betal-42 Autoantibody Levels in Alzheimer's Disease, Determined by a Newly Developed Immuno-Precipitation Assay With Radiolabeled Amyloid Betal-42 Peptide," *Biol. Psychiatry* 57:813-816, (2005).
Brinkley, M.A. "A Survey of Methods for Preparing Protein Conjugates With Dyes, Haptens and Crosslinking Reagents," *Bioconjugate Chem.* 3:2-13, (1992).
Brinkman et al. "Phage Display of Disulfide-Stabilized FV Fragments," *J. Immunol. Meth.* 182:41-50, (1995).
Britschgi et al. "Neuroprotective Natural Antibodies to Assemblies of Amyloidogenic Peptides Decrease With Normal Aging and Advancing Alzheimer's Disease," *Proc. Natl. Acad. Sci. USA* 106(29):12145-12150, (2009).
Brorson et al. "Mutational Analysis of Avidity and Fine Specificity of Anti-Levan Antibodies," *J. Immunol.* 163:6694-6701, (1999).
Brown et al. "Protein Antigens of Normal and Malignant Human Cells Identified by Immunoprecipitation With Monoclonal Antibodies," *J. Biol. Chem.* 255(11):4980-4983, (1980).
Brown et al. "Structural characterization of human melanoma-associated antigen p97 with monoclonal antibodies," *J. Immunol.* 127(2):539-546, (1981).

(56) References Cited

OTHER PUBLICATIONS

Brown et al. "Tolerance to Single, But Not Multiple, Amino Acid Replacements in Antibody V-H CDR2: A Means of Minimizing B Cell Wastage From Somatic Hypermutation?" *J. Immunol.* 156(9):3285-3291, (1996).

Brummell et al. "Probing the Combining Site of an Anti-Carbohydrate Antibody by Saturation-Mutagenesis: Role of the Heavy-Chain CDR3 Residues," *Biochem.* 32:1180-1187, (1993).

Brunger et al. "Crystallography and Nmr System: a New Software Suite for Macromolecular Structure Determination," *Acta Crystallogr.* D54(Pt5):905-921, (1998).

Brutlag, D. "Computational Molecular Biology—Multiple Sequence Alignment," (2007).

Buchwald et al. "Long-Term Continuous Intravenous Heparin Administration by an Implantable Infusion Pump in Ambulatory Patients With Recurrent Venous Thrombosis," *Surgery* 88:507-516, (1980).

Buraei et al. "Roscovitine Differentially Affects Cav2 and Kv Channels by Binding to the Open State," *Neuropharmacology* 52:883-894, (2007).

Burks et al. "In Vitro Scanning Saturation Mutagenesis of an Antibody Binding Pocket," *Proc. Natl. Acad. Sci. USA* 94:412-417, (1997).

Burton et al. "Human Antibodies From Combinatorial Libraries," *Adv. In Immunol.* 57:191-208, (1994).

Butler et al. "Cellular Responses to Protein Accumulation Involve Autophagy and Lysosomal Enzyme Activation," *Rejuvenation Res.* 8(4):227-237, (2005).

Campbell et al. "General Properties and Applications of Monoclonal Antibodies," *Elsevier Science Publishers B.V.* pp. 1-32, (1984).

Carlsson et al. "Protein Thiolation and Reversible Protein-Protein Conjugation. N-Succinimidyl 3-(2-Pyridyldithio) Propionate, A New Heterobifunctional Reagent," *Biochem. J.* 173(3):723-737, (1978).

Carter et al. "More Missense in Amyloid Gene," *Nat. Genet.* 2:255-256, (1992).

Carter et al. "Humanization of an Anti-PI 85HER2 Antibody for Human Cancer Therapy," *Proc. Natl. Acad. Sci. USA* 89:4285-4289, (1992).

Cassett et al. "A Peptide Mimetic of an Anti-CD4 Monoclonal Antibody by Rational Design," *Biochem. Biophys. Res. Comm.* 307:198-205, (2003).

Catterall et al. "International Union of Pharmacology. XL VIII. Nomenclature and Structure-Function Relationships of Voltage-Gated Calcium Channels," *Pharm. Rev.* 57(4):411-425, (2005).

Cecchini et al. "Increased Susceptibility to Amyloid Toxicity in Familial Alzheimer's Fibroblasts," *Neurobiol. Aging* 28(6):863-876, (2007).

Cecchini et al. "A Molecular Dynamics Approach to the Structural Characterization of Amyloid Aggregation," *J. Mol. Biol.* 357(4):1306-1321, (2006).

Celli et al. "Origin and Pathogenesis of Antiphospholipid Antibodies," *Braz. J. Med. Biol. Res.* (1998) 31(6):723-732, (1998).

Chacon et al. "Frizzled-1 Is Involved in He Neuroprotective Effect Ofwnt3a Against Abeta Oligomers," *J. Cell. Physiol.* 217(1):215-227, (2008).

Chaiken, I.M. "Semisynthetic Peptides and Proteins," *CRC Crit. Rev. Biochem.* 11(3):255-301, (1981).

Chamat et al. "Human Monoclonal Antibodies Isolated From Spontaneous Epstein-Barr Virus-Transformed Tumors Ofhu-SPL-SCID Mice and Specific for Fusion Protein Display Broad Neutralizing Activity Toward Respiratory Syncytial Virus," *J. Infect. Dis.* 180:268-277, (1999).

Chander et al., "Binding of Trypsin to Fibrililar Amyloid Beta-Protein," *Brain Res.* 1082(1):173-181, (2006).

Chang et al., "Femtomole Immunodetection of Synthetic and Endogenous Amyloid-Beta Oligomers and Its Application to Alzheimer's Disease Drug Candidate Screening," *J. Mol. Neurosci.* 20(3):305-313, (2003).

Chanki et al. "Ex Situ Atomic Force Microscopy Analysis Ofbeta-Amyloid Self-Assembly and Deposition on a Synthetic Template," *Langmuir* 16(22):6977-6985, (2006).

Chen et al. "Selection and Analysis of an Optimized Anti-VEGF Antibody: Crystal Structure of an Affinity-Matured Fabin Complex With Antigen," *J. Mol. Biol.* 293:865-881, (1999).

Chen et al. "Cooperation Between NOD2 and Toll-Like Receptor 2 Ligands in the Up-Regulation of Mouse Mfpr2, A G-Protein-Coupled Aalpha SUB 42 Peptide Receptor, in Microglial Cells," *J. Leukocyte Biol.* 83(6):1467-1475, (2008).

Chen et al. "Distinct Early Folding and Aggregation Properties of Alzheimer Amyloid-Beta Peptides A Beta 40 and A Beta 42—Stable Trimer or Tetramer Formation by A Beta 42," *J. Biol. Chem.* 281:24414-24422, (2006).

Chen, C. "Beta-Amyloid Increases Dendritic Ca2+ influx by Inhibiting the A-Type K+ Current in Hippocampal CA1 Pyramidal Neurons," *Biochem. Biophys. Res. Comm.* 338:1913-1919, (2005).

Chiang et al. "Distinctive Roles of Different Beta-Amyloid 42 Aggregates in Modulation of Synapticfunctions," *FASEB Journal* 23(6):1969-1977, (2009).

Chiang et al. "The Many Faces of Amyloid Beta in Alzheimer's Disease," *Curr. Mol. Med.* 8(6):580-584, (2008).

Chiarini et al. "Calcium-Sensing Receptor (Casr) in Human Brain's Pathophysiology: Roles in Late-Onset Alzheimer's Disease (Load)," *Curr. Pharma. Biotech.* 10(3):317-326, (2009).

Choo-Smith et al. "The Interaction Between Alzheimer Amyloid Beta (1-40) Peptide and Ganglioside Gmi-Containing Membranes," *FEBS Lett.* 402:95-98, (1997).

Chothia et al. "Canonical Structures for the Hypervariable Regions of Immunoglobulins," *J. Mol. Biol.* 196:901-917, (1987).

Chothia et al. "Conformations of Immunoglobulin Hypervariable Regions," *Nature* 342:877-883, (1989).

Chothia et al. "Structural Repertoire of the Human VH Segments," *J. Mol. Biol.* 227:799-817, (1992).

Chrisey et al. "Covalent Attachment of Synthetic DNA to Self-Assembled Monolayer Films," *Nucl. Acids. Res.* 24(15):3031-3039, (1996).

Christensen, D.D., "Changing the Course of Alzheimer's Disease: Anti-Amyloid Disease-Modifying Treatments on the Horizon," *Primary Care Companion J. Clin. Psych.* 9(1):32-41, (2007).

Chromy et al. "Oligomer/Conformation-Dependent Abeta Antibodies," *Abstracts of the Annual Meeting of the Society for Neuroscience* 26(1-2):4, (2000).

Chromy et al. "Self-Assembly of A Beta 1-42 Into Globular Neurotoxins," *Biochem.* 42(17):12749-12760, (2003).

Chromy et al. "Stability of Small Oligomers of Abetal-42( Addls)," *Society for Neuroscience Abstracts Abstract No. 252129, 29th Annual Meeting of the Society for Neuroscience*, Miami Beach, FL, (Oct. 23-28, 1999).

Chung et al. "Degradation of Beta-Amyloid Peptide by Microglia," *Society for Neuroscience Abstracts 26 Abstract No. 858.10, 30th Annual Meeting of the Society of Neuroscience*, New Orleans, LA, (Nov. 4-9, 2000).

Ciccotosto et al. "Methionine Oxidation: Implications for the Mechanism of Toxicity of the Beta-Amyloid Peptide From Alzheimer's Disease," *Lett. Peptide Sci.* 10(5-6):413-417, (2003).

Citron, M. "Alzheimer's Disease: Strategies for Disease Modification," *Nature Reviews Drug Discovery* 9:387-398, (2010).

Clackson et al. "Making Antibody Fragments Using Phage Display Libraries," *Nature* 352(6336):624-628, (1991).

Clark, M.S. *Plant Molecular Biology—A Laboratory Manual*, Table of Contents, (1997).

Cleary et al. "Cognitive Effects of Oligomeric and Fibril Abeta in Rats," *Soc. for Neuroscience Abstract Viewer and Itinerary Planner Abstract No. 882.2, 32nd Annual meeting of the Society for Neuroscience*, Orlando, FL, (Nov. 2-7, 2002).

Cleek et al. "Biodegradable Polymeric Carriers for a Bfgf Antibody for Cardiovascular Application," *Proc. Intl. Symp. Control. Re. Bioact. Mater.* 24:853-854, (1997).

Co et al. "Genetically Engineered Deglycosylation of the Variable Domain Increases the Affinity of an Anti-Cd33 Monoclonal Antibody," *Molec. Immunol.* 30(15):1361-1367, (1993).

Cole et al. "Alzheimer's Amyloid Story Finds Its Star," *Trends Mol. Med.* 12(9):395-396, (2006).

Cole et al. "Cat and Mouse," *Neuron* 51(6):671-672, (2006).

(56) References Cited

OTHER PUBLICATIONS

Cole et al. "Docosahexaenoic Acid Protecs From Amyloid and Dendritic Pathology in an Alzheimer's Disease Mouse Model," *Nutrition and Health* 18(3):249-259, (2006).

Cole et al. "Human IgG2 Variants of Chimmeric Anti-CD3 Are Nonmitogenic to T Cells," *J. Immunol.* 159(7):3613-3621, (1997).

Coleman, P.M. "Effects of Amino Acid Sequence Changes on Antibody-Antigen Interactions," *Research in Immunol.* 145:33-36, (1994).

Colombo et al. "CE Can Identify Small Molecules That Selectively Target Soluble Oligomers of Amyloid Beta Protein and Display Antifibrillogenic Activity," *Electrophoresis* 30(8):1418-1429, (2009).

Costantini et al. "The Expression of P75 Neurotrophin Receptor Protects Against the Neurotoxicity of Soluble Oligomers of Beta-Amyloid," *Exp. Cell Res.* 311(1):126-134, (2005).

Craft et al. "Enhanced Susceptibility of S-1 OOB Transgenic Mice to Neuroinflammation and Neuronal Dysfunction Induced by Intracerebroventricular Infusion of Human Beta-Amyloid," *Glia* 51(3):209-216, (2005).

Crouch et al. "Soluble Oligomeric Amyloid Beta 1-42 Specifically Inhibits Cytochrome C Oxidase of Human Mitochondria," *Mitochondrial Medicine* (2004) Pittsburg, PA, Mitochondrion pp. 471-472, (Aug. 4-7, 2004).

Crouse et al. "Oligomeric Amyloid-Beta(L-42) Induces THP-1 Human Monocyte Adhesion and Maturation," *Brain Res.* 1254:109-119, (2009).

Dahlgren et al. "Oligomeric and Fibrillar Species of Amyloid-Beta Peptides Differentially Affect Neuronal Viability," *J. Biol. Chem.* 277(35):32046-32053, (2002).

Das et al. "Interface Peptide of Alzheimer's Amyloid Beta: Application in Purification," *Biochem. Biophys. Res. Commun.* 362(2):538-542, (2007).

Dasilva et al. "Reduced Oligomeric and Vascular Amyloid-Beta Following Immunization of Tgcrnd8 Mice With an Alzheimer's DNA Vaccine," *Vaccine* pp. 27136-1376, (2009).

Database EMBL, "Mouse immunoglobulin rearranged kappa-chain V-region VI05 gene from, C.AL20-TEPC-105 myeloma, exons 1 and 2," Database Accession No. M12183, (Jul. 16, 1988).

Database EMBL, "Mus Musculus F5.20G3 Low-Affinity Anti-Phosphorylcholine IgG Antibody mRNA, Partial Eds," Database Accession No. AF044238, (Feb. 8, 1999).

Database Geneseq., "Anti-human Fas monoclonal antibody CHI 1 light chain cDNA," retrieved from EBI Accession No. GSN:AA V66736, Database Accession No. AA V66736, (Jan. 18, 1999).

Database Geneseq., "Mouse DNA encoding antibody 3D8 heavy chain variable region," Database Accession No. ABX16569, (Apr. 22, 2003).

Database Geneseq., "Mouse monoclonal antibody 4785 heavy chain SEQ ID 38", retrieved from EBI Accession No. GSP:ADX39137, Database Accession No. ADX39137, (2005).

Database Geneseq., Humanized monoclonal antibody H74785-2 heavy chain, retrieved from EBI accession No. GSP:ADX39139, Database Accession No. ADX39139, (2005).

Database Geneseq., "Humanized monoclonal antibody Hu4785-2 partial protein," retrieved from EBI Accession No. GSP:ADX39104 Database Accession No. ADX39104, (2005).

Database Geneseq., "Humanized monoclonal antibody Hu4785-2 VH region," retrieved from EBI accession No. GSP:ADX39143 Database Accession No. ADX39143, (2005).

Database Geneseq., "Mouse monoclonal antibody 4785 heavy chain SEQ ID 1," retrieved from EBI Accession No. GSP:ADX39100 Database Accession No. ADX39100, (2005).

Database NCBI Protein, dated Apr. 11, 1996, Accession No. AAA96779.

Database NCBI Protein, dated Mar. 23, 2002, Accession No. AAA92933.

Database NCBI Protein, dated Mar. 23, 2002, Accession No. AAL92941.

Database NCBI Protein, dated Aug. 30, 1993, Accession No. AAA38584.

David et al. "A Significant Reduction in the Incidence of Collagen Induced Arthritis in Mice Treated With Anti-TCRV-Beta Antibodies," *J. Cell Biochem.* p. 179, (1991).

Dealmeida et al. "Transgenic Expression of Two Marker Genes Under the Control of an *Arabidopsis* RBCS Promoter: Sequences Encoding the Rubisco Transit Peptide Increase Expression Levels," *Mol Gen. Genet.* 218:78-86, (1989).

De Felice et al. "Alzheimer's Disease-Type Neuronal Tau Hyperphosphorylation Induced by Abeta Oligomers," *Neurobiol. Aging* 29(9):1334-1347, (2008).

De Giorgi et al. "Induction of Foetal Lethality in AKR Offspring After Repeated Inoculations Into AKR Females of Anti-TCR/V Beta 6 Monoclonal Antibody," *Res. Immunol.* 144(4):245-255, (1993).

De Giorgi et al., "Murine Hybridomas Secreting Monoclonal Antibodies Reacting With Misa Antigens," *Exp. Clin. Immunogenet.* 10(4):219-223, (1993).

De Pascalis et al."Grafting of 'Abbreviated' Complementarity-Determining Regions Containing Specificity Determining Residues Essential for Ligand Contact to Engineer a Less Immunogenic Humanized Monoclonal Antibody," *J. Immunol.* 169:3076-3084, (2002).

De Mattos et al. "Peripheral Anti-Abeta Antibody Alters CNS and Plasma Abeta Clearance and Decreases Brain Abeta Burden in a Mouse Model of Alzheimer's Disease," *Proc. Natl. Acad. Sci. USA* 98(15):8850-8855, (2001).

De Mattos et al. "P4-358 In Vitro and In Vivo Characterization of Beta-Amyloid Antibodies Binding to Cerebral Amyloid Angiopathy (CAA) and the Selective Exacerbation of CAA-Associated Microhemorrhage" *Neurobiol Aging* 25(S2), S577 (2004).

Demeester et al. "Comparison of the Aggregation Properties, Secondary Structure and Apoptotic Effects of Wild-Type, Flemish and Dutch N-Terminally Truncated Amyloid Beta Peptides," *Euro. J. Neurosci.* 13(11):2015-2024, (2001).

Demuro et al., "Calcium Dysregulation and Membrane Disruption as a Ubiquitous Neurotoxic Mechanism of Soluble Amyloid Oligomers," *J. Biol. Chem.* 280(17):17294-17300, (2005).

Denkewalter et al. "Fortschritte Der Arzneimittelforschung Progress in Drug Research Progres Des Recheerches Pharmaceutiques," 10:224-285, (1996).

Denkewalter et al. *Progress in Drug Research* Vo. 10 23 pages, (1966).

Dewachter et al. "Neuronal Deficiency of Presenillin 1 Inhibits Amyloid Plaque Formation and Corrects Hippocampal Long-Term Potentiation But Not a Cognitive Defect of Amyloid Precursor Protein [V7171] Transgeneic Mice," *Journal of Neuroscience* 22:3445-3453, (2002).

Dickson et al. "Correlations of Synaptic and Pathological Markers With Cognition of the Elderly," *Neurobiol. Aging* 16(3):285-304, (1995).

Dillen et al. "A Two Decade Contribution of Molecular Cell Biology to the Centennial of Alzheimer's Disease: Are We Progressing Toward Therapy?" *Int. Rev. Cytol.* 254:215-300, (2006).

Ding et al. "Targeting Age-Related Macular Degeneration With Alzheimer's Disease Based Immunotherapies: Antiamyloid-Beta Antibody Attenuates Pathologies in an Age-Related Macular Degeneration Mouse Model," *Vision Research, Pergamon Press, Oxford, GB* 48(3):339-345, (2007).

Dingledine et al. *Brain slices, Plenum Press Table of Contents*, (1984).

Dodel et al. "Naturally Occurring Autoantibodies Against Beta-Amyloid: Investigating Their Role in Transgenic Animal and In Vitro Models of Alzheimer's Disease," *J Neurosci.* 31(15):5847-5854, (2011).

Donnet et al. "Plasma Treatment Effect on the Surface Energy of Carbon and Carbon Fibers," *Carbon* 24(6):757-770, (1986).

Dorronsoro et al. "Peripheral and Dual Binding Site Inhibitors of Acetylcholinesterase as Neurodegenerative Disease-Modifying Agents," *Exp. Opin. Ther. Pat.* 13(11):1725-1732, (2003).

Du et al. "Reduced Levels of Amyloid Beta-Peptide Antibody in Alzheimer Disease," *Neurology* 57:801-805, (2001).

Dufner et al. "Harnessing Phage and Ribosome Display for Antibody Optimisation," *Trends Biotech.* 24(1 1):523-529, (2006).

(56) References Cited

OTHER PUBLICATIONS

During et al. "Controlled Release of Dopamine From a Polymeric Brain Implant: In Vivo Characterization," *Ann. Neurol.* 25:351-356, (1989).
Durocher et al. "High-Level and High-Throughput Recombinant Protein Production by Transient Transfection of Suspension-Growing Human 293-Ebnal Cells," *Nucl. Acid. Res.* 30(2):e9-11, (2002).
Eckenhoff et al. "Anesthetics and Neurodegenerative Disorders: A Molecular Basis for Concern?" *Anesthesiology Abstracts of Scientific Papers Annual Meeting, 2003, Abstract No. A-848, 2003 Annual Meeting of the American Society of Anesthesiologists*, San Francisco, CA, (Oct. 11-15, 2003).
Eckert et al. "Oligomeric and Fibrillar Species Ofbeta-Amyloid (A Beta 42) Both Impair Mitochondrial Function in P301L Tau Transgenic Mice," *J. Mol. Med.* 86(11):1255-67, (2008).
Eisenberg et al. "Analysis of Membrane and Surface Protein Sequences With the Hydrophobic Moment Plot," *J. Mol. Biol.* 179(1):125-142, (1984).
Englund et al. "Oligomerization Partially Explains the Lowering of A Beta 42 in Alzheimer's Disease Cerebrospinal Fluid," *Neurodegenerative Dis.* 6:139-147, (2009).
Eren et al. "Human Monoclonal Antibodies Specific to Hepatitis B Virus Generated in a Human/Mouse Radiation Chimera: The Trimera System," *Immunol.* 93:154-161, (1998).
Esteras-Chopo et al., "New Strategy for the Generation of Specific D-Peptide Amyloid Inhibitors," *J. Mol. Biol.* 377:1372-1381, (2008).
Evans et al. "Design of a Nonpeptidal Ligands for a Peptide Receptor: Cholecystokinin Antagonists," *J. Med. Chem.* 30:1229, (1987).
Evans et al. "Heat Shock Proteins 70 and 90 Inhibit Early Stages of Amyloid Beta-(1-42) Aggregation In Vitro," *J. Biol. Chem.* 281:33182-33191, (2006).
Evans et al. "Abeta(1-42) Reduces Synapse Number and Inhibits Neurite Outgrowth in Primary Cortical and Hippocampal Neurons: A Quantitative Analysis," *J. Neurosci. Methods* 175(1):96-103, (2008).
Evin, G., "Gamma-Secretase Modulators: Hopes and Setbacks for the Future of Alzheimer's Treatment," *Expert Rev. Neurother.* 8(11):1611-1613, (2008).
Fauchere, "Elements for the Rational Design of Peptide Drugs," *Adv. Drug Res.* 15:29-69, (1986).
Feld et al. "Effect on Memory of Acute Administration of Naturally Secreted Fibrils and Synthetic Amyloid-Beta Peptides in an Invertebrate Model," *Neurobiol. Learn. Mem.* 89(4):407-418, (2008).
Ferrao-Gonzales et al. "Controlling Beta-Amyloid Oligomerization by the Use of Naphthalene Sulfonates: Trapping Low Molecular Weight Oligomeric Species," *J. Biol. Chem.* 280(41):34747-34754, (2005).
Fishwild et al. "High-Avidity Human IgGx Monoclonal Antibodies From a Novel Strain of Minilocus Transgenic Mice," *Nature Biotech.* 14:845-851, (1996).
Flink et al., "Ca2+ Channels as Targets Ofneurolgoical Disease: Lambert-Eaton Syndrome and Other Ca2+ Channelopathies," *J. Bioeng. Biomembr.* 35(6):697-718, (2003).
Foote et al. "Antibody Framework Residues Affecting the Conformation of the Hypervariable Loops," *J. Mol. Biol.* 224:487-499, (1992).
Forsell et al. "Amyloid Precursor Protein Mutation at Codon 713 (Ala→4 Val) Does Not Cause Schizophrenia: Non-Pathogenic Variant Found at Codon 705 (Silent)," *Neurosci. Lett.* 184:90-93, (1995).
Fradinger et al. "C-Terminal Peptides Coassemble Into Abeta42 Oligomers and Protect Neurons Against Abeta42-Induced Neurotoxicity," *Proc. Natl. Acad. Sci. USA* 105(37):14175-14180, (2008).
Frenkel et al. "Modulation of Alzheimer's Beta-Amyloid Neurotoxicity by Site-Directed Single-Chain Antibody," *J. Neuroimmunol.* 106(1-2):23-31, (2000).

Fuchs et al. "Targeting Recombinant Antibodies to the Surface of *Escherichia coli*: Fusion to a Peptidoglycan Associated Lipoprotein," *Bio Tech.* 9:1369-1372, (1991).
Fujimoro et al. "Production and Characterization of Monoclonal Antibodies Specific to Multi-Ubiquitin Chains of Polyubiquitinatedproteins," *FEBS* 349:173-180, (1994).
Fujimoro et al. "Production of Antipolyubiquitin Monoclonal Antibodies and Their Use for Characterization and Isolation of Polyubiquitinated Proteins," *Meth. Enzymol.* 399:75-86, (2005).
Fukuchi et al. "Amelioration of Amyloid Load by Anti-Abeta Single-Chain Antibody in Alzheimer Mouse Model," *Biochem. Biophys. Res. Commun.* 344(1):79-86, (2006).
Funke et al. "Detection of Amyloid-Beta Aggregates in Body Fluids: A Suitable Method for Early Diagnosis of Alzheimer's Disease?" *Current Alzheimer's Research* 6(3):285-289, (2009).
Galfre et al. "Antibodies to Major Histocompatibility Antigens Produced by Hybrid Cell Lines," *Nature* 266(5602):550-552, (1977).
Gallo et al. "The Human Immunoglobulin Loci Introduced Into Mice: V(D) and J Gene Segment Usage Similar to That of Adult Humans," *Eur. J. Immunol.* 30:534-540, (2000).
Garrard et al. "FAB Assembly and Enrichment in a Monovalent Phage Display System," *Bio Tech.* 9(12):1373-1377, (Dec. 1991).
Garzon et al. "Oligomeric Amyloid Decreases Basal Levels of Brain-Derived Neurotrophic Factor (BDNF) MRNA Via Specific Downregulation of BDNF Transcripts IV and Vin Differentiated Human Neuroblastoma Cells," *J. Neurosci.* 27(10):2628-2635, (2007).
Gavilondo et al. "Antibody engineering at the millennium," *Bio Techniques* 29:128-145, (2002).
Gefter et al. "A Simple Method for Polyethylene Glycol-Promoted Hybridization of Mouse Myeloma Cells," *Somatic Cell Genetics* 3(2):231-236, (1997).
Gellermann et al. "Abeta-Globulomers Are Formed Independently of the Fibril Pathway," *Neurobiol. of Dis.* 30(2):212-220, (2008).
Gennaro A.R., ed., Remington: The Science and Practice of Pharmacy, 19th Edition, Mack Publishing, Table of Contents, (1995).
Gervais et al. "Targeting Soluble Abeta Peptide With Tramiprosate for the Treatment of Brain Amyloidosis," *Neurobiol. Aging* 28(4):537-547, (2007).
Ghiso et al., "Systemic Catabolism of Alzheimer's Abeta40 and Abeta42," *J. Biol. Chem.* 279:45897-45908, (2004).
Ghosal et al. "Alzheimer's Disease-Like Pathological Features in Transgenic Mice Expressing the App Intracellular Domain," *Proc. Natl. Acad. Sci. USA* 106(43):18367-18372, (2009).
Giacobini et al. "One Hundred Years After the Discovery of Alzheimer's Disease. A Turning Point for Therapy? The Multifaceted Aspects of Alzheimer's Disease: From Social to Molecular Problems," *J. Alzheimer's Disease* 12(1):37-52, (2007).
Gibbs et al. "Rescue of Abeta SUB 1-42-Induced Memory Impairment in Day-Old Chick by Facilitation of Astrocytic Oxidative Metabolism: Implications for Alzheimer's Disease," *J. Neurochem.* 109 Suppl. 1:230-236, (2009).
Giege et al. "An Introduction to the Crystallogenesis of Biological Macromolecules," in *Crystallization of Nucleic Acids & Proteins, a Practical Approach*, 2nd Edition: 1-16, (1999).
Giliberto et al. "Mutant Presenilin 1 Increases the Expression and Activity of BACE1," *J. Biol. Chem.* 284(14):9027-9038, (2009).
Gillies et al. "High-Level Expression of Chimeric Antibodies Using Adapted Cdna Variable Region Cassettes," *J. Immunol. Meth.* 125:191-202, (1989).
Giuffrida et al. "A Beta(25-35) and Its C- and/or N-Blocked Derivatives: Copper Driven Structural Features and Neurotoxicity," *J. Neursci. Res.* 85:623-633, (2007).
Giuffrida et al. "Beta-Amyloid Monomers Are Neuroprotective," *J. Neurosci.* 29(34):10582-10587, (2009).
Goeddel, D. "Systems for Heterologous Gene Expression," *Meth. In Enzymol.* 185:3-7, (1990).
Goldspiel et al. "Human Gene Therapy," *Clin. Pharm.* 12:488-505, (1993).
Gong et al. "Abeta-Derived Diffusible Ligands in Alzheimer's Disease Brain as Therapeutic Antibody Targets," *Abstracts of the Annual Meeting of the Society of Neuroscience* 1 page, (2002).

(56) References Cited

OTHER PUBLICATIONS

Gong, Y. "Alzheimer's Disease-Affected Brain: Presence of Oligomeric a Ligands (Addls) Suggests a Molecular Basis for Reversible Memory Loss," *Proc. Natl. Acad. Sci. USA* 100(18):10417-10422, (2003).
Gonzalo-Ruiz et al. "Oligomers of Beta-Amyloid (1-42) Peptide Induce Co-Localization of AB and TAU Proteins Associated With Calpain Activity," *J. Neurochem.* 110:57-58, (2009).
Goodson, J.M. "Dental Applications" *Medical Applications of Controlled Release*, vol. II, Chapter 6 115-138, (1984).
Gowing et al. "Chemical Characterization of a Beta 17-42 Peptide, A Component of Diffuse Amyloid Deposits of Alzheimer Disease," *J. Biol. Chem.* 269:10987-10988, (1994).
Grabarek et al. "Zero-Length Crosslinking Procedure With the Use of Active Esters," *Anal. Biochem.* 185(1):131-135, (1990).
Grabowski et al. "Novel Amyloid Precursor Protein Mutation in an Iowa Family With Dementia and Severe Cerebral Amyloid Angiopathy," *Ann. Neurol.* 49(6):697-705, (2001).
Grace et al. "Abeta Induces Oxidative-Degradative Stress Through NADPH Oxidase and Phopholipase A2," *J. Neurochem. 110222, 22nd Biennial Meeting of the International Society of Neurochemistry, South Korea* (Aug. 23-29, 2009).
Gram et al. "In Vitro Selection and Affinity Maturation of Antibodies From a Naïve Combinatorial Immunoglobulin Library," *Proc. Natl. Acad. Sci. USA* 89:3576-3580, (1992).
Grange et al. "FAST DB: A Website Resource for the Study of the Expression Regulation of Human Gene Products," *Nucl. Acids Res.* 33(13):4276-4284, (2005).
Green et al. "Antigen-Specific Human Monoclonal Antibodies From Mice Engineered With Human Ig Heavy and Light Chain YACs," *Nature Genetics* 7(1):12-21, (1994).
Green et al. "Regulation of B Cell Development by Variable Gene Complexity in Mice Reconstituted With Human Immunoglobulin Yeast Artificial Chromosomes," *J. Exp. Med.* 188(3):483-495, (1998).
Green, L.L. "Antibody Engineering Via Genetic Engineering of the Mouse: Xenomouse Strains Are a Vehicle for the Facile Generation of Therapeutic Human Monoclonal Antibodies," *J. Immunol. Meth.* 231:11-23, (1999).
Griffiths et al. "Human Anti-Self Antibodies With High Specificity From Phage Display Libraries," *The EMBO Journal* 12(2):725-734, (1993).
Guo et al. "APOE Down Regulates Pro-Inflammatory Responses Induced by Oligomeric Abeta in Activated Glia," *Soc. For Neurosci. Abstract Viewer and Itinerary Planner, Abstract No. 883.12, 32nd Annual meeting of the Society for Neuroscience, Orlando, FL* (Nov. 27, 2002).
Guo et al. "Targeting Amyloid-Beta in Glaucoma Treatment," *Proc. Natl. Acad. Sci. USA* 104(33):13444-13449, (2007).
Ha et al. "Ex Situ Atomic Force Microscopy Analysis of Beta-Amyloid Self-Assembly and Deposition on a Synthetic Template," *Langmuir* 22:6977-6985, (2006).
Ha et al. "Metal Ions Differntially Influence the Aggregation and Deposition of Alzheimer's Beta-Amyloid on a Solid Template," *Biochem.* 46(20):6118-6125, (2007).
Ha et al. "Development of Herbal Medicine for Alzheimer's Disease From RHEI Rhizoma," *J. Neurochem.* 110114, (2009).
Haass et al. "Soluble Protein Oligomers in Neurodegeneration: Lessons From the Alzheimer's Amyloid Betapeptide," *Nat. Rev. Mol. Cell Biol.* 8(2):101-112, (2007).
Hachiya et al. "Oligomeric Aip2p/Dld2p Modifies the Protein Conformation of Both Properly Folded and Misfolded Substrates In Vitro," *Biochem. Biophys. Res. Comm.* 323(1):339-344, (2004).
Hagemeyer et al. "Single-Chain Antibodies as Diagnostic Tools and Therapeutic Agents," *Thromb. Haemost.* 101:1012-1019, (2009).
Halladay et al. "Synthesis of Hydroxyethelene and Ketomethylene Dipeptide Isosteres," *Tetrahedron Lett.* 24:4401-4404, (1983).
Hann, M.M., "On the Double Bond Isostere of the Peptide Bond: Preparation of an Enkephalin Analogue," *J. Chem. Soc. Perkin Transactions* 1:307-314, (1982).

Harding et al. "Class Switching in Human Immunoglobulin Transgenic Mice," *Ann. N.Y. Acad. Sci.* 764:536-546 ,(1995).
Hardy et al., "The Amyloid Hypothesis of Alzheimer's Disease: Progress and Problems on the Road to Therapeutics," *Science* 297:353-356, (2002).
Harlow and Lane Antibodies: A Laboratory Manual, *New York, Gold Spring Harbor Press* (1990).
Harris-White et al., "Effects Oflow Dose, Low MW Soluble Amyloid Oligomers on Spatial Memory Performance," *Society for Neurosci. Abstr. Viewer and Itin. Plann. Abstract No. 240.11, 33rd Annual Meeting of the Society of Neuroscience, New Orleans* (Nov. 8-12, 2003).
Hartley et al. "Transglutaminase Induces Protofibril-Like Amyloid Beta-Protein Assemblies That Are Protease-Resistant and Inhibit Long-Term Potentiation," *J. Biol. Chem.* 283(24):16790-16800, (2008).
Hashida et al. "More Useful Maleimide Compounds for the Conjugation of Fab to Horseradish Peroxidase Through Thiol Groups in the Hinge," *J. Appl. Biochem.* 6:56-63, (1984).
Hashimoto et al. "Role of Protein Aggregation in Mitochondrial Dysfunction and Neurodegeneration in Alzheimer's and Parkinson's Disease," *Neuromol. Med.* 4(1-2):21-36, (2003).
Hawkins, R.E., "Selection of Phage Antibodies by Binding Affinity-Imicking Affinity Maturation," *J. Mol. Biol.* 226:889-896, (1992).
Hay et al. "Bacteriophage Cloning and *Escherichia coli* Expression of a Human Igm Fab," *Hum. Antibod. Hybridomas* 3:81-85, (1992).
Hayes et al. "Production of Beta-Amyloid by Primary Human Foetal Mixed Brain Cell Cultures and Its Modulation by Exogeneous Soluble Beta-Amyloid," *Neurosci.* 113(3):641-646, (2002).
Head et al. "A Two-Year Study With Fibrillar Beta-Amyloid (Abeta) Immunization in Aged Canines: Effects on Cognitive Function and Brain Abeta," *J. Neurosci.* 28(14):3555-3566, (2008).
Head et al. "The Effects of Immunization With Fibrillar or Oligomeric Abeta in the Brain and CSF of Aged Canines: A Pilot Study," *Society for Neuroscience Abstract Viewer and Itinerary Planner Abstract No. 525.24, 33rd Annual Meeting of the Society of Neuroscience, New Orleans, LA,* (Nov. 8-12, 2003).
Heard et al. "Two Neutralizing Human Anti-Rsv Antibodies: Cloning, Expression, and Characterization," *Molec. Med.* 5:35-45, (1999).
Heinitz et al. "Toxicity Mediated by Soluble Oligomers of Beta-Amyloid (L-42) on Cholinergic SN56.135.G4 Cells," *J. Neurochem.* 98(6):1930-1945, (2006).
Helisalmi et al. "Screening for Amyloid Beta Precursor Protein Codon 665, 670/671 and 717 Mutations in Finnish Patients With Alzheimer's Disease," *Neurosci. Lett.* 205:68-70, (1996).
Herz et al. "The Humanized (HU-PBMC) SCID Mouse as an In Vivo Model for Human IgE Production and Allergic Inflammation of the Skin," *Int. Arch Allergy Immunol.* 113(1-3):150-152, (1997).
Hess et al. "Cooperation of Glycolytic Enzymes," *J. Adv. Enzyme Reg.* 7:149-167, (1968).
Hicke, "Protein Regulation by Monoubiquitin," *Nat. Rev.* 2:196-201, (2001).
Hieter et al. "Evolution of Human Immunoglobulin kJ Region Genes," *J. Biol. Chem.* 257(3): 1516-1522, (1982).
Higgins et al. "Fast and Sensitive Multiple Sequence Alignments on a Microcomputer," *CABIOS Comm.* 5(2):151-153, (1989).
Higuchi, R., "Using PCR to Engineer DNA," *PCR Technol: Prine. & Appl. for DNA Amplification* pp. 61-70, (1989).
Hilbich et al. "Aggregation and Secondary Structure of Synthetic Amyloid BetaA4 Peptides of Alzheimer's Disease," *J. Mol. Biol.* 218:149-163, (1991).
Hillen et al. "Generation and Therapeutic Efficacy of Highly Oligomer-Specific Beta-Amyloid Antibodies," *J. Neurosci.* 30(31):10369-10379, (2010).
Hirko et al. "Peripheral Transgene Expression of Plasma Gelsolin Reduces Amyloid in Transgenic Mouse Models of Alzheimer's Disease," *Mol. Ther.* 15(9):1623-9, (2007).
Hock et al. "Clinical Observations with AN-1792 Using TAPIR Analyses," *Neurodegenerative Dis.* 2(5):273-276 (2006).
Holliger et al., "'Diabodies' Small Bivalent and Bispecific Antibody Fragments, *Proc. Natl. Acad. Sci. USA* 90:6444-6448, (1993).

(56) References Cited

OTHER PUBLICATIONS

Holm et al., "Functional Mapping and Single Chain Construction of the Anti-Cytokeratin 8 Monoclonal Antibody TS1," *Mol. Immunol.* 44:1075-1084, (2007).

Hong et al., "Combining the Rapid MTT Formazan Exocytosis Assay and the MC65 Protection Assay LED to the Discovery of Carbozole Analogs as Small Molecule Inhibitors of Abeta Oligomer-Induced Cytotoxicity," *Brain Res.* 1130(1):223-234, (2007).

Hong et al. "Inhibition of Alzheimer's Amyloid Toxicity With a Tricyclic Pyrone Molecule In Vitro and In Vivo," *J. Neurochem.* 108(4):1097-1108, (2009).

Hoogenboom et al., "Multi-Subunit Proteins on the Surface of Silamentous Phage: Methodologies for Displaying Antibody (FAB) Heavy and Light Chains," *Nucl. Acids Res.* 19(15):4133-4137, (1991).

Hoogenboom et al. "Natural and Designer Binding Sites Made by Phage Display Technology," *Immunol. Today* 21(8):371-378, (2000).

Hoogenboom, H.R. "Designing and Optimizing Library Selection Strategies for Generating High-Affinity Antibodies," *Tibtech* 15:62-70, (1997).

Hoozemans et al. "Always Around, Never the Same: Pathways of Amyloid Beta Induced Neurodegeneration Throughout the Pathogenic Cascade of Alzheimer's Disease," *Curr. Med. Chem.* 13(22):2599-2605, (2006).

Hossain et al. "Mechanism of Docosahexaenoic Acid-Induced Inhibition of in Vitro Abetal-42 Fibrillation and Abetal-42-Induced Toxicity in SH-S5Y5 Cells," *J. Neurochem.* 111(2):568-579, (2009).

Howard III et al. "Intracerebral Drug Delivery in Rats With Lesion-Induced Memory Deficits," *J. Neurosurg.* 71:105-112, (1989).

Howlett et al. "The Pathology of APP Transgenic Mice: A Model of Alzheimer's Disease or Simply Overexpression of APP?" *Histol. Histopathol.* 24(1):83-100, (2009).

Hoyer et al. "Stabilization of a Beta-Hairpin in Monomeric Alzheimer's Amyloid-Beta Peptide Inhibits Amyloid Formation," *Proc. Natl. Acad. Sci. USA* 105(13):5099-5104, (2008).

Hruby, V.J. "Conformational Restrictions of Biologically Active Peptides via Amino Acid Side Chain Groups," *Life Sci.* 31:189-199, (1982).

Hsiao et al. "Correlative Memory Deficits, AP Elevation, and Amyloid Plaques in Transgenic Mice," *Science* 274(5284): 99-102 (1996).

Huang et al. "Isoproterenol Potentiates Synaptic Transmission Primarily by Enhancing Presynaptic Calcium Influx via P-and/or Q-Type Calcium Channels in the Rat Amygdala," *J. Neurosci.* 16(3):1026-1033, (1996).

Huang et al. "Selective Enhancement of P-Type Calcium Currents by Isoproterenol in the Rat Amygdata," *J. Neurosci.* 18(6):2276-2282, (1998).

Huang et al. "Metal-Dependence of Abeta Oligomerization," *Soc. For Neurosci. Abstract Viewer and Itinerary Planner Abstract No. 19.1, 32nd Annual meeting of the Society for Neuroscience*, Orlando, FL, (Nov. 2-7, 2002).

Huse et al. "Generation of a Large Combinatorial Library of the Immunoglobulin Repertoire in Phage Lambda," *Science* 246:1275-1281, (1989).

Huston et al. "Protein Engineering of Antibody Binding Sites: Recovery of Specific Activity in All Anti-Digoxin Single-Chain Fv Analogue Produced in *Escherichia coli*," *PNAS* 85(16):5879-5883, (1988).

Huston et al. "Protein Engineering of Single-Chain Fv Analogs and Fusion Proteins," *Meth. In Enzymol.* 203:46-88, (1991).

Hutchins et al. "Human Immune Response to a Peptide Mimic of Neisseria Meningitis Serogroup C in Hu-PBMC-SCID Mice," *Hybridoma* 18(2):121-129, (1999).

Hyman et al. "Autoantibodies to Amyloid-Beta and Alzheimer's Disease," *Ann. Neurol.* 49: 808-810, (2001).

Iijima et al. "A Beta 42 Mutants With Different Aggregation Profiles Induce Distinct Pathologies in *Drosophila*," *PLoS One* 3 Article No. El 703, (2008).

Ilan et al. "The Hepatitis B Virus-Trimera Mouse: A Model for Human HBV Infection and Evaluation of Anti-HBV Therapeutic Agents," *Hepatology* 29:553-562, (1999).

Ingelbrecht et al. "Different 3' End Regions Strongly Influence the Level of Gene Expression in Plant Cells," *The Plant Cell* 1:671-780, (1989).

Jang et al. "The Structural Basis for DNA Binding by an Anti-DNA Autoantibody," *Molec. Immunol.* 35:1207-1217, (1998).

Janssen et al. "Early Onset Familial Alzheimer's Disease: Mutation Frequency in 31 Families," *Neurology* 60(2):235-239, (2003).

Jefferis, R. "Glycosylation of Recombinant Antibody Therapeutics," *Biotechnol. Prog.* 21:11-16, (2005).

Jennings-White et al. "Synthesis of Ketomethylene Analogogs of Dipeptides," *Tetrahedr. Lett.* 23(25):2533-2534, (1982).

Jensen et al. "Lifelong Immunization With Human Beta-Amyloid (1-42) Protects Alzheimer's Transgenic Mice Against Cognitive Impairment Throughout Aging," *Neurosci.* 130:667-684, (2005).

Jeon et al. "Impaired Long-Term Memory and Long-Term Potentiation in N-Type Ca2+ Channel-Deficient Mice," *Genes, Brain Behavior* 6:375-388, (2007).

Jiang et al. "Recent Progress of Synthetic Studies to Peptide and Peptidomimetic Cyclization," *Curr. Org. Chem.* 12(17):1502-1542, (2008).

Joerchel et al. "Oligomeric Beta-Amyloid(L-42) Induces the Expression of Alzheimer Disease-Relevant Proteins in Cholinergic SN56.135.G4 Cells as Revealed by Proteomic Analysis," *Int. J. Developm. Neurosci.* 26(3-4):301-308, (2008).

Johansson et al. "Attenuated Amyloid-Beta Aggregation and Neurotoxicity Owing to Methionine Oxidation," *NeuroReport* 18(6):559-563, (2007).

Johansson et al. "Dramatic Changes in Fibrillization Rate and Oligomer/Protofibrillar Formation of Betaamyloid Peptide With Oxidized Methionine: Implications for Novel Therapeutic Approaches in Alzheimer's Disease," *Soc. for Neurosci. Abstract Viewer and Itinerary Planner Abstract No. 123.8, 32nd Annual meeting of the Society for Neuroscience*, Orlando, FL (Nov. 2-7, 2002).

Johansson et al. "Docosahexaenoic Acid Stabilizes Soluble Amyloid-Beta Protofibrils and Sustains Amyloid-Beta-Induced Neurotoxicity In Vitro," *FEBS J.* 274(14):990-1000, (2007).

Johansson et al. "Physiochemical Characterization of the Alzheimer's Disease-Related Peptides Abetal-42Arctic and Abetal-42wt," *FEBS Journal* 273(12):2618-2630, (2006).

Johnsson et al. "Comparison of Methods for Immobilization to Carboxymethyl Dextran Sensor Surfaces by Analysis of the Specific Activity of Monoclonal Antibodies," *J. Mol. Rec.* 8:125-131, (1995).

Johnsson et al. "Immobilizataion of Progeins to a Carboxymethyldextran-Modified Gold Surface for Biospecific Interaction Analysis in Surface Plasmon Resonance Sensors," *Anal. Biochem.* 198:268-277, (1991).

Joliot et al. "Antennapedia Homeobox Peptide Regulates Neural Morphogenesis," *Proc. Natl. Acad. Sci. USA* 88:1864-1868, (1991).

Jones et al. "Mutation in Codon 713 of the Beta-Amyloid Precursor Protein Gene Presenting With Schizophrenia," *Nat. Genet.* 1(4):306-309, (1992).

Jones et al. "High Level Expression of Introduced Chimaeric Genes in Regenerated Transformed Plants," *EMBO J.* 4(10):2411-2418, (1985).

Jonsson et al. "Introducing a Biosensor Based Technology for Real-Time Biospecific Interaction Analysis," *Ann. Biol. Clin.* 51:19-26, (1993).

Jonsson et al. "Real-Time Biospecific Interaction Analysis Using Surface Plasmon Resonance and a Sensor Chip Technology," *Bio Techniques* 11(5):620-627, (1991).

Jungbauer et al. "Preparation of Fluorescently-Labeled Amyloid-Beta Peptide Assemblies: the Effect of Luorophore Conjugation on Structure and Function," *J. Mol. Recogn.* 22(5):403413, (2009).

Kabat et al. "Attempts to Locate Complementarity-Determining Residues in the Variable Positions of Light and Heavy Chains," *Ann. NY Acad. Sci.* 190:382-391, (1971).

Kabat et al. "Accession No. PS91-192898, Sequences of Proteins of Immunological Interest," *5th Edition, NIH Publ. #91/3242* Table of Contents, (1991).

(56) References Cited

OTHER PUBLICATIONS

Kaiser et al. "Peptide and Protein Synthesis by Segment Synthesis-Condensation," *Science* 243:187,(1989).

Kakio et al. "Interactions of Amyloid Beta-Protein With Various Gangliosides in Raft-Like Membranes: Importance of GM1 Ganglioside-Bound Form as an Endogenous Seed for Alzheimer Amyloid," *Biochem.* 41:7385-7390, (2002).

Kamino et al. "Linkage and Mutational Analysis of Familial Alzheimer Disease Kindreds for the APP Gene Region," *Am. J. Hum. Genet.* 51(5):998-1014, (1992).

Kanemitsu et al. "Human Neprilysin Is Capable of Degrading Amyloid Beta Peptide Not Only in the Monomeric Form but Also the Pathologica Oligomeric Form," *Neursci. Lett.* 350:113-116, (2003).

Kaufman et al. "Amplification and Expression of Sequences Contrasfected With a Modular Dihydrofolate Reductase Complementary DNA Gene," *Mol. Biol.* 159:601-621, (1982).

Kawarabayashi et al. "Age-Dependent Changes in Brain, CSF, and Plasma Amyloid Beta Protein in the Tg2576 Transgenic Mouse Model of Alzheimer's Disease," *J. Neurosci.* 21(3):372-381, (2001).

Kawarabayashi et al. "Dimeric Amyloid Beta Protein Rapidly Accumulates in Lipid Rafts Followed by Apolipoprotein E and Phosphorylated Tau Accumulation in the Tg2576 Mouse Model of Alzheimer's Disease," *J. Neurosci.* 24(15):3801-3809, (2004).

Kayed et al. "Common Structure of Soluble Amyloid Oligomers Implies Common Mechanism of Pathogenesis," *Science* 300(18):486-489, (2003).

Kellermann et al. "Antibody Discovery: The Use of Transgenic Mice to Generate Human Monoclonal Antibodies for Therapeutics," *Curr. Opin. in Biotechnol.* 13:593-597, (2002).

Kenneth, R.H. *Monoclonal Antibodies: A New Dimension in Biological Analyses*, Plenum Publishing Corp. New York, New York (1980).

Kent, S.B.H. "Chemical Synthesis of Peptides and Proteins," *Ann. Rev. Biochem.* 57:957-989, (1988).

Keowkase et al. "Mechanism of CNS Drugs and Their Combinations for Alzheimer's Disease," *Central Nervous System Agents in Medicinal Chemistry* 8(4):241-248, (2008).

Kettleborough et al. "Isolation of Tumor Cell-Specific Single-Chain Fv From Immunized Mice Using Phage-Antibody Libraries and the Re-Construction of Whole Antibodies From These Antibody Fragments," *Eur. J. Immunol.* 24:952-958, (1994).

Kim et al. "Putative Therapeutic Agents for the Learning and Memory Deficits of People With Down Syndrome," *Bioorg. Med. Chem. Lett.* 16(14):3772-3776, (2006).

Kim et al. "Biological Tuning of Synthetic Tactics in Solid-Phase Synthesis: Application to Abeta(L-42)" *J. Org. Chem.* 69(22):7776-7778, (2004).

Kim et al. "Development of Conformation-Specific Antibodies for Neutralization of Beta-Amyloid Oligomers," *Abstract Neurobiol. Aging* 25(1):SI45, PI-175, (2004).

Kipriyanov et al. "Recombinant Single-Chain Fv Fragments Carrying C-Terminal Cysteine Residues: Production of Bivalent and Biotinylated Miniantibodies," *Mol. Immun.* 31(14):1047-1058, (1994).

Kipriyanov et al. "Single-Chain Antibody Streptavidin Fusions: Tetrameric Bifunctional scFv-Complexes With Biotin Binding Activity and Enhanced Affinity to Antigen," *Hum. Antibod. Hybridomas* 6(3):93-101, (1995).

Kirkitadze et al. "Identification and Characterization of Key Kinetic Intermediates in Amyloid B-Protein Fibrillogenesis," *J. Mol. Biol.* 312:1103-1119, (2001).

Kisilevsky et al. "Arresting Amyloidosis In Vivo Using Small-Molecule Anionic Sulphonates or Sulphates: Implications for Alzheimer's Disease," *Nat. Med.* 1(2):143-148, (1995).

Kisilevsky, "Anti-Amyloid Drugs Potential in the Treatment of Diseases Associated With Aging," *Drugs Aging* (1996) 8(2):75-83, (1996).

Kitamura et al. "Stress Proteins and Regulation of Microglial Amyloid-Beta Phagocytosis," *Folia Pharmacologica Japonica* 124(6):407-413, (2004).

Kitchin et al. "Cloning, Expression, and Purification of an Anti-Desipramine Single Chain Antibody in NS/O Myeloma Cells," *J. Pharm. Sci.* 84(10):1184-1189, (1995).

Klafki, H-W. et al., "Electrophoretic separation ofbeta-A4 peptides (1-40) and 1-42)," Anal. Biochem. 237:24-29, (1996).

Klein, W. "ABeta Toxicity in Alzheimers Disease; Globular Oligomers (Addls) as New Vaccine and Drug Targets," *Neurochem. Intl.* 41(5):345-352, (2002).

Klyubin et al., "Amyloid Beta-Protein (Abeta) Bearing the Arctic Mutation Is a More Potent Inhibitor of LTP Than Wild Type Abeta," *Society for Neuroscience Abstract Viewer and Itinerary Planner*, 2003Abstract No. 904.13, 33rd Annual Meeting of the Society of Neuroscience, New Orleans, LA, (Nov. 8-12, 2003).

Klyubin et al. "Amyloid Beta Protein Immunotherapy Neutralizes Abela Oligomers That Disrupt Synaptic Plasticity In Vivo," *Nature Med.* 11 (5):556-561, (2005).

Knappik et al. "Fully Synthetic Human Combinatorial Antibody Libraries (hUCAL) Based on Modular Consensus Frameworks and Cdrs Randomized With Trinucleotides," *J. Mol. Biol.* 296:57-86, (2000).

Knowles et al. "The P75 Neurotrophin Receptor Promotes Amyloid-Beta(L-42)-Induced Neuritic Dystrophy In Vitro and In Vivo," *J. Neurosci.* 29:10627-10637, (2009).

Kobayashi et al. "Tryptophan H33 Plays an Important Role in Pyrimidine (6-4) Pyrimidone Photo Product Binding by a High-Affinity Antibody," Protein Eng. 12:879-884, (1999).

Koh et al. "Amyloid-Beta-Induced Neurotoxicity Is Reduced by Inhibition of Glycogen Synthase Kinase-3," *Brain Res.* 1188:254-262, (2008).

Kohler, "Continuous Cultures of Fused Cells Secreting Antibody of Predefined Specificity," *Nature* 256:495-497,(1975).

Kokubo et al. "Oligomeric Proteins Ultrastructurally Localize to Cell Processes, Especially to Axon Terminals With Higher Density, But Not to Lipid Rafts in Tg2576 Mouse Brain," *Brain Res.* 1045(1-2):224-228, (2005).

Kontermann, *Antibody Engineering*, Springer-Verlag, Berlin, Table of Contents, (2001).

Kooistra et al. "A New Function of Human Htra2 as an Amyloid-Beta Oligomerization Inhibitor," *J. Alzheimer's Disease* 17(2):281-294, (2009).

Kortekaas et al. "Development of HVA and LVA Calcium Currents in Pyramidal CA1 Neurons in the Hippocampus of the Rat," *Dev. Brain Res.* 101(1-2):139-147, (1997).

Kranenburg et al. "Beta-Amyloid (Abeta) Cuases Detachment of Nle-115 Neuroblastoma Cells by Acting as a Scaffold for Cell-Associated Plasminogen Activity," *Mol. Cell. Neurosci.* 28(3):496-508, (2005).

Kriegler, M., *Gene Transfer and Expression—A Laboratory Manual* (1990) Table of Contents.

Kumar et al. "Molecular Cloning and Expression of the Fabs of Human Autoantibodies in *Escherichia coli*," *J. Biol. Chem.* 275:35129-35136, (2000).

Kumar et al. "Neuropathology and Therapeutic Management of Alzheimer's Disease—An Update," *Drugs of the Future* 33(5):433-446, (2008).

Kumar-Singh et al. "Dense-Core Senile Plaques in the Flemish Variant of Alzheimer's Disease Are Vasocentric," *Am. J. Pathol.* 161(2):507-520, (2002).

Kundrot et al. "Which Strategy for a Protein Crystallization Project?" *Cell. Mol. Life Sci.* 61:525-536, (2004).

Kuo et al. "Water-Soluble Abeta (N-40, N-42) Oligomers in Normal and Alzheimer Disease Brains," *J. Biol. Chem.* 271(8):4077-4081, (1996).

Kwon et al. "Synthesis, In Vitro Assay, and Molecular Modeling of New Piperidine Derivatives Having Dual Inhibitory Potency Against Acetylcholinesterase and Abeta SUB 1-42 Aggregation for Alzheimer's Disease Therapeutics," *Bioorg. Med. Chem.* 15(20):6596-6607, (2007).

Lacor et al. "Synaptic Targeting by Alzheimer's-Related Amyloid Beta Oligomers," *J. Neurosci.* 24:10191-10200, (2004).

Laemmli et al. "Cleavage of Structural Proteins During the Assembly of the Head of Bacteriophage T4," *Nature* 227:680-685, (1970).

(56) References Cited

OTHER PUBLICATIONS

Lahiri et al. "Lethal Weapon: Amyloid Beta-Peptide, Role in the Oxidative Stress and Neurodegeneration of Alzheimer's Disease," *Neurobiol Aging* 25(5):581-587, (2004).
Lam et al. "Effects of the Arctic (E22-G) Mutation on Amyloid Beta-Protein Folding: Discrete Molecular Dynamics Study," *J. Amer. Chem. Soc.* 130(51):17413-22, (2008).
Lam et al. "Microencapsulation of Recombinant Humanized Monoclonal Antibody for Local Delivery," *Proceedings Intl. Symp. Control. Rel. Bioact. Mater.* 24:759-760, (1997).
Lambert et al. "Diffusible, Nonfibrillar Ligands Derived From a Betal-42 Are Potent Central Nervous System Neurotoxins," *Proc. Natl. Acad. Sci. USA* 95:6448-6453, (1998).
Lambert et al. "Monoclonal Antibodies That Target Pathological Assemblies of A Beta," *J. Neurochem.* 100(1):23-35, (2007).
Lambert et al. "Vaccination With Soluble AB Oilgerm Generates Toxicity-Neutralizing Antibodies," *J. Neurochem.* 79(3):595-605, (2001).
Langdon et al. "Germline Sequences of VH7183 Gene Family Members in C57BL/6 Mice Demonstrate Natural Selection of Particular Sequences During Recent Evolution," *Immunogen.* 51:241-245, (2000).
Langer & Peppas, Editors, *Journal of Macromolec. Sci.* 23:61-127, (1983).
Langer et al. "Chemical and Physical Structure of Polymers as Carriers for Controlled Release of Bioactive Agents: A Review," *Journal of Macromolecular Science—Reviews in Macromolecular Chemistry & Physics*, C23(1):61-126, (1983).
Langer, R., "New Methods of Drug Delivery," *Science* 249:1527-1533, (1990).
Lanni et al., "Studies and Screening of Molecules Interacting With Beta Amyloid and Other Amyloidogenic Proteins," *Society for Neuroscience Abstract Viewer and Itinerary Planner Abstract No. 841.1, 33rd Annual Meeting of the Society of Neuroscience*, New Orleans, LA (Nov. 8-12, 2003).
Lashuel et al. "Amyloid Pores From Pathogenic Mutations," *Nature* 418(6895):291, (2002).
Lau et al. "Cholesterol and Clioquinol Modulation of A Beta(L-42) Interaction With Phospholipid Bilayers and Metals," *Biochimica et biophysica acta* 1768(12):3135-44, (2007).
Lauren et al. "Cellular Prion Protein Mediates Impairment of Synaptic Plasticity by Amyloid-Beta Oligomers," *Nature* 457(7233):1128-1132, (2009).
Lazo et al. "On the Nucleation of Amyloid Beta-Protein Monomer Folding," *Protein Sci.* 14(6):1581-15196, (2005).
Leader et al., "Antibody Responses to the Blood Group Antigen D in SCID Mice Reconstituted With Human Blood Mononuclear Cells," *Immunology* 76:229-234, (1992).
Lecanu et al. "Caprospinol: Moving From a Neuroactive Steroid to a Neurotropic Drug," *Exp. Opin. Invest. Drugs* 18(3):265-276, (2009).
Lee et al. "Insulin Rescues Amyloid Beta-Induced Impairment of Hippocampal Long-Term Potentiation," *Neurobiol. Aging* 30(3):377-387, (2009).
Lee et al. "Differential Physiologic Responses of Alpha7 Nicotinic Acetylcholine Receptors to Beta-Amyloid SUB 1-40 and Beta-Amyloid SUB 10-42," *J. Neurobiol.* 55(1):25-30, (2003).
Lee et al. "Secretion and Intracellular Generation of Truncated Abeta in Beta-Site Amyloid-Beta Precursor Protein-Cleaving Enzyme Expressing Human Neurons," *J. Biol Chem.* 278(7):4458-4466, (2003).
Lee et al. "Targeting Amyloid-Beta Peptide (Abeta) Oligomers by Passive Immunization With a Conformation-Selective Monoclonal Antibody Improves Learning and Memory in Abeta Precursor Protein (APP) Transgenic Mice," *J. Biol. Chem.* 281(7):4292-4299, (2006).
Lee et al. "The Insulin/Akt Signaling Pathway Is Targeted by Intracellular Beta-Amyloid," *Mol. Biol. Cell* 20(5):1533-1544, (2009).
Lee et al. "Artificial Proteases Toward Catalytic Drugs for Amyloid Diseases," *Pure and Applied Chem.* 81:255-262, (2009).
Lee et al. "Molecular Cloning of Agonistic and Antagonistic Monoclonal Antibodies Against Human 4-IBB," *Eur. J. Immunogenet.* 29(5):449-452, (2002).
Lemere et al. "Amyloid-Beta Immunotherapy for the Prevention and Treatment of Alzheimer Disease: Lessons From Mice, Monkeys, and Humans," *Rejuvenation Res.* 9(1):77-84, (2006).
Lemere et al. "Developing Novel Immunogens for a Safe and Effective Alzheimer's Disease Vaccine Neurotherapy: Progress in Restorative Neuroscience and Neurology," *Progress in Brain Research* 175:83-93, (2009).
Lerner, E.A. "How to Make a Hybridoma," *The Yale Journal of Biology and Medicine* 54(5):387-402, (1981).
Leveille et al. "Influence of Oligomeric Forms of the Amyloid Beta 1-42 on Neuronal Viablity," *Rev. Neurol (Paris)* 163(11)-2:4523, (2007).
Levine et al. "Alzheimer's .Beta.-Peptide Oligomer Formation at Physiologic Concentrations," *Anal. Biochem.* 335:81-90, (2004).
Levine, H, III, "4,4'-Dianilino-1,1"-Binaphthy1-5'-Disulfonate (bis-ANS) Reports on Non-Beta-Sheet Conformers of Alzheimer's Peptide Beta (1-40)," Arch Biochem. Biophys. 404: 106-115, (2002).
Levitt, M., "Molecular Dynamics of Native Protein," *J. Mol. Biol.* 168:595-620, (1983).
Levy et al. "Inhibition of Calcification of Bioprosthetic Heart Valves by Local Controlled-Release Diphosphonate," *Science* 228:190-192, (1985).
Lewis et al. "Quantification of Alzheimer Pathology in Ageing and Dementia: Age-Related Accumulation of Amyloid-Beta(42) Peptide in Vascular Dementia," *Neuropath. Appl. Neurobiol.* 32(2): 103-118, (2006).
Li et al. "SAR and Mechanistic Studies of Tetrapeptide Inhibitors of A Beta 42-Induced Neurotoxicity," *Biopolymers* 92(4):P077, (2009).
Liao et al. "Anti-Ca2+ Channel Antibody Attenuates Ca2+ Currents and Mimics Cerebellar Ataxia In Vio," *Proc. Natl. Acad. Sci. USA* 105(7):2705-2710, (2008).
Liirs et al. "3D Structure of Alzheimer's Amyloid-Beta (1-42) Fibrils," *Proc. Natl. Acad. Sci. USA* 102(48): 17342-17347, (2005).
Lindberg et al. "Beta-Amyloid Protein Structure Determines the Nature of Cytokine Release From Rat Microglia," *J. Mol. Neurosci.* pp. 271-12, (2005).
Lipscombe et aL "Functional Diversity in Neuronal Voltage-Gated Calcium Channels by Alternative Splicing of Cav. Alpha1 ," *Mol. Neurobiol.* 26(1 ):21-44, (2002).
Little et al. "Of Mice and Men: Hybridoma and Recombinant Antibodies," *Immun. Today* 21(8):364-370, (2000).
Liu et al. "Progress in Soluble Abeta Oligomers in Alzheimer's Disease and Drugs Targeting Abeta Oligomers," *Chinese Pharmacological Bulletin* 24(12): 1554-1557, (2008).
Liu et al. "A Novel Nicotinic Acetylcholine Receptor Subtype in Basal Forebrain Cholinergic Neurons With High Sensitivity to Amyloid Peptides," *J. Neurosci.* 29(4):918-929, (2009).
Liu et al. "Residues 17-20 and 35-35 of Beta-Amyloid Play Critical Roles in Aggregation," *J. Neurosci Res.* 75(2):162-171, (2004).
Liu et al. "Trehalose Differentially Inhibits Aggregation and Neurotoxicity of Beta-Amyloid 40 and 42," *Neurobiol. Dis.* 20(1):74-81, (2005).
Liu, et al. "Single Chain Variable Fragments Against Beta-Amyloid (Abeta) Can Inhibit Abeta Aggregation and Prevent Abeta-Induced Neurotoxicity," *Biochem.* 43:6959-6967, (2004).
Lonberg et al. "Antigen-Specific Human Antibodies From Mice Comprising Four Distinct Genetic Modifications," *Nature* 368:856-859, (1994).
Lonberg et al. "Human Antibodies From Transgenic Mice," *Intern. Rev. Immunol.* 13:65-92, (1995).
Lue et al. "Soluble Amyloid Beta Peptide Concentration as a Predictor of Synaptic Change in Alzheimer's Disease," *Am. J. Path.* 155(3):853-862, (1999).
Luhrs, T. et al. "3D Structure of Alzheimer's Amyloid-beta(1-42) Fibrils," *Proceedings of the National Academy of Sciences* 102(48):17342-17347, (Nov. 29, 2005).
Lund et al. "Oligosaccaride-Protein Interactions in Igg Can Modulate Recognition by Fc-Gamma Receptors," *FASEB J.* 9(1):115-119, (1995).

(56) References Cited

OTHER PUBLICATIONS

Lunn et al. "High-Affinity Anti-Ganglioside IgG Antibodies Raised in Complex Ganglioside Knockout Mice: Reexamination of FDIa Immunolocalization," *J. Neurochem.* 75:404-412, (2000).
Ma, W.-L. et al. "P21-Activated Kinase-Aberrant Activation and Translocation in Alzheimer's Disease Pathogenesis," *J. Biol. Chem.* 283(20):14132-14143, (May 16, 2008).
Ma et al. "Polymorphic C-Terminal-Sheet Interactions Determine the Formation of Fibril or Amyloid-Derived Diffusible Ligand-Like Globulomer for the Alzheimer A42 Dodecamer," *J. Biol. Chem.* 285(47):37102-37110, (2010).
Macao et al. "Recombinant Amyloid Beta-Peptide Production by Coexpression With an Affibody Ligand," *BMC Biotechnology* 8:82, (2008).
MacCallum et al. "Antibody-Antigen Interactions: Contact Analysis and Binding Site Topography," *J. Mol. Biol.* 262:732-745, (1996).
Maccioni et al. "What Have We Learned From the Tau Hypothesis? Current Hypothesis and Research Milestones in Alzheimer's Disease Current Hypotheses and Research Milestones in Alzheimer's Disease," *International Summit Meeting on Current Hypotheses on Alzheimer Disease*, Renaca, Chile (Nov. 22-25, 2007).
Maccioni et al. "What Have We Learned from the Tau Hypothesis?" *Current Hypotheses and Research Milestones in Alzheimer's Disease, Springer* pp. 49-62, (2009).
Macquitty et al. "GenPharm's Knockout Mice," *Science* 257:1188, (1992).
Mader et al., "Interaction of the Crystalline Bacterial Cell Surface Layer Protein SbsB and the Secondary Cell Wall Polymer of Geobacillus Stearothermophilus PV72 Assessed by Real-Time Surface Plasmon Resonance Biosensor Technology," *J. Bacteriol.* (2004).
Madrigal et al. "Neuroprotective Actions of Noradrenaline: Effects of Glutathione Synthesis and Activation of Peroxisome Proliferator Activated Receptor Delta," *J. Neurochem.* 103(5):2092-101, (2007).
Maier et al. "Short Amyloid-Beta Immunogens Reduce Cerebral in an Alzheimer's Disease Mouse Model in the Absence of an Amyloid-Beta-Specific Cellular Immune Response," *J. Neurosci.* 26(18):4717-4728, (2006).
Maliga et al. *Methods in Plant Molecular Biology—A Laboratory Manual*, Table of Contents (1995).
Mandal et al. "Alzheimer's Disease: Halothane Induces Abeta Peptide to Oligomeric Form-Solution NMR Studies," *Neurochem. Res.* 31(7):883-890, (2006).
Manelli et al. "A Beta 42 Neurotoxicity in Primary Co-Cultures: Effect of ApoE Isoform and a Beta Conformation," *Neurobiol. of Aging* 281139-1147, (2007).
Manelli et al., "ApoE and Abetal-42 Interactions," *J. Mol. Neurosci.* 23235-246, (2004).
Manelli et al. "Glial Activation by Oligomeric Versus Fibrillar Abetal-42," *Soc. for Neurosci. Abstract Viewer and Itinerary Planner, Abstract No. 193.9, 32nd Annual meeting of the Society for Neuroscience*, Orlando, FL (Nov. 2-7, 2002).
Marchalonis et al. "Evolutionary Factors in the Emergence of the Combinatorial Germline Antibody Repertoire," *Adv. Exp. Med. Biol.* 484:13-30, (2001).
Maria et al. "Upregulation of P2I(Cipl) in Activated Glial Cells," *Glia* 57524-534, (2009).
Mariette, X., "Nucleotidic Sequence Analysis of the Variable Domains of Four Human Monoclonal Igm With an Antibody Activity to Myelin-Associated Glycoprotein," *Eur. J. Immunol.* 23:846-851, (1993).
Marlow et al. "APHI, PEN2 and Nicastrin Increase Abeta Levels and Gamma-Secretase Activity," *Biochem. Biophys. Res. Comm.* 305(3):502-509, (2005).
Masliah et al. "Progress in the Development of New Treatments for Combined Alzheimer's and Parkinson's Diseases," *Drug Development Res.* 56282-292, (2002).
Masman et al. "In Silico Study of Full-Length Amyloid Beta 1-42 Tri- and Penta-Oligomers in Solution," *J. Phys. Chem. B.* 113:11710-11719, (2009).

Masters et al. "Amyloid Plaque Core Portein in Alzheimer Disease and Down Syndrome," *Proc. Natl. Acad. Sci. USA* 82:4245-4249, (1985).
Mastrangelo et al. "High-Resolution Atomic Force Microscopy of Soluble A.Beta.42 Oligomers," *J. Mol. Biol.* 358:106-119, (2006).
Masuda et al. "Identification of Physiological and Toxic Conformations in Abeta42 Aggregates," *Chem Bio Chem.* 10(2):287-295, (2009).
Mathura et al. "Model of Alzheimer's Disease Amyloid-Beta Peptide Based on a RNA Binding Protein," *Biochem. Biophys. Res. Comm.* 332(2):585-592, (2005).
Mattson et al. "A Practical Approach to Crosslinking," *Mol. Biol. Reports* 17:167-183, (1993).
Mattson, M.P. "Pathways Towards and Away From Alzheimer's Disease," *Nature* 430:631-639, (2004).
Mattson, M.P. "Pathways Towards and Away From Alzheimer's Disease," *Nature* 431(7004):107, (2004).
Matveeva, V.A. "Prostaglandin E(2) Release by Human and Syrian Hamster Tumor Cells and Their Sensitivity to Cytostatic Activity of Natural Killers," *Bulletin of Experimental Biology and Medicine* vol. 131(2):156-158, (2001).
Maurer et al. "The Proteome of Neural Stem Cells From Adult Rat Hippocampus," *Proteome Sci.* 1(1):4, (2003).
May, K., "Buying a New Immnoassay System?" *BioTechnology—TIBTECH* 11:272-273, (1993).
McCafferty et al. "Phage Antibodies: Filamentous Phage Displaying Antibody Variable Domains," *Nature* 348:552-554, (1990).
McKinnon et al. "Caspase Activation and Amyloid Precursor Protein Cleavage in Rat Ocular Hypertension," *Investigative Ophthalmology & Visual Science* 43(4):1077-1087, (2002).
McLaurin et al. "Inositol Steroisomers Stabilize an Oligomeric Aggregate of Alzheimer Amyloid Beta Peptide and Inhibit Abeta-Induced Toxicity," *J. Biol. Chem.* 27518495-18502, (2000).
McLaurin et al. "Review Modulating Factors in Amyloid-Beta Fibril Formation," *J. Structural Biol.* 130(2-3):259-270, (2000).
McLaurin et al. "Therapeutically Effective Antibodies Against Amyloid-Beta Peptide Target Amyloid-Beta Residues 4-10 and Inhibit Cytotoxicity and Fibrillogenesis," *Nat. Med.* 8(11):1263-1269, (2002).
McLean et al. "Soluble Pool of Abeta Amyloid as a Determinant of Severity of Neurodegeneration in Alzheimer's Disease," *Am. Neurol. Assoc.* 46:860-866, (1999).
McPherson, A. "Current Approaches to Macromolecular Crystallization," *Eur. J. Biochem.* 189:1-23, (1990).
Meijer et al. "Biochemical and Cellular Effects of Roscovitine, A Potent and Selective Inhibitor of the Cyclin-Dependent Kinases cdc2, cdk2 and cdk5," *Eur. J. Biochem.* 243(12):527-536, (1997).
Meli et al., "Direct In Vivo Intracellular Selection of Conformation-Sensitive Antibody Domains Targeting Alzheimer's Amyloid-Beta Oligomers," *J. Mol. Biol.* 287(3):584-606, (2009).
Mendez et al. "Functional Transplant of Megabase Human Immunoglobulin Loci Recapitulates Human Antibody Response in Mice," *Nat. Genet.* 15(2):146-156, (1997).
Merrifield, B. "Solid Phase Synthesis," *Science* 232:342, (1986).
Merrifield, J., "The Total Synthesis of an Enzyme With Ribonuclease a Activity," *J. Am. Chem. Soc.* 91:501-502, (1969).
Miller et al. "Polymorphism of Alzheimer's A Beta(L 7-42) (P3) Oligomers: The Importance of the Tum Location and Its Conformation," *Biophys. J.* 971168-1177, (2009).
Minkeviciene et al. "Amyloid Beta-Induced Neuronal Hyperexcitability Triggers Progressive Epilepsy," *J. Neurosci.* 29(11):3453-3462, (2009).
Mizushima et al. "pEF-BOX, a Powerful Mammalian Expression Vector," *Nucl. Acids Res.* 18(17):5322, (1990).
Moechars et al. "Early Phenotypic Changes in Transgenic Mice That Overexpress Different Mutants of Amyloid Precursor Protein in Brain," *Journal of Biological Chemistry* 274(10):6483-6492 (1999).
Moir et al. "Autoantibodies to Redox-Modified Oligomeric Abeta are Attenuated in the Plasma of Alzheimer's Disease Patients," *J. Biol. Chem.* 280:17458-17463, (2005).
Monien et al., "A Novel Approach to Alzheimer's Disease Therapy: Inhibition of A Beta 42 Oligomerization by C-Terminal A Beta 42 Fragments," *J. Peptide Sci.* p. 12147, (2006).

(56) References Cited

OTHER PUBLICATIONS

Moretto et al. "Conformation-Sensitive Antibodies Against Alzheimer Amyloid-Beta by Immunization With a Thioredoxin-Constrained B-Cell Epitope Peptide," *J. Biol. Chem.* 282(15):11436-11445, (2007).
Morgan et al., "Human Gene Therapy," *Ann. Rev. Biochem.* 62:191-217, (1993).
Morgan et al., "Abeta-Derived Diffusible Ligands (ADDLs): Clusterin (apo J), Congo Red Binding and Toxicity," *Society for Neuroscience Abstracts Abstract No. 252130, 29th Annual Meeting of the Society for Neuroscience*, Miami Beach, FL (Oct. 23-28, 1999).
Morley, J.S. "Modulation of the Action of Regulatory Peptides by Structural Modification," *TIPS* pp. 463-468, (1980).
Morrison et al. "Chimeric Human Antibody Molecules: Mouse Antigen-Binding Domains With Human Constant Region Domains," *Proc. Natl. Acad. Sci. USA* 81:6851-6855, (1984).
Morrison, S.L. "Transfectomas Provide Novel Chimeric Antibodies," *Science* 229:1202-1207, (1986).
Mueller et al. "Apolipoprotein E Isoforms Increase Intracellular Ca2+ Differentially Through an Omega-Agatoxin IVA-Sensitive Ca2+ Channel," *Brain Pathology* 8(4):641-653, (1998).
Mullan et al. "A Pathogenic Mutation for Probable Alzheimer's Disease in the App Gene at the N-Terminus of Beta-Amyloid," *Nat. Genet.* 1(5):345-347, (1992).
Mullan et al."A Locus for Familial Early-Onset Alzheimer's Disease on the Long Arm of Chromosome 14, Proximal to the Al-Amtichymotrypain Gene," *Nature Genetics* 2:340-342, (1992).
Muller et al. "Impaired Ca-Signaling in Astroycytes From the Ts16 Mouse Model of Down Syndrome," *Neurosci. Lett.* 223(2):81-84, (1997).
Mulligan, R.C. "The Basic Science of Gene Therapy," *Science* 260:926-932, (1993).
Mullis et al. "Specific Enzymatic Amplification of DNA In Vitro: The Polymerase Chain Reaction," *Cold Spring Harbor Symp. Quant. Biol.* 51:263-273, (1986).
Munter et al. "GxxxG Motifs Within the Amyloid Precursor Protein Transmembrane Sequence are Critical for the Etiology of Abeta42," *EMBO J.* 26(6):1702-1712, (2007).
Murphy et al. "CD40 Stimulation Promotes Human Dsecondary Immunoglobulin Responses in HuPBL-SCID Chimeras," *Clin. Immunol.* 90(1):22-27, (1999).
Murphy et al. "The HuPBL-SCID Mouse as a Means to Examine Human Immune Function In Vivo," *Immunol.* 8:233-241, (1996).
Murray et al. "Amyloid Beta Protein: A Beta 40 Inhibits A Beta 42 Oligomerization," *J. Am. Chem. Soc.* 131:6316-6317, (2009).
Myagkova et al. "Autoantibodies to Beta-Amyloid and Neurotransmitters in Patients With Alzheimer's Disease and Senile Dementia of the Alzheimer Type," *Bulletin of Exp. Biol. Med.* 2:127-129, (2001).
Nagele et al. "Contribution of Glial Cells to the Development of Amyloid Plaques in Alzheimer's Disease," *Neurobiol of Aging* 25(5):663-674, (2004).
Naslund et al. "Relative Abundance of Alzheimer Abeta Amyloid Peptide Variants in Alzheimer Disease and Normal Aging," *Proc. Natl. Acad. Sci. USA* 91:8378-8382, (1994).
Nath et al. "Autoantibodies to Amyloid B-Peptide (AB) are Increased in Alzheimer's Disease Patients and AB Antibodies Can Enhance AB Neurotoxicity," *Neuromol. Med.* 3:29-39, (2003).
Needleman et al. "A General Method Applicable to the Search for Similarities in the Amino Acid Sequence of Two Proteins," *J. Mol. Biol.* 48:443-453, (1970).
Nemes et al. "Cross-Linking Ofobiquitin, HSP27, Parkin, and Alpha-Synuclein by Gamma-Glutamyl-1:-Lysine Bonds in Alzheimer's Neurofibrillary Tangles," *FASEB J.* 18:1135-1137, (2004).
Nerelius et al. "Alpha-Helix Targeting Reduces Amyloid-Beta Peptide Toxicity," *Proc. Natl. Acad. Sci. USA* 106(23):9191-9196, (2009).
Neuberger et al. "Recombinant Antibodies Possessing Novel Effector Functions," *Nature* 312:604-608, (1984).
Nguyen et al. "Production of Human Monoclonal Antibodies in SCID Mouse," *Microbiol. Immunol.* 41(12):901-907, (1997).
Nicholas et al. "Different Amyloid-Ent Amyloid-Beta Aggregation States Induced Monocyte Differentiation or Activation," *J. Neurochem.* 10867, *40th Annual Meeting of the American Society for Neurochemistry*, Charleston, South Carolina (Mar. 7-11, 2009).
Nicolau et al. "A Liposome-Based Therapetuci Vaccine Against Beta-Amyloid Plaques on the Pancreas of Transgenic NORBA Mice," *Proc. Natl. Acad. Sci. USA* 99(4):2332-2337, (2002).
Nielsen et al. "Preferential Uptake of Amyloid Beta 1-42 Oligomers by Primary Human Astrocytes In Vitro: Influence of SAP and Clq," *Mol. Immunol.* 262860, *12th European Meeting on Complement in Human Disease*, Hungary (Sep. 5-8, 2009).
Nilges et al. "Determination of Three-Dimensional Structures of Proteins From Interproton Distance Data by Hybrid Distance Geometry-Dynamical Simulated Annealing Calculations," *FEBS Lett.* 229(2):317-324, (1989).
Nimmrich et al. "Amyloid Beta Oligomers (Abeta(I-42) Globulomer) Suppress Spontaneous Synaptic Activity by Inhibition of P/Q-Type Calcium Currents," *J. Neurosci.* 28(4):788-797, (2008).
Nimmrich et al. "Is Alzheimer's Disease a Result of Presynaptic Failure?—Synaptic Dysfunctions Induced by Oligomeric P-Amyloid," *Rev. Neurosci.* 20(1):1-12, (2009).
Ning et al. "Intratumoral Radioimmunotherapy of a Human Colon Cancer Xenograft Using a Sustained-Release Gel," *Radiotherapy & Oncology* 39:179-189, (1996).
Nomura et al. "Mechanism of Impairment Oflong-Term Potentiation by Amyloid Beta Is Independent of NMDA Receptors or Voltage-Dependent Calcium Channels in Hippocampal CA1 Pyramidal Neurons," *Neurosci. Lett.* 391(1-2):1-6, (2005).
Oi et al. "Chimeric Antibodies," *BioTechniques* 4(3):214-215, (1985).
Okamuro et al. "Regulation of Plant Gene Expression: General Principles," *The Biochemistry of Plants—A comprehensive Treatise*, 15:1-82 (1989).
Ono et al. "Effects of Grape Seed-Derived Polyphenols on Amyloid Beta-Protein Self-Assembly and Cytotoxicity," *J. Biol. Chem.* 283(47):32176-32187, (2008).
Opazo et al. "Metalloenzyme-Like Activity of Alzheimer's Disease Beta-Amyloid: Cu-Dependent Catalytic Conversion of Dopamine, Cholesterol, and Biological Reducing Agents to Neurotoxic H SUB 20 SUB 2," *J. Biol. Chem.* 277(43):40302-40308, (2002).
Orgogozo et al. "Subacute Meningoencephalitis in a Subset of Patients With AD After AP42 Immunization," *Neurology* 61-46-54, (2003).
Origlia et al. "Abeta-Dependent Inhibition of LTP in Different Intracortical Circuits of the Visual Cortex: The Role of RAGE," *J. Alzheimer's Disease* 17(1):59-68, (2009).
Otto et al. "Neurochemical Approaches of Cerebrospinal Fluid Diagnostics in Neurogenerative Diseases," *Methods* 44(4):289-298, (2008).
Padlan et al. "Structure of an Antibody-Antigen Complex: Crystal Structure of the HyHEL-10 Fab-Lysozyme Complex," *Proc. Natl. Acad. Sci USA* 86:5938-5942, (1989).
Padlan et al. "Identification of Specificity-Determining Residues in Antibodies," *FASEB* 9:133-139, (1995).
Padlan, E.A., "A Possible Procedure for Recucing the Immunogenicity of Antibody Variable Domains While Preserving Their Ligand-Binding Properties," *Molec. Immunol.* 28(415):489-498, (1991).
Palmer et al. "Endothelin-Converting Enzyme-2 Is Increased in Alzheimer's Disease and Up-Regulated by Abeta," *Am. J. Path.* 175(1):262-270, (2009).
Pan et al. "Tripchlorolide Protects Neuronal Cells From Microglia-Mediated Beta-Amyloid Neurotoxicity Through Inhibiting NF-kappa B and JNK Signaling," *GLIA* 57:1227-1238, (2009).
Pan et al. "Effect of Inflammatory Responses in Microglia Induced by Oligomeric Beta-Amyloid SUB 1-42 on Neuronal Cells," *Acta Anatomica Sinica* 39(6):804-809, (2008).
Partis et al. "Crosslinking of Proteins by Omega-Maleimido Alkanoyl N-Hydroxysuccinimide Esters," *J. Protein Chem.* 2:263-277, (1983).
Pastor et al. "Amyloid Toxicity Is Independent of Polypeptide Sequence, Length and Chirality," *J. Mol. Biol.* 375:695-707, (2008).
Paul, W.E. "Fv Structure and Diversity in Three Dimensions: Fundamental Immunology," 3$^{rd}$ *Edition, Raven Press. Ltd.* pp. 292-295 (1993).

(56) References Cited

OTHER PUBLICATIONS

Peacock et al. "Novel Amyloid Precursor Protein Gene Mutation (codon 665Asp) In a Patient With Late-Onset Alzheimer's Disease," *Ann. Neurol.* 35(4):432-438, (1994).
Peacock et al. "Novel Polymorphism in the A4 Region of the Amyloid Precursor Protein Gene in a Patient Without Alzheimer's Disease," *Neurol.* 43(6):1254-1256, (1993).
Pearson et al. "Improved tools for biological sequence comparison," *PNAS* 85:2444-2448, (1988).
Pellicano, M. et al., "The Sea Urchin Embryo: A Model to Study Alzheimer's Beta Amyloid Induced Toxicity," *Archives of Biochem. Biophys.* 483:120-126, (2009).
Perouansky, M., "Liaisons Dangereuses? General Anaesthetics and Long-Term Toxicity in the CNS," *Eur. J. Anaesthesiol.* 24(2):107-115, (2007).
Persic et al. "An Integrated Vector System for the Eukaryotic Expression of Antibodies or Their Fragments After Selection From Phage Display Libraries," *Gene* 187:9-18, (1997).
Petrushina, I. "Alzheimer's Disease Peptide Epitope Vaccine Reduces Insoluble But Not Soluble/Oligomeric Abeta Species in Amyloid Precursor Protein Transgenic Mice," *J. Neurosci.* 27(46): 12721-12731, (2007).
Pfeifer et al. "Cerebral Hemorrhage After Passive Anti-AB Immunotherapy," *Science* 298:1379, (2002).
Phu et al. "Fluorescence Resonance Energy Transfer Analysis of Apolipoprotein E C-Terminal Domain and Amyloid Beta Peptide (1-42) Interaction," *J. Neurosci. Res.* 80(6):877-886, (2005).
Pike et al. "Structure-Activity Analyses of B-Amyloid Peptides: Contributions of the B25-35 Region to Aggregation and Neurotoxicity," *J. Neurochem.* 64(1):253-265, (1995).
Plant et al. "The Production of Amyloid Beta Peptide Is a Critical Requirement for the Viablility of Central Neurons," *J. Neurosci.* 23(13):5531-5535, (2003).
Podlisny et al. "Aggreagation of Secreted Amyloid Beta-Protein Into Sodium Dodecyl Sufate-Stable Oligomers in Cell Culture," *J. Biol. Chem.* 270(16):9564-9570, (1995).
Poljak, R.J., "Production and Structure of Diabodies," *Structure* 2:1121-1123, (1994).
Portelius et al. "Targeted Proteomics in Alzheimer's Disease: Focus on Amyloid-Beta," *Exp. Rev. Proteomics* 5(2):225-237, (2008).
Portolano et al. "High Affinity, Thyroid-Specific Human Autoantibodies Displayed on the Surface of Filamentous Phage Use V Genes Similar to Other Autoantibodies," *J. Immunol.* 151(5):L2839-2851, (1993).
Presta et al. "Humanization of an Antibody Directed Against IgE," *J. Immunol.* 151(5):2623-2632, (1993).
Putney, P.W., *Calcium Signaling, CRC Press Inc.* (2005).
Puzzo et al. "Picomolar Amyloid-Beta Positively Modulates Synaptic Plasticity and Memory in Hippocampus," *J. Neurosci.* 28:14537-14545, (2008).
Qian et al. "Presynaptic Ca2+ Channels and Neurotransmitter Release at the Terminal of a Mouse Cortical Neuron," *J. Neurosci.* 21(11):3721-3728, (2001).
Qiu et al. "Facile Synthesis of Hydrocarbon-Stapled Peptides," *Anaspec poster at 20th American Peptide Society Annual Meeting* 1 page. (2008).
Qiu et al. "Convenient, Large-Scale Asymmetric Synthesis of Eriantiomerically Pure Trans-Cinnamylglycine and-Alpha-Alamine," *Tetrahedron* 56:2577-2582, (2000).
Qiu et al. "Degradation of Amyloid Beta-Protein by a Metalloprotease Secreted by Microglia and Other Neural and Non-Neural Cells," *J. Biol. Chem.* 272(10):6641-6646, (1997).
Qiu et al. "Insulin-Degrading Enzyme Regulates Extracellular Levels of Amyloid Beta-Protein by Degradation," *J. Biol. Chem.* 273(49):32730-32738, (1998).
Racke et al. "Exacerbation of Cerebral Amyloid Angiopathy-Associated Microhemorrhage in Amyloid Precursor Protein Transgenic Mice by Immunotherapy Is Dependent on Antibody Recognition of Deposited Forms of Amyloid Beta," *Journal of Neuroscience* 25(3):629-636, (2005).

Rahimi et al. "Photo-Induced Cross-Linking of Unmodified Proteins (PICUP) applied to Amyloidogenic Peptides," *J. Visualized Exp.* p. 23, (2009).
Rahimi et al. "Structure-Function Relationships of Pre-Fibrillar Protein Assemblies in Alzheimer's Disease and Related Disorders," *Curr. Alzheimer Res.* 5(3):319-341, (2008).
Rambaldi et al. "In Vitro Amyloid A Beta(L-42) Peptide Aggregation Monitoring by Asymmetrical Flow Field-Flow Fractionation With Multi-Angle Light Scattering Detection," *Anal. Bioanal. Chem.* 394:2145-2149, (2009).
Rangachari et al. "Amyloid Beta(L-42) Rapidly Forms Protofibrils and Oligomers by Distinct Pathways in Low Concentrations of Sodium Dodecylsulfatet," *Biochem.* 46:12451-12462, (2007).
Rangachari et al. "Rationally Designed Dehydroalanine (Delta Ala)-Containing Peptides Inhibit Amyloid-Beta (A Beta) Peptide Aggregation," *Biopolymers* 91:456-465, (2009).
Rangachari et al. "Secondary Structure and Interfacial Aggregation of Amyloid Beta(1-40) on Sodium Dodecyl Sulfate Micelles," *Biochem.* 45:8639-8648, (2006).
Ravault et al. "Fusogenic Alzheimer's Peptide Fragment Abeta (29-42) In Interaction With Lipid Bilayers: Secondary Structure, Dynamics, and Specific Interaction With Phosphatidyl Ethanolamine Polar Heads as Revealed by Solid-State NMR," *Protein Sci.* 14(5):1181-1189, (2005).
Ravetch et al. "Structure of the Human Immunoglobulin μ Locus: Characterization of Embryonic and Rearranged J and D Genes," *Cell* 27:583-591, (1981).
Reisner et al. "The Trimera Mouse: Generating Human Monoclonal Antibodies and an Animal Model for Human Diseases," *Trends in Biotech.* 16:242-246, (1998).
Remington: *The Science and Practice of Pharmacy, Mack Publishing* (1995) 19th Edition: Table of Contents.
Resende et al. "ER stress Is Involved in Abeta-Induced GSK-3 Beta Activation and Tau Phosphorylation," *J. Neurosci. Res.* 86(9):2091-2099, (2008).
Resende et al. "Neurotoxic Effect of Oligomeric and Fibrillar Species of Amyloid-Beta Peptide 1-42: Involvement of Endoplasmic Reticulum Calcium Release in Oligomer-Induced Cell Death," *Neurosci.* 155(3):725-737, (2008).
Riechman et al. "Reshaping Human Antibodies for Therapy," *Nature* 332:323-327, (1988).
Robert et al. "Engineered Antibody Intervention Strategies for Alzheimer's Disease and Related Dementias by Targeting Amyloid and Toxic Oligomers," *Protein Engineering, Design and Selection* 22(3):199-208, (2009).
Roberts et al. "RNA-Peptide Fusions for the In Vitro Selection of Peptides and Proteins," *Proc. Natl. Acad. Sci. USA* 94:12297-12302, (1997).
Robinson et al. Sustained and Controlled Release Drug Delivery Systems, (1978) Table of Contents.
Roes et al. "Mouse Anti-Mouse IgD Monoclonal Antibodies Generated in IgD-Deficient Mice," *J. Immunol. Meth.* 183:231-237, (1995).
Roguska et al. "Humanization of Murine Monclonal Antibodies Through Variable Domain Resurfacing," *Proc. Natl. Acad. Sci. USA* (1994) 91:969-973, (1994).
Roher et al. "Oligomerization and Fibril Assembly of the Amyloid-Beta Protein," *Biochimica et Biophysica Acta* 1502(1):31-43, (2000).
Roher et al. "Morphology and Toxicity of Abeta-(1-42) Dimer Derived From Neuritic and Vascular Amyloid Deposits of Alzheimer's Disease," *J. Biol. Chem.* 271(34):20631-20635, (1996).
Ronicke et al. "Abeta Mediated Diminution of MTT Reduction—An Artefact or Single Cell Culture?" *PLoS ONE* 3(9) e3236, (2008).
Rossi et al. "A Family With Alzheimer Disease and Strokes Associated With A713T Mutation of the APP Gene," *Neurology* 63(5):910-912, (2004).
Rouillard et al. "Gene2Oligo: Oligonucleotide Design for In Vitro Gene Synthesis," *Nucl. Acids. Res.* 32:WI76-180, (2004).
Rovira et al. "Abeta(25-35) and Abeta(1-40) Act on Different Calcium Channels in CA1 Hippocampal Neurons," *Biochem. Biophys. Res. Comm.* 296:1317-1321, (2002).

(56) References Cited

OTHER PUBLICATIONS

Rudikoff et al., "Single Amino Acid Substitution Altering Antigen-Binding Specificity," *Proc. Natl. Acad. Sci. USA* 79(6):1979-1983, (1982).
Russo et al. "Presenilin-1 Mutatiosn in Alzheimer's Disease," *Nature* 405:531-532, (2000).
Rzepecki et al. "Prevention of Alzheimer's Disease-Associated Abeta Aggregation by Rationally Designed Nonpeptide Beta-Sheet Ligands," *J. Biol. Chem.* 279(46):47497-47505, (2004).
Sabella et al. "Capillary Electrophoresis Studies on the Aggregation Process of Beta-Amyloid 1-42 and 1-40 Peptides," *Electrophoresis* 25:3186-3194, (2004).
Saido et al. "Dominant and Differential Deposition of Distinct Beta-Amyloid Peptide Species, AbetaN3 in Senile Plaques," *Neuron* 14:457-486, (1995).
Sakmann et al. "Single-Channel Recording" in *Antibodies, 2nd edition*, Springer, Table of Contents (1995).
Salomon et al. "Nicotine Inhibits Amyloid Formation by the Beta-Peptide," *Biochem.* 35(42):13568-78, (1996).
Sambamurti et al. "A Partial Failure of Membrane Protein Turnover May Cause Alzheimer's Disease: A New Hypothesis," *Curr. Alzheimer Res.* 3:81-90, (2006).
Sambrook et al., "Molecular Cloning," in *A Laboratory Manual, 2nd Edition* Cold Spring Harbor Laboratory Press,—Table of Contents, (1989).
Sambrook J., "Expression of Cloned Genes in *Escherichia coli*" Molecular Cloning, $2^{nd}$ *Edition, Cold Spring Harbor Laboratory Press*, Chap. 17.2-17.9, (1989).
Samoszuk et al. "A Peroxide-Generating Immunoconjugate Directed to Eosinophil Peroxidase Is Cytotoxic to Hodgkin's Disease Cells In Vitro," *Antibody, Immunoconjugates and Radiopharmaceuticals* 2:37-45, (1989).
Sandberg et al. "Stabilization of Neurotoxic Alzheimer Amyloid-Beta Oligomers by Protein Engineering," *Proc. Natl. Acad. Sci. USA* 107(35):15595-15600, (2010).
Sankaranarayanan, S., "Genetically Modified Mice Models for Alzheimer's Disease," *Curr. Top. Med. Chem.* 6(6):609-627, (2006).
Santos et al. "A Method for the Detection of Amyloid-Beta SUB 1-40, Amyloid-Beta SUB 1-42 and Amyloid-Beta Oligomers in Blood Using Magnetic Beads in Combination With Flow Cytometry and Its Application in the Diagnostics of Alzheimer's Disease," *J. Alzheimer's Dis.* 14(2):127-131, (2008).
Sanz-Blasco et al. "Mitochondrial Ca2+ overload Underlies A Beta Oligomers Neurotoxicity Providing an Unexpected Mechanism of Neuroprotection by NSAIDs," *PloS One* 3 Article No. e2718, (2008).
Sato et al. "Design of Peptides That Form Amyloid-Like Fibrils Capturing Amyloid Beta 1-42 Peptides," *Chemistry A Eur. J.* 13:7745-7752, (2007).
Sato et al. "Development of New Screening System for Alzheimer Disease, In Vitro Abeta Sink Assay, to Identify the Dissociation of Soluble Abeta From Fibrils," *Neurobiol. Dis.* 22(3):487-495, (2006).
Saudek et al. "A Preliminary Trail of the Programmable Implantable Medication System for Insulin Delivery," *New Engl. J. Med.* 321(9):574-579, (1989).
Sawai et al. "Direct Production of the Fab Fragment Derived From the Sperm Immobilizing Antibody Using Polymerase Chain Reaction and CDNA Expression Vectors," *Amer. J. Reproduc. Immunol.* 34:26-34, (1995).
Schable et al. "Characteristics of the Immunoglobulin V Kappa Genes, Pseudogenes, Relics and Orphons in the Mouse Genome," *Eur. J. Immunol.* 29:2082-2086, (1999).
Schafmeister et al. "An All-Hydrocarbon Cross-Linking System for Enhancing the Helicity and Metabolilc Stability of Peptides," *J. Am. Chem. Soc.* 122:5891-5892, (2000).
Schenk, D., "Amyloid-Beta Immunotherapy for Alzheimer's Disease: The End of the Beginning," *Nature* 3:824-828, (2002).
Schenk et al. "Current Progress in Beta-Amyloid Immunotherapy," *Current Opinion in Immunology* 16:599-606, (2004).

Schenk et al. "Immunization With Amyloid-Beta Attenuates Alzheimer'disease-Like Pathology in the PDAPP Mouse," *Nature* 400:173-177,(1999).
Schilling et al. "On the Seeding and Oligomerization of Pglu-Amyloid Peptides (In Vitro)," *Biochem.* 45(41):12393-12399, (2006).
Scholtzova et al. "Induction for Toll-Like Receptor 9 Signaling as a Method for Ameliorating Alzheimer's Disease-Related Pathology," *J. Neurosci.* 291846-1854, (2009).
Schott et al. "New Developments in Mild Cognitive Impairment and Alzheimer's Disease," *Curr. Opin. Neurol.* 19(6):552-558, (2006).
Schuck, P. "Size Distribution Analysis of Macromolecules by Sedimentation Velocity Ultracentrifugation and Lamm Equation Modeling," *Biophys. J.* 78:1606-1619, (2000).
Sciaretta et al. "Abeta40-Lactam (D23/K28) Models a Conformation Highly Favorable for Nucleation of Amyloid," *Biochem.* 44:6003-6014, (2005).
Sefton, M.V. "Implantable Pumps," *Critical Reviews in Biomedical Engineering* 14(3):201240, (1987).
Selenica et al. "Cystatin C Reduces the In Vitro Formation of Soluble Abetal-42 Oligomers and Protofibrils," *Scan. J. Clin. Lab. Invest.* 67(2): 179-190, (2007).
Selkoe, D.J. "Alzheimer's Disease: Genes, Proteins and Therapy," *Physiol. Reviews, American Physiological Society* 81(2):741-766, (2001).
Selkoe, "Clearing the Brain's Amyloid Cobwebs," *Neuron* 32:177-180, (2001).
Sergeant et al. "Truncated Beta-Amyloid Peptide Species in Pre-Clinical Alzheimer's Disease as New Targets for the Vaccination Approach," *Journal of Neurochemistry* 85(6):1581-1591, (2003).
Shankar et al. "Natural Oligomers of the Alzheimer Amyloid-Beta Protein Induce Reversible Synapse Loss by Modulating an NMDA-Type Glutamate Receptor-Dependent Signaling Pathway," *J. Neurosci.* 27(11):2866-2875, (2007).
Shapiro et al. "DNA target Motifs of Somatic Mutagenesis in Antibody Genes," *Crit. Rev. in Immunol.* 22(3):183-200, (2002).
Shields et al. "Lack of Fucose on Human IgG 1 N-linked Oligosaccharide Improves Binding to Human FcyRIII and Antibody-Dependent Cellular Toxicity," *J. Biol. Chem.* 277(30):26733-26740, (2002).
Shimizu et al. "IL-4- induced Selective Clearance of Oligomeric Beta-Amyloid Peptide(1-42) by Rat Primary Type 2 Microglia," *J. Immun.* 181(9):6503-6513, (2008).
Shu et al. "Secretion of a Single-Gene-Encoded Immunoglobulin From Myeloma Cells," *Proc. Natl. Acad. Sci. USA* 90:7995-7999, (1993).
Shughrue et al. "Anti-ADDL Antibodies Differentially Block Oligomer Binding to Hippocampal Neurons," *Neurobiol. Aging* 31:189-202, (2010).
Sikorski et al. "Structure and Texture of Fibrous Crystals Formed by Alzheimer's Abeta (11-25) Peptide Fragment," *Structure (London)* 11(8):915-926, (2003).
Sims et al. "A Humanized CD18 Antibody Can Block Function Without Cell Destruction," *J. Immunol.* 151(4):2296-2308, (1993).
Sinz, A., "Chemical Cross-Linking and Mass Spectrometry for Mapping Three-Dimensional Structures of Proteins and Protein Complexes," *J. Mass Spectrom.* 38:1225-1237, (2003).
Sjogren et al. "Cholesterol and Alzheimer's Disease—Is There a Relation ?" *Mechanisms of Aging and Development* 127:138-147, (2006).
Sjogren et al. "The Link Between Cholesterol and Alzheimer's Disease," *World J. Biol. Psych.* 6(2):85-97, (2005).
Skerra et al. "Assembly of a Functional Immunoglobulin F Fragment in *Escherichia coli*," *Science* 240: 1038-1040, (1988).
Smith et al. "Concentration Dependent Cu SUP 2+ induced Aggregation and Dityrosine Formation of the Alzheimer's Disease Amyloid-Betapeptide," *Biochem.* 46(10):2881-2891, (2007).
Smith et al. "Amphotericin B Interactions With Soluble Oligomers of Amyloid A Beta 1-42 Peptide," *Bioorg. Med. Chem.* 17:2366-2370, (2009).
Smith et al. "Comparison of Biosequences," *Adv. in Applied Math.* 2:482-489, (1981).

(56) References Cited

OTHER PUBLICATIONS

Smith-Gill et al. "Contributions of Immunoglobulin Heavy and Light Chains to Antibody Specificity for Lysozyme and Two Haptens," *J. Immunol.* 139:4135-4144, (1987).
Smithson et al. "Molecular Analysis of the Heavy Chain of Antibodies That Recognize the Capsular Polysaccharide of Neisseria Meningitides in hu-PBMC Reconsituted SCID Mice and in the Immunized Human Donor," *Molec. Immunol.* 36:113-124, (1999).
Smolen et al. editors, *Controlled Drug Bioavailability: Drug Product Design and Performance*, vol., John Wiley & Sons, Table of Contents (1984).
Solomon et al. "Disaggregation of Alzheimer Beta-Amyloid by Site-Directed mAb," *Proc. Natl. Acad. Sci. USA*, 94:4109-4112, (1997).
Solomon et al. "Monoclonal Antibodies Inhibit in Vitro Fibrillar Aggregation Fo the Alzheimer Beta-Amyloid Peptide," *Proc. Natl. Acad. Sci. USA* 93:452-455, (1996).
Solorzano-Vargas et al. "Epitope Mapping and Neuroprotective Properties of a Human Single Chain FV antibody That Binds an Internal Epitope of Amyloid-Beta 1-42," *Molecular Immunol.* 45(4): 881-886, (2008).
Sondag et al. "Beta Amyloid Oligomers and Fibrils Stimulate Differential Activation of Primary Microglia," *J. Neuroinflamm.* 6 article No. 1, (2009).
Song et al. "Light Chain of Natural Antibody Plays a Dominant Role in Protein Antigen Binding," *Biochem. Biophys. Res. Comm.* 268:390-394, (2000).
Song et al. "Antibody Mediated Lung Targeting of Long-Circulating Emulsions," *PDA J. of Pharm. Sci Tech.* 50:372-397, (1995).
Soos et al. "An Improved Synthesis of Beta-Amyloid Peptides for In Vitro and In Vivo Experiments," *J. Peptide Science* 10:136, (2004).
Sorensen et al. "ApoE Counteracts the Impairment of Mitochondrial Activity Induced by Oligomeric a Beta 1-42," *Eur. J. Neurol.* 15:45, (2008).
Spatola et al. "Structure-Activity Relationships of Enkephalins Containing Serially Replaced Thiomethylene Amide Bond Surrogates," *Life Sci.* 38:1243-1249, (1986).
Spatola et al. "Chemistry and Biochemistry of Amino Acids, Peptides and Proteins," *Science, Marcel Dekker* pp. 267-357, (1983).
Spencer et al. "Novel Strategies for Alzheimer's Disease Treatment," *Exp. Opin. Biol. Ther.* 7(12): 1853-1867, (2007).
Stan, R.V. "Multiple PVI Dimers Reside in the Same Stomatal or Fesestral Diaphragm," *Am. J. Physiol. Heart Circ. Physiol.* 286(4):H1347-1353, (2004).
Standridge, J.B. "Vicious Cycles Within the Neuropathophysiologic Mechanisms of Alzheimer's Disease," *Curr. Alzheimer Res.* 3(2):95-107, (2006).
Staros et al. "Enhancement by N-Hydroxysulfosuccinimide of Water-Soluble Carbodilimide-Mediated Coupling Reactions," *Anal. Biochem.* 156(1):220-222, (1986).
Stewart et al. *Solid-Phase Peptide Synthesis, 2nd Edition*, Pierce Chemical Company Table of Contents, (1984).
Stine et al. "In Vitro Characterization of Conditions for Amyloid-Beta Peptide Oligomerization and Fibrillogenesis," *J. Biol. Chem.* 278(13):11612-11622, (2003).
Stine et al. "Antibodies Specific for Toxic Abeta Oligomers," Abst. Viewer/Itinerary Planner, *Soc. of Neurosci.* (2003).
Studnicka et al. "Human-Engineered Monoclonal Antibodies Retain Full Specific Binding Activity by Preserving Non-CDR Complementarity-Modulating Residues," *Protein Eng.* 7(6):805-814, (1994).
Suram et al. "A New Evidence for DNA Nicking Property of Amyloid Beta-Peptide (1-42): Relevance of Alzheimer's Disease," *Archives of Biochem. Biophys.* 463(2):245-252, (2007).
Tabaton et al. "Role of Water-Soluble Amyloid-Beta in the Pathogenesis of Alzheimer's Disease: Role of Amyloid-Beta in Alzheimer's Disease," *Int. J. Exp. Path.* (2005) 3(85):139-145, (2005).
Tabaton, M. "Coffee 'Breaks' Alzheimer's Disease," *J. Alzheimer's Disease* 17/3:699-700, (2009).

Taguchi et al. "Different Expression of Calreticulin and Immunoglobulin Binding Protein in Alzheimer's Disease Brain," *Acta Neuropathologica* 100(2):153-160, (2000).
Takano, K. "Amyloid Beta Conformation in Aqueous Environment," *Curr. Alzheimer Res.* 5(6):540-547, (2008).
Takata et al. "High Mobility Group Box Protein-1 Enhances Amyloid-Beta Neurotoxicity," *J. Pharm. Sci.* 100154P, 79th Annual Meeting of the Japanese Pharmacological Society, Yokohama, Japan, (Mar. 8-10, 2006).
Takata et al. "Possible Involvement of Small Oligomers of Amyloid-Beta Peptides in 15-DeoxyDELTA12, 14 Prostaglandin J2-Sensitive Microglial Activation," *J. Pharm. Sci.* 91:330-333, (2003).
Takeda et al. "Construction of Chimaeric Processed Immunoglobulin Genes Containing Mouse Variable and Human Constant Region Sequences," *Nature* 314:452-454, (1985).
Tamagno et al. "The Various Aggregation States of Beta-Amyloid 1-42 Mediate Different Effects on Oxidative Stress, Neurodegeneration, and BACE-1 Expression," *Free Radie. Biol. Med.* 41(2):202-212, (2006).
Tamura et al. "Structural Correlates of an Anticarcinoma Antibody:Identification of Specificity-Determining Residues (SDRs) and Development of a Minimally Immunogenic Antibody Variant by Retention of SDRs Only," *J. Immunol.* 164(3):1432-1441, (2000).
Taniguchi et al. "'Click Peptide':pH-Triggered In Situ Production and Aggregation of Monomer Abetal-42," *Chembiochem*. 10(4);710-715, (2009).
Taniuchi et al. "Induction of Nerve Growth Factor Receptor in Schwarm Cells After Axotomy," *Proc. Natl. Acad. Sci. USA* 83:4094-4098, (1986).
Tanzi, R. "Alzheimer Research Forum Discussion: Gain or Loss of Function—Time to Shake Up Assumptions on Gamma-Secretase in Alzheimer Disease? Commentary," *J. Alzheimer's Dis.* 11(3):409, (2007).
Tanzi, R.E. "Novel Therapeutics for Alzheimer's Disease," *Neurotherapeutics* 5(3):377-380, (2008).
Tarozzi et al. "Cyanidin 3-0-Glucopyranoside Protects and Rescues SH-Sy5Y Cells Against Amyloid-Beta Peptide-Induced Toxicity," *Neuroreport* 19(15):1483-1486, (2008).
Taylor et al. "A Transgenic Mouse That Expresses a Diversity of Human Sequence Heavy and Light Chain Immunoglobulins," *Nucl. Acids. Rse.* 20(23):6287-6295, (1992).
Tenno et al. "Structural Basis for Distinct Roles of Lys63- and Lys48-Linked Polyubiquitin Chains," *Genes to Cells* 9:865-875, (1994).
Teplow et al. "Effects of Structural Modifications in a β on Its Oligomer Size Distribution," *Soc. for Neurosci. Abstract Viewer and Itinerary Planner Abstract No. 19.6, 32nd Annual meeting of the Society for Neuroscience*, Orlando, FL (Nov. 2-7, 2002).
Teplow et al. "Effects of Structural Modifications in Aβ on its Oligorner Size Distribution," *Society for Neuroscience, Abstract Presentation No. 91.20*,(2002).
Terry et al. "Physical Basis of Cognitive Alterations in Alzheimer's Disease: Synapse Loss Is the Major Correlate of Cognitive Impairment," *Am. Neurol. Assoc.* 30:572-580, (1991).
Terryberry et al. "Autoantibodies in Neurodegenerative Diseases: Antigen-Specific Frequencies and Intrathecal Analysis," *Neurobiology of Aging* 19(3):205-216, (1998).
Tew et al. "Stabilization of Neurotoxic Soluble Beta-Sheet-Rich Conformations of the Alzheimer's Disease Amyloid-Beta Peptide," *Biophys. J.* pp. 974752-972766, (2008).
Thal et al."Fleecy Amyloid Deposits in the Internal Layers of the Human Entorhinal Cortex are Comprised of N-Terminal Truncated Fragments of A13," *Journal of Neuropathology and Experimental Neurology* 58:210-216, (1999).
Tijssen P., "Hybridization with Nucleic Acid Probes", *Part I: Theory and Nucleic Acid Preparation*, Elsevier Science, Table of Contents,(1993).
Tijssen, P editor, "Hybridization With Nucleic Acid Probes-Part II: Probe Labeling and Hybridzation Techniques," *Laboratory Techniques in Biochemistry and Molecular Biology*, 24:iii-vi, 269-613, table of contents, (1993).
Tolstoshev, P. "Gene Therapy, Concepts, Current Trials and Future Directions," *Ann. Rev. Pharmacol. Toxicol.* 32:573-596, (1993).

(56) References Cited

OTHER PUBLICATIONS

Tomaselli et al. "The Alpha-To-Beta Conformational Transition of Alzheimer's Abeta-(1-42) Peptide in Aqueous Media Is Reversible: A Step by Step Conformational Analysis Suggests the Location of Beta Conformation Seeding," *ChemBioChem*. 7(2):257-267, (2006).

Tomidokoro et al. "Familial Danish Dementia: Co-Existence of Danish and Alzheimer Amyloid Subunits (ADAN/ABETA) in the Absence of Compact Plaques," *J. Biol. Chem*. 280(44):36883-36894, (2005).

Tomidokoro et al. "Familial Danish Dementia: The Relationship of Two Different Amyloids (ADAN/ABETA) Deposited in the Brain," *Society for Neuroscience Abstract Viewer and Itinerary Planner Abstract No. 328.9, 32nd Annual Meeting of the Society of Neuroscience*, Orlando, FL (Nov. 2-7, 2002).

Tomiyama et al. "A New Amyloid Beta Variant Favoring Oligomerization in Alzheimer's-Type Dementia," *Ann. Neurol*. 63(3):377-387, (2008).

Tsubuki et al. "Dutch, Flemish, Italian and Arctic Mutations of APP and Resistance of Abeta to Physiologically Relevant Proteolytic Degradation," *Lancet* 361(9373): 1957-1958, (2003).

Turner et al. "The Potential Exploitation of Plant Viral Translational Enhancers in Biotechnology for Increased Gene Expression," *Mol. Biotech*. 3:225-236, (1995).

Tusell et al. "Upregulation of p21Cipl in Activated Glial Cells," *Glia* 57(5):524-534, (2009).

Ueki et al. "Solid Phase Synthesis and Biological Activities of (Arg8)-Vasopressin Methylenedithioether," *Bioorg. Med. Chem. Lett*. 9:1767-1772, (1999).

Umana et al. "Engineered Glycoforms of an Antieuro-Blastoma Igg 1 With Optimized Antibody-Dependent Cellular Cytotoxic Activity," *Nature Biotech*. 17:176-180, (1999).

Urbanc et al. "Computer Simulations of Alzheimer's Amyloid Beta-Protein Folding and Assembly," *Curr. Alzheimer Res*. 3(5):493-504, (2006).

Urbanc et al. "In Silico Study of Amyloid Beta-Protein Folding and Oligomerization," *Proc. Natl. Acad. Sci. USA* 101:17345-17350, (2004).

Urbanc et al. "Molecular Dynamics Simulation of Amyloid Beta Dimer Formation," *Biophys. J*. 87(4):2310-2321, (2004).

Urlaub et al. "Isolation of Chinese Hamster Cell Mutants Deficient in Dihydrofolate Reductase Activity," *Proc. Natl. Acad. Sci. USA* 77:4216-4220, (1980).

Uto et al. "Determination of Urinary Tamm-Horsfall Protein by ELISA Using a Maleimide Method for Enzyme-Antibody Conjugation," *J. Immunol. Methods* 138:87-94, (1991).

Vajdos et al. "Comprehensive Functional Maps of the Antigen-binding Site of an Anti-ErbB2 Antibody Obtained with Shotgun Scanning Mutagenesis," Journal of Molecular Biology 320:415-428, (2002).

Valincius et al. "Soluble Amyloid Beta-Oligomers Affect Dielectric Membrane Properties by Bilayer Insertion and Domain Formation: Implications for Cell Toxicity," *Biophys. J*. 95(10):4845-4851, (2008).

Van Broeck et al. "Current Insights Into Molecular Mechanisms of Alzheimer Disease and Their Implications for Therapeutic Approaches," *Neurdegenerative Dis*. 4(5):349-365, (2007).

Van Broeckhoven et al. "Amyloid Beta Protein Precursor Gene and Hereditary Cerebral Hemorrhage With Amyloidosis (Dutch)" *Science* 248(4959):1120-1122, (1990).

Van Gool et al. "Concentrations of Amyloid-Beta Protein in Cerebrospinal Fluid Increase With Age in Patients Free From Neurodegenerative Disease," *Neurosci Lett*. 172(1-2):122124, (1994).

Vattemi et al. "Amyloid-Beta42 Is Preferentially Accumulated in Muscle Fibers of Patients With Sporadic Inclusion-Body Myositis," *Acta Neuropathol*. 117(5):569-574, (2009).

Veber et al. "The Design of Metabolically-Stable Peptide Analogs," *TINS* pp. 392-396, (1985).

Verhoeven et al. "Engineering of Antibodies," *Bioessays* 8(2):74-78, (1988).

Vestergaard et al. "Detection of Alzheimer's Amyloid Beta Aggregation by Capturing Molecular Trails of Individual Assemblies," *Biochem. Biophys. Res. Comm*. 377(2):725-728, (2008).

Vickers, "A Vaccine Against Alzheimer's Disease," *Drugs and Aging* 19:487-494, (2002).

Viola et al. "ADDLs Bind Selectively to Nerve Cell Surfaces in Receptor-Like Puncta," *Soc. for Neurosci. Abstract Viewer and Itinerary Planner Abstract No. 91.9, 32nd Annual meeting of the Society for Neuroscience*, Orlando, FL (Nov. 2-7, 2002).

Viola et al. "Immunolocalization of Oligomeric Abeta42 Binding to Primary Mouse Hippocampal Cells and B103 Rat Neuroblastoma Cells," *Society for Neuroscience Abstracts 29th Annual Meeting of the Society for Neuroscience*, Miami Beach, FL (Oct. 23-28, 1999).

Wahlstrom et al. "Secondary Structure Conversions of Alzheimer's a Beta(1-40) Peptide Induced by Membrane-Mimicking Detergents," *FEBS J*. 275:5117-5128, (2008).

Wakutani et al.,"Novel Amyloid Precursor Protein Gene Missense Mutation (D678N) in Probable Familial Alzheimer's Disease," *J. Neurol. Neurosurg. Psychiatry* 75(7):1039-1042, (2004).

Walensky et al. "Activation of Apoptosis In Vivo by a Hydrocarbon-Stapled BH3 Helix," *Science* 305:1466-1470, (2004).

Wallick et al. "Glycosylation of a V(H) residue of a Monoclonal Antibody Against Alpha-16) Dextran Increases Its Affinity for Antigen," *J. Exp. Med*. 168:1099-1109, (1988).

Wang et al "Soluble Oligomers of Abeta(1-42) Impair LTP in Rat Hippocampal Dentate Gyrus," *Society for Neuroscience Abstracts Abstract No. 663.18, 30th Annual Meeting of the Society of Neuroscience*, New Orleans, LA (Nov. 4-9, 2000).

Wang et al. "Direct and Selective Elimination of Specific Prions and Amyloids by 4,5-Dianilinophthalimide and Analogs," *Proc. Natl. Acad. Sci. USA* 105:7159-7164, (2008).

Wang et al. "Differential Effect of Abetal-42 Conformation and apoE Isoform on LTP," *Society for Neurosci. Abstracts 752.18, 31st Annual meeting of the Society for Neurosci*., San Diego, CA (Nov. 10-15, 2001).

Wang et al. "Soluble Oligomers of Beta Amyloid (1-42) Inhibit Long-Term Potentiation but Not Long-Term Depression in Rat Dentate Gyrus," *Brain Res*. 924(2):133-140, (2002).

Wang et al. "Development and Characterization of a TAPIR-like Mouse Monoclonal Antibody to Amyloid-Beta," *J. Alzheimer's Disease* 14(2):161-173, (2008).

Wang et al. "The Profile of Soluble Amyloid Beta Protein in Cultured Cell Medicine," *J. Biol. Chem*. 271(50):31894-31902, (1996).

Wang et al. "Per-6-Substituted-Per-6-Deoxy Beta-Cyclodextrins Inhibit the Formation of Beta-Amyloid Peptide Derived Soluble Oligomers," *J. Med. Chem*. 47:3329-3333, (2004).

Ward et al. "Binding Activities of a Repertoire of Single Immunoglobulin Variable Domains Secreted From *Escherichia coli*," *Nature* 341:544-546, (1989).

Weaver-Feldhaus et al. "Yeast Mating for Combinatorial Fab Library Generation and Surface Display," *FEBS Lett*. 564(2):24-34, (2004).

Weggen et al. "Evidence That Nonsteroidal Anti-Inflammatory Drugs Decrease Amyloid Beta-42 Production by Direct Modulation of Gamma-Secretase Activity," *J. Biol. Chem*. 276(34):31831-31837, (2003).

Weksler et al. "Patients With Alzheimer Disease Have Lower Levels of Serum Anti-Amyloid Peptide Antibodies Than Healthy Elderly Individuals," *Gerontology* 37:943-948, (2002).

Wels et al. "Synthesis of a Novel Potent Cyclic Peptide MC4-Ligand by Ring-Closing Metathesis," *Bioorg. Med. Chem*. 13:4221-4227, (2005).

Wermuth et al. "Glossary of Terms Used in Medicinal Chemistry," *Pure and Applied Chem*. 70:1129-1143, (1998).

Westlind-Danielsson et al., "Spontaneous In Vitro Formation of Supramolecular Beta-Amyloid Structures,'betaamy Balls' by Beta-Amyloid 1-40 Peptide," *Biochem*. 40(49):14736-43, (2001).

White et al. "Differential Effects of Oligomeric and Fibrillar Amyloid-Beta 1-42 on Astrocyte-Mediated Inflammation," *Neurbiol. of Disease* 18(3):459-465, (2005).

(56) References Cited

OTHER PUBLICATIONS

Wilcock et al. "Intraacranially Administered Anti-Abeta Antibodies Reduce Beta-Amyloid Deposition by Mechanisms Both Independent of and Associated With Microglial Activation," *J. Neurosci.* 23(9):3745-3751, (2003).
Wilcock et al. "Passive Immunotherapy Against Aβ in Aged App-Transgenic Mice Reverses Cognitive Deficits and Depletes Parenchymal Amyloid Deposits in Spite of Increased Vascular Amyloid and Microhemorrhage," *J Neuroinflammation* I (24):1-11, (2004).
Williamson et al. "Binding of Amyloid Beta-Peptide to Ganglioside Micelles Is Dependent on Histidine-13," *Biochem. J.* 397:483-490, (2006).
Wilson et al. "Free Fatty Acids Stimulate the Polymerization of Tau and Amyloid Beta Peptides In Vitro Evidence for a Common Effector in Pathogenesis in Alzheimer's Disease," *Am. J. Path.* 150(6):2181-2195, (1997).
Wiltfang et al. "Highly Conserved and Disease-Specific Patterns of Carboxyterminally Truncated A-Beta Peptides 1-37/38/39 in Addition to 1-40/42 in Alzheimer's Disease and in Patients With Chronic Neuroinflammation," *J. Neurochem.* 81:481-495, (2002).
Windisch et al. "The Role of Alpha-Synuclein in Neurodegenerative Diseases: A Potential Target for New Treatment Strategies," *Neuro-Degenerative Diseases* 5(3-4):218-221, (2008).
Winnacker, E-L., *From Genes to Clones: Introduction to Gene Technology* Table of Contents, VCH Publishers, (1987).
Wong et al. "Amyloid-Beta Membrane Binding and Permeabilization Are Distinct Processes Influenced Separately by Membrane Charge and Fluidity," *J. Mol. Biol.* 286(1):81-96, (2009).
Woodhouse et al. "Vaccination Strategies for Alzheimer's Disease: A New Hope?" *Drugs Aging* 24(2):107-119, (2007).
Wright et al. "Antibody Variable Region Glycosylation: Position Effects on Antigen Binding and Carbohydrate Structure," *EMBO J.* 10(10):2717-2723, (1991).
Wu et al. "Humanization of a Murine Monoclonal Antibody by Simultaneous Optimization of Framework and CDR Residues," *J. Mol. Biol.* 294:151-162, (1999).
Wu et al. "The Structure of Abeta42 C-Terminal Fragments Probed by a Combined Experimental and Theoretical Study," *J. Mol. Biol.* 287(2):492-501, (2009).
Wu et al. "Delivery Systems for Gene Therapy," *Biotherapy* 3:87-95, (1991).
Wu et al. "Receptor-Mediated In Vitro Gene Transformation by a Soluble DNA Carrier System," *J. Biol. Chem.* 262(10):4429-4432, (1987).
Wurth et al., "Mutations That Reduce Aggregation of the Alzheimer's Abeta42 Peptide: An Unbiased Search for the Sequence Determinants of Abeta Amyloidogenesis," *J. Mol. Biol.* 319(5):1279-1290, (2002).
Xia et al. "A Specific Enzyme-Linked Immunosorbent Assay for Measuring Beta-Amyloid Protein Oligomers in Human Plasma and Brain Tissue of Patients With Alzheimer Disease," *Archives of Neurology* pp. 66190-6199, (2009).
Xia et al. "Enhanced Production and Oligomerization Fo the 42-Residue Amyloid Beta-Protein by Chinese Hamster Ovary Cells Stably Expressing Mutant Presenilins," *J. Biol. Chem.* 272(12):7977-7982, (1997).
Xiao-Dong et al. "Effect of Inflammatory Responses in Microglia Induced by Oligomeric Beta-Amyloid 1-42 on Neuronal Cells," *Acta Anatomica Sinica* 39 (6):804-809, (2008).
Xu et al. "Gamma-Secretase Catalyzes Sequential Cleavages of the A Beta PP Transmembrane Domain," *J. Alzheimer's Disease* 16:211-224, (2009).
Yamamoto et al. "Environment- and Mutation-Dependent Aggregation Behavior of Alzheimer Amyloid Beta-Protein," *J. Neurochem.* 90:62-69, (2004).
Yamin et al. "Amyloid Beta-Protein Assembly as a Therapeutic Target of Alzheimer's Disease," *Curr. Pharm. Design* 14:3231-3246, (2008).

Yamin et al. "NMDA Receptor-Dependent Signaling Pathways That Underlie Amyloid Beta-Protein Disruption of LTP in the Hippocampus," *J. Neuroscience Res.* 87(8):1729-1736, (2009).
Yan et al. "Protection Mechanisms Against Abeta42 Aggregation," *Curr. Alzheimer Res.* 5(6):548-554, (2008).
Yan et al. "Roscovitine: A Novel Regulator of P/Q-Type Calcium Channels and Transmitter Release in Central Neurons," *J. Physiol.* 540(3):761-770, (2002).
Yang et al. "Amyloid Beta-Protein Monomer Folding: Free-Energy Surfaces Reveal Alloform-Specific Differences," *J. Mol. Biol.* 384(2):450-464, (2008).
Yang et al. "Fully Human Anti-Interleukin-8 Monoclonal Antibodies: Potential Therapeutics for the Treatment of Inflammatory Disease Status," *J. Leukocyte Biol.* 66:401-410, (1999).
Ye et al. "Protofibrils of Amyloid Beta-Protein Inhibit Specific K+ Currents in Neocortical Cultures," *Neurobiol. Disease* 13:177-190, (2003).
Yeh et al. "A Cell-Surface Antigen Which Is Present in the Ganglioside Fraction and Shared by Human Melanomas," *Int. J. Cancer* 29:269-275, (1982).
Yeh et al. "Cell Surface Antigens of Human Melanoma Identified by Monoclonal Antibody," *Proc. Natl. Acad. Sci. USA* 76(6):2927-2931, (1979).
Yoshinari et al. "Differential Effects of Immunosuppressants and Antibiotics on Human Monoclonal Antibody Production Is SCID Mouse Ascites by Five Heterohybridomas," *Hybridoma* 17(1):41-45, (1998).
Yoshitake et al. "Mild and Efficient Conjugation of Rabbit Fab and Horseradish Peroxide Using a Maleimide Compound and Its Use for Enzyme Immunoassay," *J. Biochem.* 92:1413-1424, (1982).
Young et al. "Oligomeric Amyloid-Beta 1-42 Activates Extracellular Signal Regulated Kinases ERKl and ERK2 of the Mitogen Activated Protein Kinase Pathway in SH-SY5YCELLS," *Neurobiol of Aging* 25:S150, (2004).
Youssef et al. "N-Truncated Amyloid-Beta Oligomers Induce Learning Impairment and Neuronal Apoptosis," *Neurobiol of Aging* 29:1319-1333, (2008).
Yu et al. "Structural Characterization of a Soluble Amyloid Beta-Peptide Oligomer," *Biochem.* 48:1870-1877, (2009).
Yun et al. "Role of Electrostatic Interactions in Amyloid Beta-Protein (Abeta) Oligomer Formation: A Discrete Molecular Dynamics Study," *Biophys. J.* 92(11):4064-4077, (2007).
Yun et al. "Amyloid-Beta 1-42 Reduces Neuronal Excitability I Nmouse Dentate Gyrus," *Neurosci. Lett.* 403: 162-165, (2006).
Zameer et al. "Anti-Oligomeric Abeta Single-Chain Variable Domain Antibody Blocks Abeta-Induced Toxicity Against Human Neuroblastoma Cells," *J. Mol. Biol.* 384(4):917-928, (2008).
Zarandi et al. "Synthesis of Abeta[1-42] and Its Derivatives With Improved Efficiency," *J. Peptide Sci.* 13(2):94-99, (2007).
Zhao et al. "Molecular Dynamics Simulations to Investigate the Aggregation Behaviors of the Abeta(L 7-42) Oligomers," *J. Biomol. Struct. Dyn.* 26(4):481-490, (2009).
Zhao et al. "Identification of Antihypertensive Drugs Which Inhibit Amyloid-Beta Protein Oligomerization," *J. Alzheimer's Dis.* 16(1):49-57, (2009).
Zheng et al. "Annular Structures as Intermediates in Fibril Formation of Alzheimer Abeta17-42," *J. Phys. Chem.* 112(22):6856-6865, (2008).
Zhu et al. "Phospholipases A2 Mediate Amyloid-Beta Peptide-Induced Mitochondrial Dysfunction," *J. Neurosci.* 26(43):11111-11119, (2006).
Zlokovic, B.V. "Clearing Amyloid Through the Blood-Brain Barrier," *J. Neurochem.* 89(40):807-811, (2004).
Zou et al. "A Novel Function of Monomeric Amyloid Beta-Protein Serving as an Antioxidant Molecule Against Metal-Induced Oxidative Damage," *J. Neurosci.* 22:4833-4841, (2002).
Zou et al. "Amyloid Beta-Protein (Abeta)1-40 Protects Neurons From Damage Induced by Abeta1-42 in Culture and in Rat Brain," *J. Neurochem.* 87(3):609-619, (2003).
Co-Pending U.S. Appl. No. 13/862,865, filed Apr. 15, 2013.
Co-Pending U.S. Appl. No. 13/893,780, filed May 14, 2013.
Co-Pending U.S. Appl. No. 14/792,500, Stefan Barghorn, filed Jul. 6, 2015.

(56) References Cited

OTHER PUBLICATIONS

Co-Pending U.S. Appl. No. 60/126,603, filed Mar. 25, 1999.
Declaration of Andreas Muhs in support of opposition dated Oct. 10, 2014, with attachments.
Declaration of Hartmut Engelmann in support of opposition dated Oct. 14, 2014, with attachments.
European Opposition of EP 06838873.5 (U.S. Pat. No. 1,976,877) by Genentech, Inc. and AC Immune SA dated Oct. 15, 2014, 35 pages.
European Patent Office Search Report for Application No. 09180982 dated May 31, 2010, 4 pages.
European Search Report for Application No. EP10178394.2, dated Jan. 31, 2011, 7 pages.
European Patent Office Action for Application No. 08716081.8 dated Dec. 22, 2011, 6 pages.
European Patent Office Action for Application No. 10178394.2 dated Mar. 2, 2012, 4 pages.
European Patent Office Action for Application No. 10178394.2 dated Aug. 22, 2012, 4 pages.
European Patent Office Action for Application No. 10179255.4 dated Jul. 21, 2014, 10 pages.
European Patent Office Action for Application No. 10179281.0 dated Jul. 21, 2014, 10 pages.
European Patent Office Action for Application No. 10179297.6 dated Jul. 21, 2014, 9 pages.
European Patent Office Action for Application No. 11715837.8 dated Oct. 10, 2014, (4 pages.
European Patent Office Action for Application No. 11745902.4 dated Jul. 14, 2015, 5 pages.
European Office Action dated Oct. 10, 2014 for Application No. 11715837.8, filed Apr. 13, 2011.
European Office Action dated Jul. 21, 2014 for Application No. 10179255.4 filed Feb. 2, 2004.
European Office Action dated Jul. 21, 2014 for Application No. 10179281.0 filed Feb. 2, 2004.
European Office Action dated Jul. 21, 2014 for Application No. 10179291.9 filed Feb. 2, 2004.
Final Office Action dated Oct. 1, 2012 for U.S. Appl. No. 13/102,713, filed May 6, 2011.
Final Office Action dated Sep. 11, 2012 for U.S. Appl. No. 13/188,034, filed Jul. 21, 2011.
Final Office Action dated Oct. 14, 2010 for U.S. Appl. No. 11/945,124, filed Nov. 26, 2001.
Final Office Action dated May 24, 2012 for U.S. Appl. No. 12/529,467, filed Jul. 27, 2010.
Final Office Action dated Nov. 26, 2013 for U.S. Appl. No. 13/085,891, filed Apr. 13, 2011.
Final Office Action dated Mar. 29, 2011 for U.S. Appl. No. 11/885,362, filed Apr. 17, 2008.
International Preliminary Report on Patentability and Written Opinion for Application No. PCT/EP2004/000927 dated Aug. 5, 2005, 11 pages.
International Preliminary Report on Patentability and Written Opinion for Application No. PCT/EP2006/011530 dated Jun. 3, 2008, 11 pages.
International Preliminary Report on Patentability and Written Opinion for Application No. PCT/EP2008/001548 dated Sep. 1, 2008, 11 pages.
International Preliminary Report on Patentability and Written Opinion for Application No. PCT/162009/006636 dated Jan. 25, 2011, 7 pages.
International Preliminary Report on Patentability and Written Opinion for Application No. PCT/US2006/046043 dated Jun. 30, 2008, 32 pages.
International Preliminary Report on Patentability and Written Opinion for Application No. PCT/US2006/046148 dated Jun. 3, 2008, 8 pages.
International Preliminary Report on Patentability and Written Opinion for Application No. PCT/US2007/085932 dated Jun. 3, 2009, 5 pages.
International Preliminary Report on Patentability and Written Opinion for Application No. PCT/US2008/065199 dated Dec. 1, 2009, 10 pages.
International Preliminary Report on Patentability and Written Opinion for Application No. PCT/US2008/065205 dated Dec. 1, 2009, 6 pages.
International Preliminary Report on Patentability and Written Opinion for Application No. PCT/IB2009/006636 dated Jan. 25, 2011, 7 pages.
International Preliminary Report on Patentability and Written Opinion for Application No. PCT/US2009/051721 dated Jan. 25, 2011, 7 pages.
International Search Report for Application No. PCT/EP2004/000927 dated Jun. 14, 2004, 4 pages.
International Search Report for Application No. PCT/EP2006/011530, dated Jun. 6, 2007, 7 pages.
International Search Report for Application No. PCT/EP2008/001548 dated Jul. 4, 2008, 3 pages.
International Search Report for Application No. PCT/EP2008/001549 dated Dec. 23, 2008, 6 pages.
International Search Report for Application No. PCT/IB2009/006636 dated Jan. 22, 2010, 6 pages.
International Search Report for Application No. 041650 dated Jun. 21, 2008, 16 pages.
International Search Report for Application No. PCT/US2006/046148 dated Jun. 19, 2007, 5 pages.
International Search Report for Application No. PCT/US2007/085932 dated Sep. 22, 2008, 3 pages.
International Search Report for Application No. PCT/US2008/065199 dated Sep. 26, 2008, 4 pages.
International Search Report for Application No. PCT/US2008/065205 dated Oct. 31, 2008, 3 pages.
International Search Report for Application No. PCT/US2009/051721 dated Mar. 16, 2010, 6 pages.
International Search Report for Application No. PCT/US2011/047622 dated Jan. 2, 2012, 6 pages.
Invitation to Pay Fees for Application No. PCT/EP2015/065362 dated Dec. 10, 2015, 10 pages.
Non-Final Office Action dated Feb. 10, 2011 for U.S. Appl. No. 11/574,844, filed Sep. 30, 2008.
Non-Final Office Action dated Jul. 14, 2011 for U.S. Appl. No. 11/574,847, filed Dec. 31, 2008.
Non-Final Office Action dated Jul. 22, 2010 for U.S. Appl. No. 11/885,362, filed Apr. 17, 2008.
Non-Final Office Action dated Mar. 3, 2010 for U.S. Appl. No. 11/945,124, filed Nov. 26, 2007.
Non-Final Office Action dated Jun. 6, 2012 for U.S. Appl. No. 12/509,315, filed Jul. 24, 2009.
Non-Final Office Action dated Feb. 14, 2014 for U.S. Appl. No. 12/529,467, filed Jul. 27, 2010.
Non-Final Office Action dated Dec. 6, 2011 for U.S. Appl. No. 12/529,467, filed Jul. 27, 2010.
Non-Final Office Action dated Apr. 19, 2012 for U.S. Appl. No. 13/102,713, flied May 6, 2011.
Non-Final Office Action dated Jan. 3, 2012 for U.S. Appl. No. 13/188,034, filed Jul. 21, 2011.
Non-Final Office Action dated Nov. 13, 2012 for U.S. Appl. No. 13/195,533, filed Aug. 1, 2011.
Notice of Allowance dated May 9, 2012 for U.S. Appl. No. 11/574,844, filed Sep. 30, 2008.
Notice of Allowance dated Feb. 10, 2012 for U.S. Appl. No. 11/574,847, filed Dec. 31, 2008.
Notice of Allowance dated Oct. 4, 2012 for U.S. Appl. No. 11/574,847, filed Dec. 31, 2008.
Notice of Allowance dated Mar. 5, 2012 for U.S. Appl. No. 11/945,124, filed Nov. 26, 2007.
Notice of Allowance dated Apr. 4, 2011 for U.S. Appl. No. 11/945,124, filed Nov. 26, 2007.
Notice of Allowance dated Oct. 4, 2012 for U.S. Appl. No. 11/945,124, filed Nov. 26, 2007.
Notice of Allowance dated Jul. 9, 2014 for U.S. Appl. No. 12/529,467, filed Jul. 21, 2011.

(56) References Cited

OTHER PUBLICATIONS

Notice of Allowance dated Oct. 29, 2014 for U.S. Appl. No. 13/085,891, filed Apr. 13, 2011.
Notice of Allowance dated Mar. 12, 2014 for U.S. Appl. No. 13/102,113, filed May 6, 2011.
Notice of Allowance dated Jun. 24, 2014 for U.S. Appl. No. 13/102,713, filed May 6, 2011.
Notice of Allowance dated Jun. 25, 2015 for U.S. Appl. No. 13/195,533, filed Aug. 1, 2011.
Notice of Allowance dated Feb. 3, 2016 for U.S. Appl. No. 13/862,865, filed Apr. 15, 2013.
Notice of Allowance dated Feb. 11, 2015 for U.S. Appl. No. 13/988,307, filed Mar. 7, 2014.
Notice of Allowance dated Feb. 10, 2010 for U.S. Appl. No. 14/513,837, filed Oct. 14, 2014.
Notice of Opposition for European Application No. 06707413/ Patent No. 1861422 dated Nov. 24, 2010.
Office Action dated Dec. 3, 2014 for U.S. Appl. No. 13/195,533, filed Aug. 1, 2011.
Office Action dated Jun. 4, 2015 for U.S. Appl. No. 13/862,865, filed Apr. 15, 2013.
Office Action dated Jan. 9, 2015 for U.S. Appl. No. 13/893,780, filed May 14, 2013.
Office Action dated Jul. 31, 2015 for U.S. Appl. No. 14/303,300, filed Jun. 12, 2014.
Office Action dated Nov. 9, 2015 for U.S. Appl. No. 14/513,837, filed Oct. 14, 2014.
Office Action dated Feb. 1, 2016 for U.S. Appl. No. 14/514,168, flied Oct. 14, 2014.
Opposition of EP 06838873.5 (Patent No. 1976877) by Genentech, Inc. and AC Immune S.A. in Europe dated Oct. 15, 2014, 35 pages.
Supplemental European Patent Office Search Report for Application No. 07864914.2 dated Apr. 28, 2010, 5 pages.
Supplemental European Search Report from European Patent Publication No. 2303920 dated Sep. 26, 2011, 5 pages.
Supplemental European Search Report for Application No. EP07864914.2, dated Apr. 28, 2010, 5 pages.
Supplemental European Search Report for Application No. EP2303920, dated Sep. 26, 2011, 3 pages.
United States Patent Office Action for U.S. Appl. No. 11/574,844 dated Feb. 2011, 11 pages.
United States Patent Office Action for U.S. Appl. No. 11/574,847 dated Jul. 14, 2011, 22 pages.
United States Patent Office Action for U.S. Appl. No. 11/574,876, dated Jan. 23, 2012, 17 pages.
United States Patent Office Action for U.S. Appl. No. 11/574,876 dated Nov. 15, 2012, 9 pages.
United States Patent Office Action for U.S. Appl. No. 11/885,362 dated Jul. 22, 2010, 10 pages.
United States Patent Office Action for U.S. Appl. No. 11/885,362 dated Mar. 29, 2011, 8 pages.
United States Patent Office Action for U.S. Appl. No. 11/885,362 dated Sep. 26, 2013, 11 pages.
United States Patent Office Action for U.S. Appl. No. 11/945,124 dated Mar. 3, 2010, 15 pages.
United States Patent Office Action for U.S. Appl. No. 11/945,124 dated Oct. 14, 2010, 8 pages.
United States Patent Office Action for U.S. Appl. No. 12/509,315 dated Jun. 6, 2012, 10 pages.
United States Patent Office Action for U.S. Appl. No. 12/509,325 dated Jun. 6, 2012, 14 pages.
United States Patent Office Action for U.S. Appl. No. 12/529,467 dated Dec. 6, 2011, 24 pages.
United States Patent Office Action for U.S. Appl. No. 12/529,467 dated May 24, 2012, 19 pages.
United States Patent Office Action for U.S. Appl. No. 12/529,467 dated Feb. 14, 2014, 17 pages.
United States Patent Office Action for U.S. Appl. No. 13/085,891 dated Apr. 18, 2013, 16 pages.
United States Patent Office Action for U.S. Appl. No. 13/085,891 dated Nov. 26, 2013, 10 pages.
United States Patent Office Action for U.S. Appl. No. 13/102,713 dated Apr. 19, 2012, 20 pages.
United States Patent Office Action for U.S. Appl. No. 13/102,713 dated Oct. 1, 2012 14 pages.
United States Patent Office Action for U.S. Appl. No. 13/188,034 dated Jan. 3, 2012, 35 pages.
United States Patent Office Action for U.S. Appl. No. 13/188,034 dated Sep. 2012, 18 pages.
United States Patent Office Action for U.S. Appl. No. 13/195,533 dated Nov. 13, 2012, 23 pages.
United States Patent Office Action for U.S. Appl. No. 13/195,533 dated Jul. 11, 2013, 21 pages.
United States Patent Office Action for U.S. Appl. No. 13/195,533 dated Dec. 3, 2014, 13 pages.
United States Patent Office Action for U.S. Appl. No. 13/195,533 dated Feb. 24, 2014, 9 pages.
United States Patent Office Action for U.S. Appl. No. 13/862,865 dated Jun. 4, 2015, 14 pages.
United States Patent Office Action for U.S. Appl. No. 13/893,780 dated Jan. 9, 2015, 8 pages.
United States Patent Office Action for U.S. Appl. No. 14/303,300 dated Jul. 31, 2015, 12 pages.
United States Patent Office Action for U.S. Appl. No. 14/514,168 dated Feb. 1, 2016, 8 pages.
United States Patent Office Notice of Allowance for U.S. Appl. No. 11/574,844 dated Aug. 11, 2011, 14 pages.
United States Patent Office Notice of Allowance for U.S. Appl. No. 11/574,844 dated May 9, 2012, 8 pages.
United States Patent Office Notice of Allowance for U.S. Appl. No. 11/574,876 dated Sep. 30, 2013, 11 pages.
United States Patent Office Notice of Allowance for U.S. Appl. No. 11/574,847 dated Feb. 10, 2012, 12 pages.
United States Patent Office Notice of Allowance for U.S. Appl. No. 11/574,847 dated Oct. 4, 2012, 8 pages.
United States Patent Office Notice of Allowance for U.S. Appl. No. 11/945,124 dated Apr. 4, 2011, 8 pages.
United States Patent Office Notice of Allowance for U.S. Appl. No. 11/945,124 dated Mar. 5, 2012, 7 pages.
United States Patent Office Notice of Allowance for U.S. Appl. No. 11/945,124 dated Oct. 9, 2012, 7 pages.
United States Patent Office Notice of Allowance for U.S. Appl. No. 12/529,467 dated Jul. 9, 2014,9 pages.
United States Patent Office Notice of Allowance for U.S. Appl. No. 13/085,891 dated Oct. 29, 2014, 10 pages.
United States Patent Office Notice of Allowance for U.S. Appl. No. 13/102,713 dated Mar. 14, 2014, 9 pages.
United States Patent Office Notice of Allowance for U.S. Appl. No. 13/102,713 dated Jun. 24, 2014, 7 pages.
United States Patent Notice of Allowance for U.S. Appl. No. 13/195,533 dated Jun. 25, 2015, 8 pages.
United States Patent Office Notice of Allowance for U.S. Appl. No. 13/862,865 dated Feb. 3, 2016, 9 pages.
Unite States Patent Office Notice of Allowance for U.S. Appl. No. 13/988,307 dated Feb. 11, 2015, 17 pages.
United States Patent Office Notice of Allowance for U.S. Appl. No. 14/513,837 dated Feb. 10, 2016, 7 pages.
Written Opinion for Application No. PCT/US2011/047622 dated Jan. 2, 2012, 8 pages.
Decision to Maintain the European Patent in Amended Form dated Sep. 8, 2016, for European Application No. 06838873.5, 2 pages.
Interlocutory Decision in Opposition Proceedings (Art. 101(3)(a) and 106(2) EPC, dated Feb. 3, 2016, for European Application No. 06838873.5, 93 pages.
Preliminary Decision of the Opposition Division and Summons to Attend Oral Proceedings, dated Aug. 3, 2015, for European Application No. 06838873.5, 23 pages.
Proprietor Response to Notice of Opposition Pursuant to Rule 79(1) EPC, dated Jun. 1, 2015, for European Application No. 06838873.5, 17 pages.

(56) References Cited

OTHER PUBLICATIONS

Queen, C. et al. "A Humanized Antibody That Binds to the Interleukin 2 Receptor," *Proc. Natl. Acad. Sci. USA* 86:10029-10033, (Dec. 1989).

Response to the Summons to Attend Oral Proceedings Pursuant to Rule 115(1) EPC of Aug. 3, 2015, dated Dec. 30, 2015, for European Application No. 06838873.5.

Shi, Y. et al. (2006, e-pub. Nov. 9, 2005). "Quantitative Determination of the Topological Propensities of Amyloidogenic Peptides," *Biophysical Chemistry* 120(1):56-61.

Withdraw of Opposition Letter, dated Dec. 30, 2015, for European Application No. 06838873.5, 2 pages.

Press Release (Jan. 30, 2019). "Roche to Discontinue Phase III CREAD 1 and 2 Clinical Studies of Crenezumab in Early Alzheimer's Diseas (AD) —Other Company Programmes in AD Continue," Media Release 3 pages.

1. Marker
2. Fibril preparation control
3. Fibril preparation ; + mMAb 6E10   ; 20h 37°C ; supernatant
4. Fibril preparation ; + mMAb 6E10   ; 20h 37°C ; pellet
5. Fibril preparation ; + mMAb 4G8    ; 20h 37°C ; supernatant
6. Fibril preparation ; + mMAb 4G8    ; 20h 37°C ; pellet
7. Fibril preparation ; + mMAb 8F5    ; 20h 37°C ; supernatant
8. Fibril preparation ; + mMAb 8F5    ; 20h 37°C ; pellet

VH_8F5

GAGGTGCAGCTGGTGGAGTCTGGGGGAGGCTTAGTGCAGCCTGGAGGGCCC
TGAAACTCTCCTGTGCAGCCTCTGGATTCACTTTCAGTAGCTATGGCATGTCT
TGGGTTCGCCAGACTCCAGACAAGAGGCTGGAATTGGTCGCAAGCATCAATA
GTAATGGTGGTAGCACCTATTATCCAGACAGTGTGAAGGGCCGATTCACCAT
CTCCAGAGACAATGCCAAGAACACCCTGTACCTGCAAATGAGCAGTCTGAAG
TCTGAGGACACAGCCATGTATTACTGTGCAAGTGGTGACTACTGGGGCCAAG
GCTCCACTCTCACAGTCTCCTCA    (SEQ ID NO:1)

GATGTTGTGATGACCCAAACTCCACTCTCCCTGCCTGTCAGTCTTGGAGATCA
AGCCTCCATCTCTTGCAGATCTAGTCAGAGCCTTGTATATAGTAATGGAGACA
CCTATTTACATTGGTACCTGCAGAAGCCAGGCCAGTCTCCAAAGCTCCTGATC
TACAAAGTTTCCAACCGATTTTCTGGGGTCCCAGACAGGTTCAGTGGCAGTG
GATCAGGGACAGATTTCACACTCAAGATCAGCAGAGTGGAGGCTGAGGATCT
GGGAGTTTATTTCTGCTCTCAAAGTACACATGTTCCTTGGACGTTCGGTGGAG
GCACCAAGCTAGAAATCAAACGG    (SEQ ID NO:2)

EVQLVESGGGLVQPGGSLKLSCAASGFTFSSYGMSWVRQTPDKRLELVASINSN
GGSTYYPDSVKGRFTISRDNAKNTLYLQMSSLKSEDTAMYYCASGDYWGQGST
LTVSS (SEQ ID NO:3)

CDR1 (VH) = SYGMS (SEQ ID NO:5)
CDR2 (VH) = SINSNGGSTYYPDSVKG (SEQ ID NO:6)
CDR3 (VH) = SGDY (SEQ ID NO:7)

DVVMTQTPLSLPVSLGDQASISCRSSQSLVYSNGDTYLHWYLQKPGQSPKLLIYK
VSNRFSGVPDRFSGSGSGTDFTLKISRVEAEDLGVYFCSQSTHVPWTFGGGTKLE
IKR (SEQ ID NO:4)

CDR1(VL) = RSSQSLVYSNGDTYLH (SEQ ID NO:8)
CDR2(VL) = KVSNRFS (SEQ ID NO:9)
CDR3(VL) = SQSTHVPWT (SEQ ID NO:10)

FIG.6B

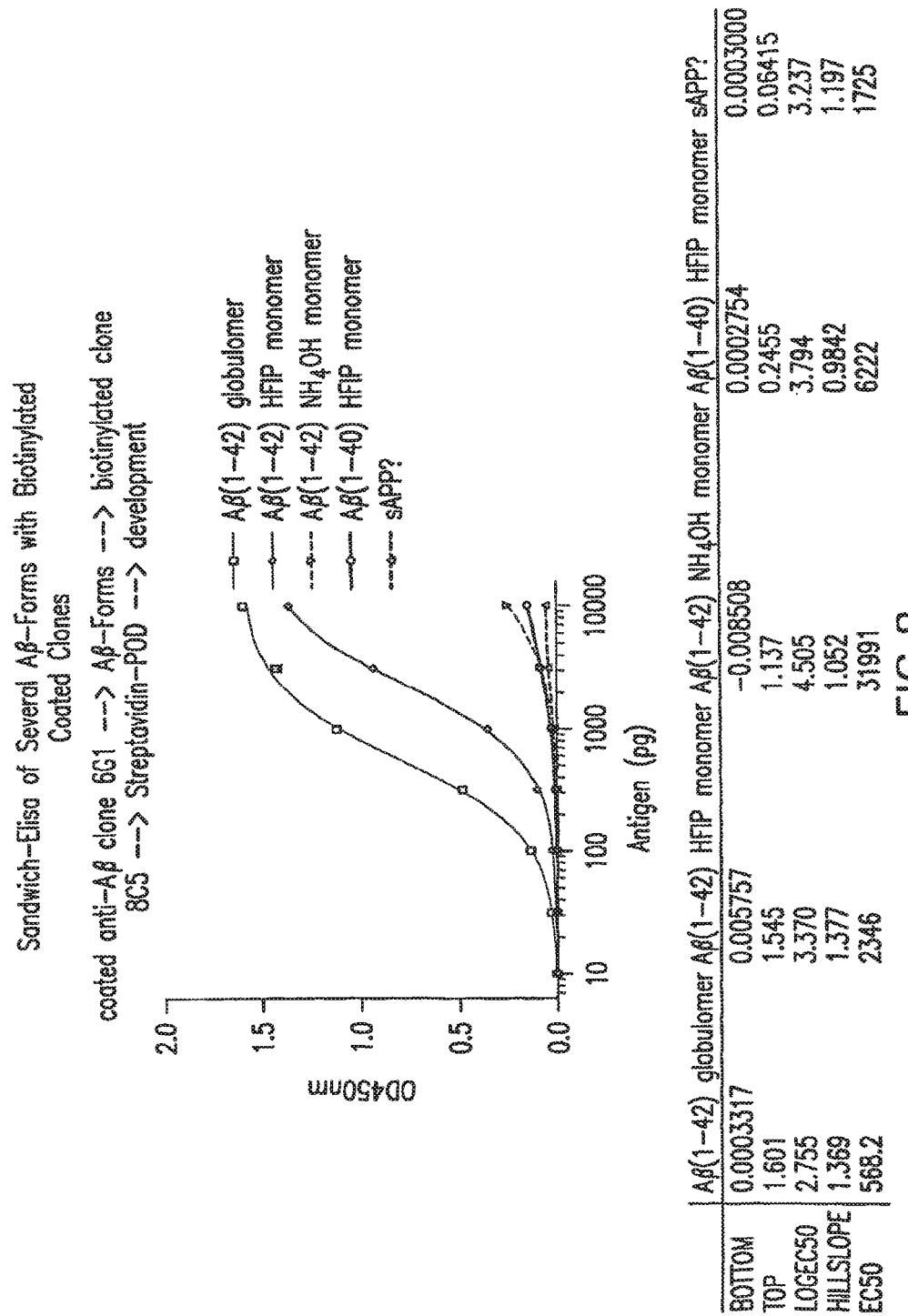

VH 8C5

GAGGTGCAGTTGGTGGAGTCTGGGGGAGGCTTAGTGCAGCCTGGAGGGTCCC
TGAAACTCTCCTGTACAGCCTCTGGATTCACTTTCAGTAGCTATGGCATGTCT
TGGGTTCGCCAGACTCCAGACAAGAGGCTGGAGTTGGTCGCAAGTATTAAAA
ATAATGGTGGTAGCACCTATTATCCAGACAGTTTGAAGGGCCGATTCACCAT
CTCCAGAGACAATGCCAAGAACACCCTGTACCTGCAAATGAGCAGTCTGAAG
TCTGAGGACACAGCCATGTATTATTGTGCAAGTGGGGATTACTGGGGCCAAG
GCACCACTCTCACAGTCTCCTCA (SEQ ID NO:11)

GATGTTGTGATGACCCAAACTCCACTCTCCCTGCCTGTCAGTCTTGGAGATCA
AGCCTCCATCTCTTGCAGATCTAGTCAGAGCCTTGTACACAGTAATGGAGAC
ACCTTTTTACATTGGTACCTGCAGAAGCCAGGCCAGTCTCCAAAGCTCCTGAT
CTACAAAGTTTCCAACCGATTTTCTGGGGTCCCAGACAGGTTCAGTGGCAGTG
GATCAGGGACAGATTTCACACTCAAGATCAGCAGAGTGGAGGCTGAGGATCT
GGGAATTTATTTCTGCTCTCAGAGTATACATGTTCCGTGGACGTTCGGTGGAG
GCACCAAGCTGGAAATCAAACGG (SEQ ID NO:12)

EVQLVESGGGLVQPGGSLKLSCTASGFTFS<u>SYGMS</u>WVRQTPDKRLELVAS<u>IKNN
GGSTYYPDLSLKG</u>RFTISRDNAKNTLYLQMSSLKSEDTAMYYCA<u>SGDY</u>WGQGTT
LTVSS (SEQ ID NO:19)

CDR1 (VH) = SYGMS (SEQ ID NO:13)

CDR2 (VH) = SIKNNGGSTYYPDSLKG (SEQ ID NO:14)

CDR3 (VH) = SGDY (SEQ ID NO:15)

DVVMTQTPLSLPVSLGDQASISC<u>RSSQSLVHSNGDTFLH</u>WYLQKPGQSPKLLIY<u>K
VSNRFS</u>GVPDRFSGSGSGTDFTLKISRVEAEDLGIYFC<u>SQSIHVPWT</u>FGGGTKLEI
KR (SEQ ID NO:20)

CDR1 (VL) = RSSQSLVHSNGDTFLH (SEQ ID NO:16)

CDR2 (VL) = KVSNRFS (SEQ ID NO:17)

CDR3 (VL) = SQSIHVPWT (SEQ ID NO:18)

FIG.10B

MONOCLONAL ANTIBODIES AGAINST AMYLOID BETA PROTEIN AND USES THEREOF

RELATED APPLICATIONS

This application is a divisional of U.S. patent application Ser. No. 13/188,034 filed on Jul. 21, 2011, which is a divisional application of U.S. patent application Ser. No. 11/574,847 filed on Dec. 31, 2008, now U.S. Pat. No. 8,497,072, which is a U.S. national phase application under 35 U.S.C. § 371 of International Application No. PCT/US2006/046148, filed on Nov. 30, 2006, which claims the priority benefit of U.S. Provisional Application No. 60/778,950 filed on Mar. 3, 2006 and U.S. Provisional Application No. 60/740,866 filed on Nov. 30, 2005, the disclosures of all of which are herein incorporated by reference in their entireties.

STATEMENT REGARDING THE SEQUENCE LISTING

The content of the following submission on ASCII text file is incorporated herein by reference in its entirety: a computer readable form (CRF) of the Sequence Listing (file name: 146392037811seqlist.txt, date recorded: Oct. 26, 2017, size: 15 KB).

BACKGROUND OF THE INVENTION

Technical Field

The subject invention relates to monoclonal antibodies (e.g., 8F5 and BC5) that may be used, for example, in the prevention, treatment and diagnosis of Alzheimer's Disease or other neurodegenerative disorders.

BACKGROUND INFORMATION

Alzheimer's Disease (AD) is a neurodegenerative disorder characterized by a progressive loss of cognitive abilities and by characteristic neuropathological features comprising amyloid deposits, neurofibrillary tangles and neuronal loss in several regions of the brain see Hardy and Selkoe (Science 297, 353 (2002); Mattson (Nature 431, 7004 (2004). The principal constituents of amyloid deposits are amyloid beta-peptides (Aβ), with the 42 amino acid-long type (Aβ1-42) being the most prominent.

In particular, amyloid β(1-42) protein is a polypeptide having 42 amino acids which is derived from the amyloid precursor protein (APP) by proteolytic processing. This also includes, in addition to human variants, isoforms of the amyloid β(1-42) protein present in organisms other than humans, in particular, other mammals, especially rats. This protein, which tends to polymerize in an aqueous environment, may be present in very different molecular forms.

A simple correlation of the deposition of insoluble protein with the occurrence or progression of dementia disorders such as, for example, Alzheimer's disease, has proved to be unconvincing (Terry et al., Ann. Neurol. 30, 572-580 (1991); Dickson et al., Neurobiol. Aging 16, 285-298 (1995)). In contrast, the loss of synapses and cognitive perception seems to correlate better with soluble forms of Aβ(1-42) (Lue et al., Am. J. Pathol. 155, 853-862 (1999); McLean et al., Ann. Neurol. 46, 860-866 (1999)).

Although polyclonal and monoclonal antibodies have been raised in the past against Aβ(1-42), none have proven to produce the desired therapeutic effect without also causing serious side effects in animals and/or humans. For example, passive immunization results from preclinical studies in very old APP23 mice which received a N-terminal directed anti-Aβ(1-42) antibody once weekly for 5 months indicate therapeutically relevant side effect. In particular, these mice showed an increase in number and severity of microhemorrhages compared to saline-treated mice (Pfeifer et al., Science 2002 298:1379). A similar increase in hemorrhage was recently also described for very old (>24 months) Tg2576 and PDAPP mice (Wilcock et al., J Neuroscience 2003, 23: 3745-51; Racke et al., J Neuroscience 2005, 25:629-636). In both strains, injection of anti-Aβ(1-42) resulted in a significant increase of microhemorrhages. Thus, a tremendous therapeutic need exists for the development of biologics that prevent or slow down the progression of the disease without inducing negative and potentially lethal effects on the human body. Such need is particularly evident in view of the increasing longevity of the general population and, with this increase, an associated rise in the number of patents annually diagnosed with Alzheimer's Disease. Further, such antibodies will allow for proper diagnosis of Alzheimer's Disease in a patient experiencing symptoms thereof, a diagnosis which can only be confirmed upon autopsy at the present time. Additionally, the antibodies will allow for the elucidation of the biological properties of the proteins and other biological factors responsible for this debilitating disease.

All patents and publications referred to herein are hereby incorporated in their entirety by reference.

SUMMARY OF THE INVENTION

The present invention includes an isolated antibody that binds with greater specificity to an amyloid beta (Aβ) protein globulomer than to an amyloid beta protein monomer. Thus, preferential binding is observed. The antibody may be, for example, a monoclonal antibody such as 8F5 or 8C5. The ratio of binding specificity to the globulomer versus the monomer is at least 1.4. In particular, the ratio is preferably at least about 1.4 to at least about 16.9. (A ratio of 1.0-17.5 including the endpoints) is also considered to fall within the scope of the present invention as well as decimal percentages thereof. For example, 1.1, 1.2, 1.3, . . . , 2.0, 2.1, 2.2 . . . , 17.1, 17.2, 17.3, 17.4, 17.5 as well as all full integers in between, and percentages thereof are considered to fall within the scope of the present invention.) The amyloid beta protein monomer may be, for example, Aβ(1-42) monomer or Aβ(1-40) monomer.

Further, the present invention also encompasses monoclonal antibody (referred to herein, as "8F5") produced by a hybridoma having American Type Culture Collection designation number PTA-7238 as well as the hybridoma that produces this monoclonal antibody (i.e., 8F5). Also, the present invention includes a monoclonal antibody (referred to herein as "8C5") produced by a hybridoma having American Type Culture Collection designation number PTA-7407 as well as the hybridoma that produces this monoclonal antibody (i.e., 8C5).

Additionally, the present invention includes a monoclonal antibody comprising a variable heavy chain encoded by SEQ ID NO:1. This antibody may be murine, human or humanized.

Further, the present invention includes a monoclonal antibody comprising a variable light chain encoded by SEQ ID NO:2. This antibody may also be murine, human or humanized. The antibody may further comprise a variable light heavy chain encoded by SEQ ID NO:1 and may be human or humanized.

Moreover, the present invention includes a monoclonal antibody comprising SEQ ID NO:3. The antibody may be murine, human or humanized.

Further, the present invention encompasses a monoclonal antibody comprising SEQ ID NO:4. This antibody may be murine, human or humanized. This antibody may further comprise SEQ ID NO:3 and may be murine, human or humanized.

Additionally, the present invention includes a monoclonal antibody comprising a variable heavy chain encoded by SEQ ID NO:11. This antibody may be murine, human or humanized.

Further, the present invention includes a monoclonal antibody comprising a variable light chain encoded by SEQ ID NO:12. This antibody may also be murine, human or humanized. The antibody may further comprise a variable heavy chain encoded by SEQ ID NO:11 and may be human or humanized.

Moreover, the present invention includes a monoclonal antibody comprising SEQ ID NO:19. The antibody may be murine, human or humanized.

Further, the present invention encompasses a monoclonal antibody comprising SEQ ID NO:20. This antibody may be murine, human or humanized. This antibody may further comprise SEQ ID NO:19 and may be murine, human or humanized.

The present invention also includes an isolated, antibody which binds with greater specificity to an amyloid be protein globulomer than to an amyloid beta protein fibril. This antibody may be, for example, monoclonal and may be the monoclonal antibody produced by the hybridoma having American Type Culture Collection designation number PTA-7243 or the hybridoma having American Type Culture Collection PTA-7407. The hybridomas producing these monoclonal antibodies also fall within the scope of the present invention.

Further, the present invention includes an antibody in which at least one of the complementarity determining regions (CDRs) of the variable heavy chain is selected from the group consisting of SEQ ID NO:5, SEQ ID NO:6 and SEQ ID NO:7.

Moreover, the present invention also includes an antibody in which at least one of the CDRs of the variable light chain is selected from the group consisting of SEQ ID NO:8, SEQ ID NO:9 and SEQ ID NO:10. This antibody may further comprise at least one CDR of the variable heavy chain selected from the group consisting of SEQ ID NO:5, SEQ ID NO:6 and SEQ ID NO:7.

The present invention also includes an antibody in which at least one of the CDRs of the variable heavy chain is selected from the group consisting of SEQ ID NO:13, SEQ ID NO:14 and SEQ ID NO:15.

Further, the present invention also encompasses an antibody in which at least one of the CDRs of the variable light chain is selected from the group consisting of SEQ ID NO:16, SEQ ID NO:17 and SEQ ID NO:18. This antibody may further comprises at least one CDR of the variable heavy chain selected from the group consisting of SEQ ID NO:13, SEQ ID NO:14 and SEQ ID NO:15.

Additionally, the present invention encompasses a method of treating or preventing Alzheimer's Disease in a patient in need of the treatment or prevention. This method comprises administering any one or more of the isolated antibodies described above to the patient in an amount sufficient to effect the treatment or prevention.

The isolated antibody may be administered, for example, via a route selected from the group consisting of intramuscular administration, intravenous administration and subcutaneous administration.

The present invention also includes a method of diagnosing Alzheimer's Disease in a patient suspected of having this disease. This method comprises the steps of: 1) isolating a biological sample from the patient; 2) contacting the biological sample with at least one of the antibodies described above for a time and under conditions sufficient for formation of antigen/antibody complexes; and 3) detecting presence of the antigen/antibody complexes in said sample, presence of the complexes indicating a diagnosis of Alzheimer's Disease in the patient. The antigen may be, for example, a globulomer or a portion or fragment thereof which has the same functional properties as the full globulomer (e.g., binding activity).

Further, the present invention includes another method of diagnosing Alzheimer's Disease in a patient suspected of having this disease. This method comprises the steps of: 1) isolating a biological sample from the patient; 2) contacting the biological sample with an antigen for a time and under conditions sufficient for the formation of antibody/antigen complexes; 3) adding a conjugate to the resulting antibody/antigen complexes for a time and under conditions sufficient to allow the conjugate to bind to the bound antibody, wherein the conjugate comprises one of the antibodies described above, attached to a signal generating compound capable of generating a detectable signal; and 4) detecting the presence of an antibody which may be present in the biological sample, by detecting a signal generated by the signal generating compound, the signal indicating a diagnosis of Alzheimer's Disease in the patient. The antigen may be a globulomer or a portion or fragment thereof having the same functional properties as the full globulomer (e.g., binding activity).

The present invention includes an additional method of diagnosing Alzheimer's Disease in a patient suspected of having Alzheimer's Disease. This method comprises the steps of: 1) isolating a biological sample from the patient; 2) contacting the biological sample with anti-antibody, wherein the anti-antibody is specific for one of the antibodies described above, for a time and under conditions sufficient to allow for formation of anti-antibody/antibody complexes, the complexes containing antibody present in the biological sample; 2) adding a conjugate to the resulting anti-antibody/antibody complexes for a time and under conditions sufficient to allow the conjugate to bind to bound antibody, wherein the conjugate comprises an antigen, which binds to a signal generating compound capable of generating a detectable signal; and 3) detecting a signal generated by the signal generating compound, the signal indicating a diagnosis of Alzheimer's Disease in the patient.

Further, the present invention includes a composition comprising any one or more of the antibodies described above (e.g., 8F5 and 8C5).

The present invention includes another method of preventing or treating Alzheimer's Disease in a patient in need of such prevention or treatment. This method comprises the step of administering the composition described directly above to the patient in an amount sufficient to effect the prevention or treatment.

Additionally, the present invention encompasses a vaccine comprising at least one of the antibodies described above and a pharmaceutically acceptable adjuvant.

Moreover, the present invention includes a further method of preventing or treating Alzheimer's Disease in a patient in need of such prevention or treatment. This method comprises the step of administering the vaccine noted above to the patient in an amount sufficient to effect the prevention or treatment.

Further, the present invention encompasses a method of identifying compounds suitable for active immunization of a patient predicted to develop Alzheimer's Disease. This method comprises: 1) exposing one or more compounds of interest to one or more of the antibodies described above for a time and under conditions sufficient for the one or more compounds to bind to the antibody or antibodies; 2) identifying those compounds which bind to the antibody or antibodies, the identified compounds to be used in active immunization in a patient predicted to develop Alzheimer's Disease.

Also, the present invention includes a kit comprising: a) at least one of the isolated antibodies described above and b) a conjugate comprising an antibody attached to a signal-generating compound, wherein the antibody of the conjugate is different from the isolated antibody. The kit may also include a package insert with instructions as to how the components of the kit are to be utilized.

The present invention also encompasses a kit comprising: a) an anti-antibody to one of the antibodies described above and b) a conjugate comprising an antigen attached to a signal-generating compound. The antigen may be a globulomer or a fragment or portion thereof having the same functional characteristics as the globulomer (e.g., binding activity). Again, the kit may also include a package insert with instructions as to how the components of the kit are to be utilized.

BRIEF DESCRIPTION OF THE DRAWINGS

FIG. 5A illustrates the DNA sequence (SEQ ID NO:1) of the variable heavy chain encoding the monoclonal antibody referred to herein as "8F5", and FIG. 5B illustrates the DNA sequence (SEQ ID NO:2) of the variable light chain encoding the monoclonal antibody 8F5. (Complementarity determining regions (CDRs) are underlined in each sequence; see also FIGS. 6A-6B.)

FIG. 6A illustrates the amino acid sequence (SEQ ID NO:3) of the variable heavy chain of monoclonal antibody 8F5, and FIG. 6B illustrates the amino acid sequence (SEQ ID NO:4) of the variable light chain of monoclonal antibody 8F5. One CDR of the variable heavy chain is represented by the amino acid sequence SYGMS (SEQ ID NO:5). Another CDR of the variable heavy chain is represented by the amino acid sequence SINSNGGSTYYPDSVKG (SEQ ID NO:6), and another CDR of the variable heavy chain is represented by the amino acid sequence SGDY (SEQ ID NO:7). One CDR of the variable light chain is represented by the amino acid sequence RSSQSLVYSNGDTYLH (SEQ ID NO:8). Another CDR of the variable light chain is represented by the amino acid sequence KVSNRFS (SEQ ID NO:9), and another CDR of the variable light chain is represented by the amino acid sequence SQSTHVPWT (SEQ ID NO:10). All of the above-described CDRs are underlined in FIG. 6A and FIG. 6B.

FIG. 7A illustrates verification of amyloid deposits by Congo Red staining as plaques in brain tissue and as cerebral amyloid angiopathy (CAA) in brain vessels in the APP transgenic mouse line Tg2576 and in an AD patient (RZ55). FIG. 7B illustrates that the staining of parenchymal deposits of Aß (amyloid plaques) in an AD patient (RZ16) occurs only with 6G1 and the commercially available antibody 6E10 while 8F5 and 8C5 show considerably weaker staining. FIG. 7C illustrates that the strong staining of parenchymal deposits of Aβ (amyloid plaques) in TG2576 mice occurs only with 6G1 and the commercially available antibody 6E10 while 8F5 and 8C5 show considerably weaker staining. FIGS. 7D-7G illustrate the quantification of the analysis of Aβ plaque staining in the histological images using image analysis. Optical density values (0%=no staining) were calculated from the greyscale values of plaques subtracted by greyscale values of background tissue. FIG. 7D=binding of 0.7 µg ml antibody in Tg2576 mice; FIG. 7E=binding of 0.07-0.7 µg/ml antibody in APP/L mice; FIG. 7F=binding of 0.7 µg/ml antibody in an AD patient (RZ55); and FIG. 7G=binding of 0.07-0.7 µg/ml antibody in an AD patient (RZ16)) The differences between staining of the commercially available antibodies 6E10 (starts) and 4G8 (circles) and antibodies 6G1, 8C5 and 8F5 (one asterisk/circle: $p<0.05$, two asterisks/circles: $p<0.01$, and three asterisks/circles: $p<0.001$ versus control; post-hoc Bonferroni's t-test after ANOVA with $p<0.001$) were statistically evaluated FIG. 7D and FIG. 7E). In FIG. 7E and FIG. 7G, the antibodies 8C5 and 8F5 always showed significantly less staining than the commercially available antibodies 6E10 and 4G8 ($p<0.05$ in post-hoc t-test after $p<0.001$ in ANOVA). FIG. 7H illustrates that the strong staining of vascular deposits of Aβ (arrows) occurs only with 6G1 and the commercially available antibody 6E10 while staining with 8F5 or 8C5 was much weaker. A qualitatively similar situation was found in Tg2576 mice (not shown here).

FIG. 8 illustrates the selectivity of 8C5 for globulomers versus Aβ(1-42) monomers, Aβ(1-40) and sAPP. Selectivity factors for 8C5 can be calculated as ratios between EC50 values (versus Aβ(1-42) monomer in HFIP: 2346/568.2=4.1; versus Aβ(1-42) monomer in NH$_4$OH: >100; versus Aβ (1-40) monomer: >100; versus sAPP: >100)

FIG. 9A illustrates the nucleotide sequence (SEQ ID NO:11) encoding the heavy chain of 8C5 and FIG. 9B illustrates the nucleotide sequence (SEQ ID NO:12) encoding the light chain of 8C5. The nucleotide sequences encoding the corresponding CDRs, noted in FIG. 10A and FIG. 10B, are underlined.

FIG. 10A illustrates the amino acid sequence (SEQ ID NO:19) of the variable heavy chain of monoclonal antibody 8C5, and FIG. 10B illustrates the amino acid sequence (SEQ ID NO:20) of the variable light chain of monoclonal antibody 8F5. One CDR of the variable heavy chain is represented by the amino acid sequence SYGMS (SEQ ID NO:13). Another CDR of the variable heavy chain is represented by the amino acid sequence SIKNNGGSTYYPD-SLKG (SEQ ID NO:14), and another CDR of the variable heavy chain is represented by the amino acid sequence SGDY (SEQ ID NO:15). One CDR of the variable light chain is represented by the amino acid sequence RSSQS-LVHSNGDTFLH (SEQ ID NO:16). Another CDR of the variable light chain is represented by the amino acid sequence KVSNRFS (SEQ ID NO:17), and another CDR of the variable light chain is represented by the amino acid sequence SQSIHVPWT (SEQ ID NO:18). All of the above-described CDRs are underlined in FIG. 10A and FIG. 10B.

DETAILED DESCRIPTION OF THE INVENTION

Figure 1:
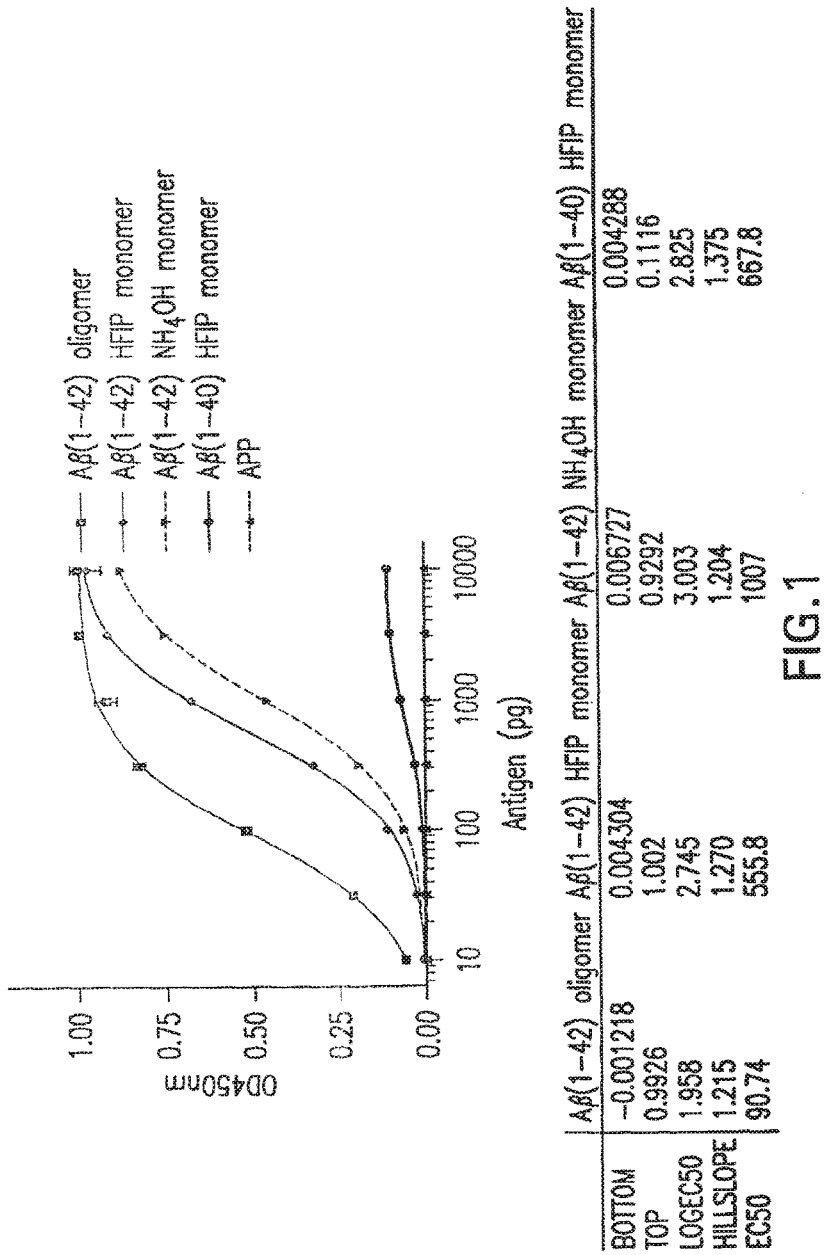
FIG. 1 illustrates the selectivity of 8F5 for globulomers versus Aß(1-42) monomers, Aß(1-40) and sAPP. Selectivity factors for 8F5 can be calculated as ratios between EC50 values (versus Aß(1-42) monomer in HFIP: 555.8/90.74=6.1; versus Aß(1-42) monomer in $NH_4OH$: 1007/90.74=11.1; versus Aß(1-40) monomer: 667.8/90.74=7.4 versus sAPP: >100)

The present invention relates to a monoclonal antibody, referred to herein as "8F5" as well as other related antibodies (e.g., 8C5). These antibodies may be used, for example, in the diagnosis, prevention and treatment of Alzheimer's Diseases and other neurodegenerative disorders.

Monoclonal antibody 8F5 as well as monoclonal antibody 8C5 have many interesting properties which allow them to be extremely interesting therapeutic candidates as well as extremely useful diagnostic candidates. For example, monoclonal antibodies 8F5 and 8C5 have preferential binding for Aβ(1-42) globulomers as compared with monomers or fibrils.

The term "Aβ(X-Y)" herein refers to the amino acid sequence from amino acid position X to amino acid position Y of the human amyloid β protein including both X and Y and, in particular, refers to the amino acid sequence from amino acid position X to amino acid position Y of the amino acid sequence DAEFRHDSGY EVHHQKLVFF AEDVG-SNKGA IIGLMVGGVV IA (SEQ ID NO. 21) or any of its naturally occurring variants, in particular, those with at least one mutation selected from the group consisting of A2T, H6R, D7N, A21G ("Flemish"), E22G ("Arctic"), E22Q ("Dutch"), E22K ("Italian"), D23N ("Iowa"), A42T and A42V wherein the numbers are relative to the start position of the Aβ peptide, including both position X and position Y or a sequence with up to three additional amino acid substitutions none of which may prevent globulomer formation. An "additional" amino acid substitution is defined herein as any deviation from the canonical sequence that is not found in nature.

More specifically, the term "Aβ(1-42)" herein refers to the amino acid sequence from amino acid position 1 to amino acid position 42 of the human amyloid β protein including both 1 and 42 and, in particular, refers to the amino acid sequence from amino acid position 1 to amino acid position 42 of the amino acid sequence DAEFRHDSGY EVH-HQKLVFF AEDVGSNKGA IIGLMVGGVV IA (SEQ ID NO. 21) (corresponding to amino acid positions 1 to 42) or any of its naturally occurring variants. Such variants may be, for example, those with at least one mutation selected from the group consisting of A2T, H6R, D7N, A21G ("Flemish"), E22G ("Arctic"), E22Q ("Dutch"), E22K ("Italian"), D23N ("Iowa"), A42T and A42V wherein the numbers are relative to the start of the Aβ peptide, including both 1 and 42 or a sequence with up to three additional amino acid substitutions none of which may prevent globulomer formation. Likewise, the term "Aβ(1-40)" here refers to the amino acid sequence from amino acid position 1 to amino acid position 40 of the human amyloid β protein including both 1 and 40 and refers, in particular, to the amino acid sequence from amino acid position 1 to amino acid position 40 of the amino acid sequence DAEFRHDSGY EVHHQKLVFF AEDVG-SNKGA IIGLMVGGVV (SEQ ID NO.: 22) or any of its naturally occurring variants. Such variants include, for example, those with at least one mutation selected from the group consisting of A2T, H6R, D7N, A21G ("Flemish"), E22G ("Arctic"), E22Q ("Dutch"), E22K ("Italian"), and D23N ("Iowa") wherein the numbers are relative to the start position of the Aβ peptide, including both 1 and 40 or a sequence with up to three additional amino acid substitutions none of which may prevent globulomer formation.

The term "Aβ(X-Y) globulomer" (also known as "Aβ(X-Y) globular oligomer") herein refers to a soluble, globular, non-covalent association of Aβ(X-Y) peptides, as defined above, possessing homogeneity and distinct physical characteristics. The Aβ(X-Y) globulomers are stable, non-fibrillar, oligomeric assemblies of Aβ(X-Y) peptides which are obtainable by incubation with anionic detergents. In contrast to monomer and fibrils, these globulomers are characterized by defined assembly numbers of subunits (e.g., early assembly forms, n=3-6, oligomers A", and late assembly forms, n=12-14, "oligomers B", as described in PCT International Application Publication No. WO 04/067561). The globulomers have a 3-dimensional globular type structure ("molten globule, see Barghorn et al., 2005, J Neurochem, 95, 834-847). They may be further characterized by one or more of the following features:

cleavability of N-terminal amino acids X-23 with promiscuous proteases (such as thermolysin or endoproteinase GluC) yielding truncated forms Aβ(X-Y) globulomers;

non-accessibility of C-terminal amino acids 24-Y promiscuous proteases and antibodies; and truncated forms of these Aβ(X-Y) globulomers maintain the 3-dimensional core structure of the globulomers with a better accessibility of the core epitope Aβ(20-Y) in its globulomer conformation.

According to the invention and, in particular, for the purpose of assessing the binding affinities of the antibodies of the present invention, the term "Aβ(X-Y) globulomer" herein refers to a product which is obtainable by a process as described in International Application Publication No. WO 04/067561, which is incorporated herein in its entirety by reference. The process comprises unfolding a natural, recombinant or synthetic Aβ(X-Y) peptide or a derivative thereof; exposing the at least partially unfolded Aβ(X-Y) peptide or derivative thereof to a detergent, reducing the detergent action and continuing incubation.

For the purpose of unfolding the peptide, hydrogen bond-breaking agents such as, for example, hexafluoroisopropanol (HFIP) may be allowed to act on the protein. Times of action of a few minutes, for example about 10 to 60 minutes, are sufficient when the temperature of action is from about 20 to 50° C. and, in particular, about 35 to 40° C. Subsequent dissolution of the residue evaporated to dryness, preferably in concentrated form, in suitable organic solvents miscible with aqueous buffers such as, for example, dimethyl sulfoxide (DMSO), results in a suspension of the at least partially unfolded peptide or derivative thereof which can be used subsequently. If required, the stock suspension may be stored at low temperature, for example, at about −20° C. for an interim period.

Alternatively, the peptide or the derivative thereof may be taken up in slightly acidic, preferably aqueous, solution, for example, a solution of about 10 mM aqueous HCl. After an incubation time of approximately a few minutes, insoluble components are removed by centrifugation. A few minutes at 10,000 g is expedient. These method steps are preferably carried out at room temperature, i.e., a temperature in the range of from 20 to 30° C. The supernatant obtained after centrifugation contains the Aβ(X-Y) peptide or a derivative thereof and may be stored at low temperature, for example at about −20° C., for an interim period.

The following exposure to a detergent relates to oligomerization of the peptide or the derivative thereof to give the intermediate type of oligomers (in International Application Publication. No. WO 04/067561 referred to as oligomers A). For this purpose, a detergent is allowed to act on the, optionally, at least partially unfolded peptide or derivative thereof until sufficient intermediate oligomer has been produced. Preference is given to using ionic detergents, in particular, anionic detergents.

According to a particular embodiment, a detergent of the formula (I):

is used, in which the radical "R" is unbranched or branched alkyl having from 6 to 20 and preferably 10 to 14 carbon atoms or unbranched or branched alkenyl having from 6 to 20 and preferably 10 to 14 carbon atoms, and the radical "X" is an acidic group or salt thereof with X being preferably selected from among —COO$^-$M$^+$, —SO$_3$$^-$M$^+$ and is, most preferably, —OSO$_3$$^-$M$^+$ and M$^+$ is a hydrogen cation or an inorganic or organic cation preferably selected from alkali metal cations, alkaline earth metal cations and ammonium cations. Most advantageous are detergents of the formula (I) in which R is an unbranched alkyl of which alk-1-yl radicals must be mentioned, in particular. Particular preference is given to sodium dodecyl sulfate (SDS). Lauric acid and oleic acid can also be used advantageously. The sodium salt of the detergent lauroylsarcosin (also known as sarkosyl NL-30 or Gardo®) is also particularly advantageous.

The time of detergent action, in particular, depends on whether, and if yes, to what extent the peptide or derivative thereof subjected to oligomerization has unfolded. If, according to the unfolding step, the peptide or derivative thereof has been treated beforehand with a hydrogen bond-breaking agent (i.e., in particular with hexafluoroisopropanol), times of action in the range of a few hours, advantageously from about 1 to 20 and, in particular, from about 2 to 10 hours, are sufficient when the temperature of action is about 20 to 50° C. and, in particular, from about 35 to 40° C. If a less unfolded or an essentially not unfolded peptide or derivative thereof is the starting point, correspondingly longer times of action are expedient. If the peptide or derivative thereof has been pretreated, for example, according to the procedure indicated above as an alternative to the HFIP treatment or said peptide or derivative thereof is directly subjected to oligomerization, times of action in the range from about 5 to 30 hours and, in particular, from about 10 to 20 hours are sufficient when the temperature of action is from about 20 to 50° C. and, in particular, from about 35 to 40° C. After incubation, insoluble components are advantageously removed by centrifugation. A few minutes at 10,000 g is expedient.

The detergent concentration to be chosen depends on the detergent used. If SDS is used, a concentration in the range from 0.01 to 1% by weight, preferably, from 0.05 to 0.5% by weight, for example, of about 0.2% by weight, proves expedient. If lauric acid or oleic acid is used, somewhat higher concentrations are expedient, for example, in a range from 0.05 to 2% by weight, preferably, from 0.1 to 0.5% by weight, for example, of about 0.5% by weight. The detergent action should take place at a salt concentration approximately in the physiological range. Thus, in particular NaCl concentrations in the range from 50 to 500 mM, preferably, from 100 to 200 mM and, more particularly, at about 140 mM are expedient.

The subsequent reduction of the detergent action and continuation of incubation relates to further oligomerization give the Aβ(X-Y) globulomer of the invention (in International Application Publication No. WO 04/067561 referred to as oligomer B). Since the composition obtained from the preceding step regularly contains detergent and a salt concentration in the physiological range, it is then expedient to reduce detergent action and, preferably, also salt concentration. This may be carried out by reducing the concentration of detergent and salt, for example, by diluting expediently with water or a buffer of lower salt concentration, for example, Tris-HCl, pH 7.3. Dilution factors in the range from about 2 to 10, advantageously, in the range from about 3 to 8 and, in particular, of about 4, have proved suitable. The reduction in detergent action may also be achieved by adding substances which can neutralize this detergent action. Examples of these include substances capable of complexing the detergents, like substances capable of stabilizing cells in the course of purification and extraction measures, for example, particular EO/PO block copolymers, in particular, the block copolymer under the trade name Pluronic® F 68. Alkoxylated and, in particular, ethoxylated alkyl phenols such as the ethoxylated t-octylphenols of the Triton® X series, in particular, Triton® X100, 3-(3-cholamidopropyldimethylammonio)-1-propanesulfonate (CHAPS®) or alkoxylated and, in particular, ethoxylated sorbitan fatty esters such as those of the Tween® series, in particular, Tween® 20, in concentration ranges around or above the particular critical micelle concentration, may be equally used.

Subsequently, the solution is incubated until sufficient Aβ(X-Y) globulomer has been produced. Times of action in the range of several hours, preferably, in the range from about 10 to 30 hours and, in particular, in the range from about 15 to 25 hours, are sufficient when the temperature of action is about 20 to 50° C. and, in particular, about 35 to 40° C. The solution may then be concentrated and possible residues may be removed by centrifugation. Again, a few minutes at 10,000 g proves expedient. The supernatant obtained after centrifugation contains an Aβ(X-Y) globulomer as described herein.

An Aβ(X-Y) globulomer can be finally recovered, e.g. by ultrafiltration, dialysis, precipitation or centrifugation. It is further preferred if electrophoretic separation of the Aβ(X-

Y) globulomers under denaturing conditions, e.g. by SDS-PAGE, produces a double band (e.g., with an apparent molecular weight of 38/48 kDa for Aβ(1-42)) and especially preferred if upon glutardialdehyde treatment of the oligomers, before separation, these two bands are merged into one. It is also preferred if size exclusion chromatography of the globulomers results in a single peak (e.g., corresponding to a molecular weight of approximately 60 kDa for Aβ(1-42)). Starting from Aβ(1-42) peptide, the process is, in particular, suitable for obtaining Aβ(1-42) globulomer Preferably, the globulomer shows affinity to neuronal cells and also exhibits neuromodulating effects. A "neuromodulating effect" is defined as a long-lasting inhibitory effect of a neuron leading to a dysfunction of the neuron with respect to neuronal plasticity.

According to another aspect of the invention, the term "Aβ(X-Y) globulomer" herein refers to a globulomer consisting essentially of Aβ(X-Y) subunits, wherein it is preferred if, on average, at least 11 of 12 subunits are of the Aβ(X-Y) type, more preferred, if less than 10% of the globulomers comprise any non-Aβ(X-Y) peptides and, most preferred, if the content of non-Aβ(X-Y) peptides in the preparation is below the detection threshold. More specifically, the term "Aβ(1-42) globulomer" herein refers to a globulomer comprising Aβ(1-42) units as defined above; the term "Aβ(12-42) globulomer" herein refers to a globulomer comprising Aβ(12-42) units as defined above; and the term "Aβ(20-42) globulomer" herein refers to a globulomer comprising Aβ(20-42) units as defined above.

The term "cross-linked Aβ(X-Y) globulomer" herein refers to a molecule obtainable from an Aβ(X-Y) globulomer as described above by cross-linking, preferably, chemically cross-linking, more preferably, aldehyde cross-linking and, most preferably, glutardialdehyde cross-linking of the constituent units of the globulomer. In another aspect of the invention, a cross-linked globulomer is essentially a globulomer in which the units are at least partially joined by covalent bonds, rather than being held together by non-covalent interactions only.

The term "Aβ(X-Y) globulomer derivative" herein refers, in particular, to a globulomer that is labelled by being covalently linked to a group that facilitates detection, preferably, a fluorophore, e.g., fluorescein isothiocyanate, phycoerythrin, *Aequorea victoria* fluorescent protein, Dictyosoma fluorescent protein or any combination or fluorescence-active derivatives thereof; a chromophore; a chemoluminophore, e.g., luciferase, preferably *Photinus pyralis* luciferase, *Vibrio fischeri* luciferase, or any combination or chemoluminescence-active derivatives thereof; an enzymatically active group, e.g., peroxidase such as horseradish peroxidase, or an enzymatically active derivative thereof; an electron-dense group, e.g., a heavy metal containing group such as a gold containing group; a hapten, e.g., a phenol derived hapten; a strongly antigenic structure, e.g., peptide sequence predicted to be antigenic such as by the algorithm of Kolaskar and Tongaonkar; an aptamer for another molecule; a chelating group, e.g., hexahistidinyl (SEQ ID NO. 23); a natural or nature-derived protein structure mediating further specific protein-protein interactions, e.g., a member of the fos/jun pair; a magnetic group, e.g., a ferromagnetic group; or a radioactive group such as a group comprising $^1H$, $^{14}C$, $^{32}P$, $^{35}S$ or $^{125}I$ or any combination thereof; or to a globulomer flagged by being covalently or by non-covalently linked by high-affinity interaction, preferably, covalently linked to a group that facilitates inactivation, sequestration, degradation and/or precipitation, preferably, flagged with a group that promotes in vivo degradation, more preferably, with ubiquitin, where it is particularly preferred if this flagged oligomer is assembled in vivo; or to a globulomer modified by any combination of the above. Such labelling and flagging groups and methods for attaching them to proteins are known in the art. Labelling and/or flagging may be performed before, during or after globulomerization. In another aspect of the invention, a globulomer derivative is a molecule obtainable from a globulomer by a labelling and/or flagging reaction. Correspondingly, the term "Aβ(X-Y) monomer derivative" herein refers, in particular, to an Aβ monomer that is labelled or flagged as described for the globulomer.

The term "greater affinity" herein refers to a degree of interaction where the equilibrium between unbound antibody and unbound globulomer, on the one hand, and antibody-globulomer complex, on the other, is further in favor of the antibody-globulomer complex. Likewise, the term "smaller affinity" herein refers to a degree of interaction where the equilibrium between unbound antibody and unbound globulomer, on the one hand, and antibody-globulomer complex, on the other, is further in favor of the unbound antibody and unbound globulomer.

The term "Aβ(X-Y) monomer" herein refers to the isolated form of the Aβ(X-Y) peptide, preferably, a form of the Aβ(X-Y) peptide which is not engaged in essentially non-covalent interactions with other Aβ peptides. Practically, the Aβ(X-Y) monomer is usually provided in the form of an aqueous solution. Preferably, the aqueous monomer solution contains 0.05% to 0.2%, more preferably, about 0.1% NaOH when used, for instance, for determining the binding affinity of the antibody of the present invention. In another preferable situation, the aqueous monomer solution contains 0.05% to 0.2%, more preferably, about 0.1% NaOH. When used, it may be expedient to dilute the solution in an appropriate manner. Further, it is usually expedient to use the solution within 2 hours, in particular, within 1 hour, and, especially, within 30 minutes after its preparation.

The term "fibril" herein refers to a molecular structure that comprises assemblies of non-covalently associated, individual Aβ(X-Y) peptides which show fibrillary structure under the electron microscope, which bind Congo red, exhibit birefringence under polarized light and whose X-ray diffraction pattern is a cross-β structure. The fibril may also be defined as a molecular structure obtainable by a process that comprises the self-induced polymeric aggregation of a suitable Aβ peptide in the absence of detergents, e.g., in 0.1 M HCl, leading to the formation of aggregates of more than 24, preferably, more than 100 units. This process is well known in the art. Expediently, Aβ(X-Y) fibril is used in the form of an aqueous solution. In a particularly preferred embodiment of the invention, the aqueous fibril solution is made by dissolving the Aβ peptide in 0.1% $NH_4OH$, diluting it 1:4 with 20 mM $NaH_2PO_4$, 140 mM NaCl, pH 7.4, followed by readjusting the pH to 7.4, incubating the solution at 37° C. for 20 h, followed by centrifugation at 10000 g for 10 min and resuspension in 20 mM $NaH_2PO_4$, 140 mM NaCl, pH 7.4.

The term "Aβ(X-Y) fibril" herein refers to a fibril comprising Aβ(X-Y) subunits where it is preferred if, on average, at least 90% of the subunits are of the Aβ(X-Y) type, more preferred, if at least 98% of the subunits are of the Aβ(X-Y) type and, most preferred, if the content of non-Aβ(X-Y) peptides is below the detection threshold.

Turning back to 8F5, as evidenced by FIG. 1, as well as 8C5 (FIG. 8), Aβ(1-42) globulomer-specific antibodies monoclonal antibodies 8F5 and 8C5 recognize predominantly Aβ(1-42) globulomer forms and not standard preparations of Aβ(1-40) or Aβ(1-42) monomers including aggregated Aβ(1-42) in contrast to nonspecific antibodies 6GI and 6E10. In particular, 8F5 detects Aβ(1-42) globulomers only by native PAGE-western blot and not by SDS-PAGE Western blot analysis indicating binding to a more complex detergent-dissociable intersubunit epitope in the core Aβ(1-42) globulomer structure. An intersubunit epitope is defined as a complex non-linear through space epitope located on at least two subunits. More specifically, dot-blot analysis against various Aβ(1-42) and Aβ(1-40) standard preparations showed significant differences in recognition of Aβ(1-42) globulomer versus non-globulomer Aβ forms (standard Aβ(1-40)/(1-42) monomer preparation, aggregated Aβ(1-42) for specific 8F5 and 8C5 but not for the isoform non-specific antibodies 6G1 and 6E10. The globulomer specificity of 8F5 and 8C5 but not of 6G1 and 6E10, was confirmed by quantifying Aβ(1-42) globulomer, Aβ(1-42) monomer, Aβ(1-40) monomer and soluble amyloid precursor protein alpha binding in sandwich ELISAs. Further, since these antibodies access the globulomer after native but not after SDS Western blotting, it is likely that each antibody recognizes a structural non-linear epitope in between subunits in the region of amino acids 20 to 30 of Aβ(1-42). Such specificity for globulomers is important because specifically targeting the globulomer form of Aβ with a globulomer preferential antibody such as, for example, 8F5 or 8C5 will: 1) avoid targeting insoluble amyloid deposits, binding to which may account for inflammatory side effects observed during immunizations with insoluble Aβ; 2) spare Aβ monomer and APP that are reported to have precognitive physiological functions (Plan et al., J. of Neuroscience 23:5531-5535 (2003); and 3) increase the bioavailability of the antibody, as it would not be shaded or inaccessible through extensive binding to insoluble deposits.

The subject invention also includes isolated nucleotide sequences (or fragments thereof) encoding the variable light and heavy chains of monoclonal antibody 8F5 and 8CD as well as those nucleotide sequences (or fragment thereof) having sequences comprising, corresponding to, identical to, hybridizable to, or complementary to at least about 70% (e.g., 70% 71%, 72%, 73%, 74%, 75%, 76%, 77%, 78% or 79%), preferably at least about 80% (e.g., 80%, 81%, 82%, 83%, 84%, 85%, 86%, 87%, 88% or 89%), and more preferably at least about 90% (e.g, 91%, 92%, 93%, 94%, 95%, 96%, 97%, 98% or 99%) identity to these encoding nucleotide sequences. (All integers (and portions thereof) between and including 70% and 100% are considered to be within the scope of the present invention with respect to percent identity.) Such sequences may be derived from any source (e.g., either isolated from a natural source, produced via a semi-synthetic route, or synthesized de novo). In particular, such sequences may be isolated or derived from sources other than described in the examples (e.g., bacteria, fungus, algae, mouse or human).

In addition to the nucleotide sequences described above, the present invention also includes amino acid sequences of the variable light and heavy chains of monoclonal antibody 8F5 and monoclonal antibody 8C5 (or fragments of these amino acid sequences). Further, the present invention also includes amino acid sequences (or fragments thereof) comprising, corresponding to, identical to, or complementary to at least about 70%, preferably at least about 80%, and more preferably at least about 90% identity to the amino acid sequences of the proteins of the present invention. (Again, all integers (and portions thereof) between and including 70% and 100% (as recited in connection with the nucleotide sequence identities noted above) are also considered to be within the scope of the present invention with respect to percent identity.)

For purposes of the present invention, a "fragment" of a nucleotide sequence is defined as a contiguous sequence of approximately at least 6, preferably at least about 8, more preferably at least about 10 nucleotides, and even more preferably at least about 15 nucleotides corresponding to a region of the specified nucleotide sequence.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup (Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

For purposes of the present invention, "complementarity" is defined as the degree of relatedness between two DNA segments. It is determined by measuring the ability of the sense strand of one DNA segment to hybridize with the anti-sense strand of the other DNA segment, under appropriate conditions, to form a double helix. A "complement" is defined as a sequence which pairs to a given sequence based upon the canonic base-pairing rules. For example, a sequence A-G-T in one nucleotide strand is "complementary" to T-C-A in the other strand.

In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity between two amino acid sequences is defined as the presence of a series of exactly alike or invariant amino acid residues in both sequences.) The definitions of "complementarity", "identity" and "similarity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

Additionally, a nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization.

The term "hybridization" as used herein is generally used to mean hybridization of nucleic acids at appropriate conditions of stringency as would be readily evident to those skilled in the art depending upon the nature of the probe sequence and target sequences. Conditions of hybridization and washing are well known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold spring harbor Press, Cold Spring harbor, N.Y., 1989, as noted above and incorporated herein by reference. (See also Short Protocols in Molecular Biology, ed. Ausubel et al. and Tijssen, Techniques in Biochemistry and Molecular Biology-Hybridization with Nucleic Acid Probes, "Overview of principles of hybridization and the strategy of nucleic acid assays" (1993), both incorporated herein by reference.) Specifically, the choice of conditions is dictated by the length of the sequences being hybridized, in particular, the length of the probe sequence, the relative G-C content of the nucleic acids and the amount of mismatches to be permitted. Low stringency conditions are preferred when partial hybridization between strands that have lesser degrees of complementarity is desired. When perfect or near perfect complementarity is desired, high stringency conditions are preferred. For typical high stringency conditions, the hybridization solution contains 6×S.S.C., 0.01 M EDTA, 1×Denhardt's solution and 0.5% SDS. Hybridization is carried out at about 68 degrees Celsius for about 3 to 4 hours for fragments of cloned DNA and for about 12 to about 16 hours for total eukaryotic DNA. For moderate stringencies, one may utilize filter pre-hybridizing and hybridizing with a solution of 3×sodium chloride, sodium citrate (SSC), 50% formamide (0.1 M of this buffer at pH 7.5) and 5×Denhardt's solution. One may then pre-hybridize at 37 degrees Celsius for 4 hours, followed by hybridization at 37 degrees Celsius with an amount of labeled probe equal to 3,000,000 cpm total for 16 hours, followed by a wash in 2×SSC and 0.1% SDS solution, a wash of 4 times for 1 minute each at room temperature and 4 times at 60 degrees Celsius for 30 minutes each. Subsequent to drying, one exposes to film. For lower stringencies, the temperature of hybridization is reduced to about 12 degrees Celsius below the melting temperature ($T_m$) of the duplex. The $T_m$ is known to be a function of the G-C content and duplex length as well as the ionic strength of the solution.

"Hybridization" requires that two nucleic acids contain complementary sequences. However, depending on the stringency of the hybridization, mismatches between bases may occur. As noted above, the appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

As used herein, an "isolated nucleic acid fragment or sequence" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A "fragment" of a specified polynucleotide refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferable at least about 25 nucleotides identical or complementary to a region of the specified nucleotide sequence.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "fragment or subfragment that is functionally equivalent" and "functionally equivalent fragment or subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense by linking a nucleic acid fragment or subfragment thereof, whether or not it encodes an active enzyme, in the appropriate orientation, relative to a plant promoter sequence.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

"Gene" refers to a nucleic acid fragment that expresses a specific protein, including regulatory sequences preceding (5' non-coding sequences) and following (3' non-coding sequences) the coding sequence.

"Native gene" refers to a gene as found in nature with its own regulatory sequences. In contrast, "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

A "foreign" gene refers to a gene not normally found in the host organism, but that is introduced into the host organism by gene transfer. Foreign genes can comprise native genes inserted into a non-native organism, or chimeric constructs. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" or "regulatory gene sequence" refers to a DNA sequence capable of controlling the expression of a coding sequence or functional RNA. The sequence consists of proximal and more distal upstream elements, the latter elements often referred to as enhancers. Accordingly, an "enhancer" is a DNA sequence which can stimulate promoter or regulatory gene sequence activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most host cell types at most times are commonly referred to as "constitutive promoters". New promoters of various types useful in plant cells are constantly being discovered; numerous examples may be found in the compilation by Okamuro and Goldberg, *Biochemistry of Plants* 15:1-82 (1989). It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the gene sequence that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or pro-peptides present in the primary translation product have been removed. "Precursor" protein refers to the primary product of translation of mRNA; i.e., with pre- and pro-peptides still present. Pre- and pro-peptides may be but are not limited to intracellular localization signals.

"Stable transformation" refers to the transfer of a nucleic acid fragment into a genome of a host organism, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T., *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al., *Cold Spring Harbor Symp. Quant. Biol.* 51:263-273 (1986); Erlich et al., European Patent Application No. 50,424; European Patent Application No. 84,796; European Patent Application No. 258,017; European Patent Application No. 237,362; Mullis, European Patent Application No. 201,184; Mullis et al., U.S. Pat. No. 4,683,202; Erlich, U.S. Pat. No. 4,582,788; and Saiki et al., U.S. Pat. No. 4,683,194). The process utilizes sets of specific in vitro synthesized oligonucleotides to prime DNA synthesis. The design of the primers is dependent upon the sequences of DNA that are to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform host plants as is well known to those skilled in the art. For example, a plasmid can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

A "monoclonal antibody" as used herein is intended to refer to one of a preparation of antibody molecules containing antibodies which share a common heavy chain and common light chain amino acid sequence, in contrast with an antibody from a "polyclonal" antibody preparation which contains a mixture of different antibodies. Monoclonal antibodies can be generated by several novel technologies like phage, bacteria, yeast or ribosomal display, as well as classical methods exemplified by hybridoma-derived antibodies (e.g., an antibody secreted by a hybridoma prepared by hybridoma technology, such as the standard Kohler and Milstein hybridoma methodology ((1975) *Nature* 256:495-497). Thus, a non-hybridoma-derived agonistic antibody of the invention is still referred to as a monoclonal antibody although it may have been derived by non-classical methodologies.

An "isolated antibody", as used herein, is intended to refer to an antibody that is substantially free of other antibodies having different antigenic specificities (e.g., an isolated antibody that specifically binds to a globulomer is substantially free of antibodies that specifically bind antigens other than a globulomer). An isolated antibody that specifically binds a globulomer may, however, have cross-reactivity to other antigens. Moreover, an isolated antibody may be substantially free of other cellular material and/or chemicals.

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Such antibody embodiments may also be bispecific, dual specific, or multispecific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1969) *Nature* 341:544-546), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. j., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. (See also Kabat et al. Sequences of Proteins of Immunological Interest, Fifth Edition, U.S. Department of Health and Human Services, NIH Publication No. 91-3242, 1991). The human antibodies of the present invention, however, may include amino acid residues not encoded by human germline immunoglobulin sequences (e.g., mutations introduced by random or site-specific mutagenesis in vitro or by somatic mutation in vivo). (See also Harlow and Lane, Antibodies: A Laboratory Manual, New York: Cold Spring Harbor Press, 1990).

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of $V_H$ and/or VL are replaced with CDR sequences of another species, such as antibodies having murine heavy and light chain variable regions in which one or more of the murine CDRs (e.g., CDR3) has been replaced with human CDR sequences.

Recombinant human antibodies of the present invention have variable regions, and may also include constant regions, derived from human germline immunoglobulin sequences. (See Kabat et al. (1991) supra.) In certain embodiments, however, such recombinant human antibodies are subjected to in vitro mutagenesis (or, when an animal transgenic for human Ig sequences is used, in vivo somatic mutagenesis), and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis or backmutation or both.

The term "backmutation" refers to a process in which some or all of the somatically mutated amino acids of a human antibody are replaced with the corresponding germline residues from a homologous germline antibody sequence. The heavy and light chain sequences of a human antibody of the invention are aligned separately with the germline sequences in the VBASE database to identify the sequences with the highest homology. VBASE is a comprehensive directory of all human germline variable region sequences compiled from published sequences, including current releases of GenBank and EMBL data libraries. The database has been developed at the MRC Centre for Protein Engineering (Cambridge, UK) as a depository of the sequenced human antibody genes (website: http://www.mrc-cpe.cam.ac.uk/vbase-intro.php?menu=901). Differences in the human antibody of the invention are returned to the germline sequence by mutating defined nucleotide positions encoding such different amino acids. The role of each amino acid thus identified as a candidate for backmutation should be investigated for a direct or indirect role in antigen binding, and any amino acid found after mutation to affect any desirable characteristic of the human antibody should not be included in the final human antibody. To minimize the number of amino acids subject to backmutation, those amino acid positions found to be different from the closest germline sequence, but identical to the corresponding amino acid in a second germline sequence, can remain, provided that the second germline sequence is identical and co-linear to the sequence of the human antibody of the invention for at least 10, preferably 12, amino acids on both sides of the amino acid in question. Backmutation may occur at any stage of antibody optimization.

A "labeled binding protein" is a protein wherein an antibody or antibody portion of the invention is derivatized or linked to another functional molecule (e.g., another peptide or protein). For example, a labeled binding protein of the invention can be derived by functionally linking an antibody or antibody portion of the invention (by chemical coupling, genetic fusion, noncovalent association or otherwise) to one or more other molecular entities, such as another antibody (e.g., a bispecific antibody or a diabody), detectable agent, a cytotoxic agent, a pharmaceutical agent, and/or a protein or peptide that can mediate associate of the antibody or antibody portion with another molecule (such as a streptavidin core region or a polyhistidine tag).

For purposes of the present invention, a "glycosylated binding protein" comprises a protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R, Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., Mol. Immunol. (1993) 30:1361-1367), or result in increased affinity for the antigen (Wallick, S. C., et al., Exp. Med. (1988) 168:1099-1109; Wright, A., et al., EMBO J. (1991) 10:2717 2723). Further, glycosylation site mutants can be made in which the O- or N-linked glycosylation site of the binding protein has been mutated. One skilled in the art can generate such mutants using standard well-known technologies. Glycosylation site mutants that retain the biological activity but have increased or decreased binding activity are also contemplated.

Further, the glycosylation of the antibody or antigen-binding portion of the invention can modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such a glycosylation may increase the affinity of the antibody for antigen. Such an approach is described in further detail in International Application Publication No. WO 03/016466A2, and U.S. Pat. Nos. 5,714,350 and 6,350,861, each of which is incorporated herein by reference in its entirety.

Additionally or alternatively, a modified antibody can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. (See, for example, Shields, R. L. et al. (2002) J. Biol. Chem. 277:26733-26740; Umana et al. (1999) Nat. Biotech. 17:176-1, as well as, European Patent No: EP 1,176,195; International Application Publication Number WO 03/035835 and WO 99/5434280, each of which is incorporated herein by reference in its entirety.)

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in amammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that host of a cell may be achieved by genetically modifying the host cell to express heterologous glycosylation enzymes. Using techniques known in the art a practitioner may genera antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. Patent Application Publication Nos. 20040018590 and 20020137134 and International Application Publication No. WO 05/100584 A2).

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

The invention also provides a method for making the monoclonal antibodies of the invention from non-human, non-mouse animals by immunizing non-human transgenic animals that comprise human immunoglobulin loci. One may produce such animals using methods known in the art. In a preferred embodiment, the non-human animals may be rats, sheep, pigs, goats, cattle or horses. Antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using an antigen (for example, a globulomer) or a portion thereof, or a cell expressing the antigen of interest. In a preferred embodiment, the initial screening is performed using an enzyme-linked immunoassay (ELISA) or a radioimmunoassay (RIA), preferably an ELISA. An example of ELISA screening is provided in International Application Publication No. WO 00/37504, herein incorporated by reference.

The antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art. Preferably, the immunized animal is a non-human animal that expresses human immunoglobulin genes and the splenic B cells are fused to a myeloma derived from the same species as the non-human animal.

In one aspect, the invention provides hybridomas that produce monoclonal antibodies to be used in the treatment, diagnosis and prevention of Alzheimer's Disease. In a preferred embodiment, the hybridomas are mouse hybridomas. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an antibody against a globulomer.

Recombinant antibodies may be generated from single, isolated lymphocytes using a procedure referred to in the art as the selected lymphocyte antibody method (SLAM), as described in U.S. Pat. No. 5,627,052, International Application Publication No. WO 92/02551 and Babcock, J. S. et al. (1996) *Proc. Natl. Acad. Sci. USA* 93: 7843-7848. In this method, single cells secreting antibodies of interest (e.g., lymphocytes derived from the immunized animal) are screened using an antigen-specific hemolytic plaque assay, wherein the antigen (e.g., globulomer), or a fragment thereof, is coupled to sheep red blood cells using a linker, such as biotin, and used to identify single cells that secrete antibodies with specificity for the antigen. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to IL-18. The amplified immunoglobulin sequences further can be manipulated in vitro, such as by in vitro affinity maturation methods such as those described in International Application Publication No. WO 97/29131 and International Application Publication. No. WO 00/56772.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a nonhuman species (e.g., a mouse) but in which at least a portion of the VH and/or VL sequence has been altered to be more "human-like", i.e., more similar to human germline variable sequences. One type of humanized antibody is a CDR-grafted antibody in which human CDR sequences are introduced into nonhuman VH and VL sequences to replace the corresponding nonhuman CDR sequences. In particular, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In other embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. Further, as used herein, the term "consensus immunoglobulin sequence" refers to the sequence formed from the most frequently occurring amino acids (or nucleotides) in a family of related immunoglobulin sequences (see e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

The term "activity" includes activities such as the binding specificity/affinity of an antibody for an antigen.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphory, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{on}$", as used herein, is intended to refer to the "on rate" constant for association of an antibody to the antigen to form the antibody/antigen, complex as is known in the art.

The term "$K_{off}$", as used herein, is intended to refer to the "off rate" constant for dissociation of an antibody from the antibody/antigen complex as is known in the art.

The term "$K_d$", used herein, is intended to refer to the "dissociation constant" of a particular antibody-antigen interaction as is known in the art.

The term "labeled binding protein" as used herein, refers to a protein with a label incorporated that provides for the identification of the binding protein. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3$H, $^{14}$C, $^{35}$S, $^{90}$Y, $^{99}$Tc, $^{111}$In, $^{125}$I, $^{131}$I, $^{177}$Lu, $^{166}$Ho or $^{153}$Sm); fluorescent labels (e.g., FITC, rhodamine or lanthanide phosphors), enzymatic labels (e.g., horseradish peroxidase, luciferase or alkaline phosphatase); chemiluminescent markers; biotinyl groups; predetermined polypeptide epitopes recognized by a secondary reporter (e.g., leucine zipper pair sequences, binding sites for secondary antibodies, metal binding domains or epitope tags) and magnetic agents, such as gadolinium chelates.

The term "antibody conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. Preferably, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, as well as analogs and homologs of these agents.

The terms "crystal", and "crystallized" as used herein, refer to an antibody, or antigen binding portion thereof, that exists in the form of a crystal. Crystals are one form of the solid state of matter.

The term "immunize" refers herein to the process of presenting an antigen to an immune repertoire whether that repertoire exists in a natural genetically unaltered organism, or a transgenic organism modified to display an artificial human immune repertoire. Similarly, an "immunogenic preparation" is a formulation of antigen that contains adjuvants or other additives that would enhance the immunogenicity of the antigen. An example of this would be co-injection of a purified form of GLP-1 receptor with Freund's complete adjuvant into a mouse. "Hyperimmunization", as defined herein, is the act of serial, multiple presentations of an antigen in an immunogenic preparation to a host animal with the intention of developing a strong immune response.

One way of measuring the binding kinetics of an antibody is by surface plasmon resonance. The term "surface plasmon resonance", as used herein, refers to an optical phenomenon that allows for the analysis of real-time biospecific interactions by detection of alterations in protein concentrations within a biosensor matrix, for example using the Biacore system (Biacore International, Upsala, Sweden and Piscataway, N.J.). For further descriptions, see Jönsson et al. (1993) Annales de Biologie Clinique (Paris) 51:19-26; Jönsson et al. (1991) Biotechniques 11:620-627; Johnnson et al. (1995) Journal of Molecular Recognition 8:125-131; and Johnnson et al. (1991) Analytical Biochemistry 198:268-277.

A "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The antibodies and antibody-portions of the invention can be incorporated into a pharmaceutical composition suitable for, for example, parenteral administration. Preferably, the antibody or antibody-portions will be prepared as an injectable solution containing 0.1-250 mg/ml antibody. The injectable solution can be composed of either a liquid or lyophilized dosage form in a flint, or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound. (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents that are useful for treating Alzheimer's Disease or related diseases or conditions. For example, one of the antibodies of the subject invention or antibody portion thereof may be coformulated and/or coadministered with one or more additional antibodies that bind other targets.

In certain embodiments, a monoclonal antibody of the subject invention or fragment thereof may be linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, New York (1997)).

Uses of the Monoclonal Antibody

The monoclonal antibodies of the present invention (e.g., 8F5 and 8CF) have many interesting utilities. For example, the monoclonal antibodies may be used in the prevention, treatment and diagnosis of Alzheimer's Disease as described above. Further, the antibodies may be used in the development of anti-antibodies. Further, the hybridoma producing the respective antibody allows for the steady production of a continuous source of identical monoclonal antibodies (i.e., reagents), thereby guaranteeing identity between antibodies in various experiments as well as therapeutic uses.

Also, the methods of the present invention allow one to prepare appropriate amounts of starting material for use in the preparation of further materials that, in turn, may be utilized in the production of monoclonal antibodies (or other antibodies) for the treatment of Alzheimer's Disease. As noted above, the antibodies may also be used for passive immunization in order to prevent Alzheimer's Disease or other related neurological conditions characterized by the same symptoms as Alzheimer's Disease such as cognitive impairment.

In one diagnostic embodiment of the present invention, an antibody of the present invention (e.g., 8F5), or a portion thereof, is coated on a solid phase (or is present in a liquid phase). The test or biological sample (e.g., whole blood, cerebrospinal fluid, serum, etc.) is then contacted with the solid phase. If antigen (e.g., globulomer) is present in the sample, such antigens bind to the antibodies on the solid phase and are then detected by either a direct or indirect method. The direct method comprises simply detecting presence of the complex itself and thus presence of the antigens. In the indirect method, a conjugate is added to the bound antigen. The conjugate comprises a second antibody, which binds to the bound antigen, attached to a signal-generating compound or label. Should the second antibody bind to the bound antigen, the signal-generating compound generates a measurable signal. Such signal then indicates presence of the antigen in the test sample.

Examples of solid phases used in diagnostic immunoassays, are porous and non-porous materials, latex particles, magnetic particles, microparticles (see e.g., U.S. Pat. No. 5,705,330), beads, membranes, microtiter wells and plastic tubes. The choice of solid phase material and method of labeling the antigen or antibody present in the conjugate, if desired, are determined based upon desired assay format performance characteristics.

As noted above, the conjugate (or indicator reagent) will comprise an antibody (or perhaps anti-antibody, depending upon the assay), attached to a signal-generating compound or label. This signal-generating compound or "label" is itself detectable or may be reacted with one or more additional compounds to generate a detectable product. Examples of signal-generating compounds include chromogens, radioisotopes (e.g., 125I, 131I, 32P, 3H, 35S and 14C), chemiluminescent compounds (e.g., acridinium), particles (visible or fluorescent), nucleic acids, complexing agents, or catalysts such as enzymes (e.g., alkaline phosphatase, acid phosphatase, horseradish peroxidase, beta-galactosidase and ribonuclease). In the case of enzyme use (e.g., alkaline phosphatase or horseradish peroxidase), addition of a chromo-, fluro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

Examples of biological fluids which may be tested by the above immunoassays include plasma, whole blood, dried whole blood, serum, cerebrospinal fluid or aqueous or organo-aqueous extracts of tissues and cells.

The present invention also encompasses a method for detecting the presence of antibodies in a test sample. This method comprises the steps of: (a) contacting the test sample suspected of containing antibodies with anti-antibody specific for the antibodies in the patient sample under time and conditions sufficient to allow the formation of anti-antibody/antibody complexes, wherein the anti-antibody is an antibody of the present invention which binds to an antibody in the patient sample; (b) adding a conjugate to the resulting anti-antibody/antibody complexes, the conjugate comprising an antigen (which binds to the anti-antibody) attached to a signal generating compound capable of detecting a detectable signal; and (d) detecting the presence of the antibodies which may be present in the test sample by detecting the signal generated by the signal generating compound. A control or calibrator may be used which comprises antibody to the anti-antibody.

The present invention also includes a vaccine comprising one of more of the antibodies described herein or a portion thereof and a pharmaceutically acceptable adjuvant (e.g., Freund's adjuvant or phosphate buffered saline).

Kits are also included within the scope of the present invention. More specifically, the present invention includes kits for determining the presence of antigens (e.g., globulomers) in a patient suspected of having Alzheimer's Disease or another condition characterized by cognitive impairment. In particular, a kit for determining the presence of antigens in a test sample comprises a) an antibody as defined herein or portion thereof; and b) a conjugate comprising a second antibody (having specificity for the antigen) attached to a signal generating compound capable of generating a detectable signal. The kit may also contain a control or calibrator which comprises a reagent which binds to the antigen as well as an instruction sheet detailing how the kit is to be utilized and the components of the kit.

The present invention also includes a kit for detecting antibodies in a test sample. The kit may comprise a) an anti-antibody specific (for example, one of the subject invention) for the antibody of interest, and b) an antigen or portion thereof as defined above. A control or calibrator comprising a reagent which binds to the antigen may also be included. More specifically, the kit may comprise a) an anti-antibody (such as the one of the present invention) specific for the antibody and b) a conjugate comprising an antigen (e.g., globulomer) attached to a signal generating compound capable of generating a detectable signal. Again, the kit may also comprise a control of calibrator comprising a reagent which binds to the antigen and may also comprise an instruction sheet or package insert describing how the kit should be used and the components of the kit.

The kit may also comprise one container such as vial, bottles or strip, with each container with a pre-set solid phase, and other containers containing the respective conjugates. These kits may also contain vials or containers of other reagents needed for performing the assay, such as washing, processing and indicator reagents.

It should also be noted that the subject invention not only includes the full length antibodies described above but also portions or fragments thereof, for example, the Fab portion thereof. Additionally, the subject invention encompasses any antibody having the same properties of the present antibodies in terms of, for example, binding specificity, structure, etc.

Deposit Information:

The hybridoma (ML5-8F5.1F2.2A2) which produces monoclonal antibody 8F5 was deposited with the American Type Culture Collection, 10801 University Boulevard, Manassas, Va. 20110 on Dec. 1, 2005 under the terms of the Budapest Treaty and was assigned ATCC No. PTA-7238.

Hybridoma (ML5-8C5.2C1.8E6.2D5) which produces monoclonal antibody 8C5 was deposited with the American Type Culture Collection, 10801 University Boulevard, Manassas, Va. 20110 on Feb. 28, 2006 under the terms of the Budapest Treaty and was assigned ATCC No. PTA-7407.

The present invention may be illustrated by use of the following non-limiting examples:

Example I(a)

Production of Monoclonal Antibodies 8F5 and 8C5

Balb/c mice were immunized sub-q with 50 microgram of A-beta (1-42) globulomer as described in Barghorn et al., 2005, J Neurochem, 95, 834-847 in CFA (Sigma) and boosted twice at one month intervals. Spleens were collected and spleen cells fused with mouse myeloma SP2/0 cells at 5:1 ratio by a PEG procedure. Fusion cells were plated in 96-well dishes in Azaserine/Hypoxanthine selection media at $2 \times 10^5$ cells/ml, 200 ml per well. Cells were allowed to grow to form visible colonies and supernatants assayed for A-beta oligomer reactivity by a direct ELISA assay. Hybridomas secreting antibodies to A-beta oligomers were subcloned by limiting dilution, until antibody expression appeared stable.

Example II

8F5 and 8C5 Preferential Globulomer Binding Compared to Monomer Preparations of Aß(1-40) and Aß(1-42)

To test the selectivity of 8F5, two differently dissolved Aß(1-42) monomer preparations were used as well as freshly prepared Aß(1-40) as surrogates for monomers. Two types of experiments were performed. In a first experiment, 8F5 was tested for Aß globulomer selectivity by a Sandwich-ELISA with globulomer derived but conformer non-specific MAb 6G1 (see S. Barghorn et al. J. Neurochemistry, 95:834 (2005)) as a capture antibody. Biotinylated 8F5 was used as the second and conformer selective antibody. This experiment is described in Example 2.1 below.

In a second example, described in Example 2.2 below, the oligomer selectivity versus Aß(1-42) monomer and Aß(1-40) monomer was examined by dot blot immunoassay. In this experiment, 8F5 exhibited preferential binding to Aß(1-42) globulomer (compared to a known antibody 4G8 mapping to a similar region as 8F5, but derived from immunization with a linear peptide Aß(17-24) (Abcam Ltd., Cambridge, Mass.)), as compared to Aß(1-42) monomer as well as compared to Aß(1-40) monomer. 8C5 was tested in an identical protocol to 8F5.

Example 2.1: Oligomer Selectivity of Monoclonal Antibody 8F5 and 8C5 a) Preparation, of Aß(1-42) Globulomer:

9 mg Aß(1-42) Fa. Bachem were dissolved in 1.5 ml HFIP (1.1.1.3.3.3 Hexafluor-2-propanol) and incubated 1.5 h at 37° C. The solution was evaporated in a SpeedVac and suspended in 396 µl DMSO (5 mM Aß stock solution). The sample was sonified for 20 seconds in a sonic water bath, shaken for 10 minutes and stored over night at −20° C.

The sample was diluted with 4.5 ml PBS (20 mM NaH2PO4; 140 mM NaCl; pH 7, 4) and 0.5 ml 2% aqueous SDS-solution were added (0.2% SDS content). The mixture was incubated for 7 h at 37° C., diluted with 16 ml H$_2$O and further incubated for 16 hours at 37 deg C. After that, the Aß(1-42) globulomer solution was centrifuged for 20 min at 3000 g. The supernatant was concentrated to 0.5 ml by 30 KDa centriprep. The concentrate was dialysed against 5 mM NaH2PO4; 35 mM NaCl; pH7.4 overnight at 6° C. Subsequently, the Aß(1-42) globulomer concentrate was centrifuged for 10 min at 10000 g. The supernatant was than aliquoted and stored at −20° C.

b) Preparation of Monomer Aß(1-42), HFIP Pretreated:

3 mg human Aß(1-42), (Bachem Inc) cat. no. H-1368 were dissolved in 0.5 ml HFIP (6 mg/ml suspension) in an 1.7 ml Eppendorff tube and was shaken (Eppendorff Thermo mixer, 1400 rpm) for 1.5 h at 37° C. till a clear solution was obtained. The sample was dried in a speed vac concentrator (1.5 h) and resuspended in 13.2 µl DMSO, shook for 10 sec., followed by ultrasound bath sonification (20 sec) and shaking (e.g. in Eppendorff Thermo mixer, 1400 rpm) for 10 min.

6 ml 20 mM NaH2PO4; 140 mM NaCl; 0.1% Pluronic F68; pH 7.4 was added and stirred for 1 h at room temperature. The sample was centrifuged for 20 min at 3000 g. The supernatant was discarded and the precipitate solved in 0.6 ml 20 mM NaH2PO4; 140 mM NaCl; 1% Pluronic F68; pH 7.4. 3.4 ml water was added and stirred for 1 h at room temperature followed by 20 min centrifugation at 3000 g. 8×0.5 ml aliquots of the supernatant were stored at −20°.

c) Preparation of Monomer Aß(1-42) in NH$_4$OH:

1 mg Aß(1-42) solid powder (Bachem Inc. cat. no. H-1368) was dissolved in 0.5 ml 0.1% NH$_4$OH in water (freshly prepared) (2 mg/ml) and immediately shaken for 30 sec. at room temperature to get a clear solution. The sample was stored at −20° C. for further use.

d) Preparation of Monomer Aß(1-40):

1 mg human Aß(1-40), (Bachem Inc) cat. no. H-1194 was suspended in 0.25 ml HFIP (4 mg/ml suspension) in an Eppendorff tube. The tube was shaken (e.g., in an Eppendorff Thermo mixer, 1400 rpm) for 1.5 h at 37° C. to get a clear solution and afterwards dried in a speed vac concentrator (1.5 h). The sample was redissolved in 46 µl DMSO (21.7 mg/ml solution), shaken for 10 sec., followed by 20 sec. sonification in ultrasound bath. After 10 min of shaking (e.g. in Eppendorff Thermo mixer, 1400 rpm), the sample was stored at −20° C. for further use.

e) Biotinylation of Anti-Aß Mouse Mab 8F5:

500 µl anti-Aß mouse Mab 8F5 (0.64 mg/ml) in PBS were added to 2 µl 20 mq/ml Sulfo-NHS-Biotin (Pierce Inc. cat.no. 21420) freshly dissolved in water and shaken (e.g. in Eppendorff Thermo mixer, 1400 rpm), for 30 min, dialyzed 16 h at 6° C. in a dialysis tube against 500 ml 20 mM Na Pi; 140 mM NaCl; pH 7.4. The dialysate was stored at −20° C. for further use. 8C5 was biotinylated accordingly.

f) Sandwich-ELISA for Aß-Samples:

g) Reagent List:

1. F96 Cert. Maxisorp NUNC-Immuno Plate Cat. No.: 439454
2. Binding antibody:
   Anti-Aß mouse MAb 6G1, solved in PBS; conc.: 0.4 mq/ml; store at −20° C.
3. Coating-Buffer:
   100 mM Sodiumhydrogencarbonate; pH 9.6
4. Blocking Reagent for ELISA; Roche Diagnostics GmbH Cat. No.: 1112589
5. PBST-Buffer:
   20 mM $NaH_2PO_4$; 140 mM NaCl; 0.05% Tween 20; pH 7.4
6. Albumin bovine fraction V, protease-free; Serva Cat.No.: 11926.03; store at 4° C.
7. PBST+0.5% BSA-Buffer:
   20 mM $NaH_2PO_4$; 140 mM NaCl; 0.05% Tween 20; pH 7.4+0.5% BSA
8. Aß(1-42)-globulomer Standard Stock:
   solution in 5 mM $NaH_2PO_4$; 35 mM NaCl; pH7.4; conc.: 10.77 mg/ml; store at −20° C.
9. Aß(1-42) monomer HFIP treated Standard Stock:
   solution in 3 mM $NaH_2PO_4$; 21 mM NaCl; 0.15% Pluronic F68; pH 7.4; conc.: 0.45 mg/ml; store at −20° C.
10. Aß(1-42) monomer in NH4OH Standard Stock; solution in 0.1% $NH_4OH$ conc.: 2 mg/ml; store at −20° C.
11. Aß(1-40) monomer HFIP treated Standard Stock; solution in DMSO; conc.: 21.7 mg ml; store at −20° C.
12. biotinyliated anti-Aß mouse mAb clone 8F5; solution in PBS; conc.: 0.24 mg/ml; store at −80° C.
13. Streptavidin-POD conjugate; Fa.Roche Cat. No.: 1089153
14. staining:
    TMB; Roche Diagnostics GmbH Cat.No.: 92817060; 42 mM in DMSO; 3% $H_2O_2$ in water; 100 mM sodium acetate pH 4.9
15. Stop staining by adding 2M Sulfonic Acid solution Preparation of Reagents:

The following protocol was utilized:

1. Binding antibody
   Thaw mMAb 6G1 stock solution and dilute 1:400 in coating buffer.
2. Blocking reagent:
   Dissolve blocking reagent in 100 ml water to prepare the blocking stock solution and store aliquots of 10 ml at −20° C. Dilute 3 ml blocking stock solution with 27 ml water for each plate to block.
3. Aß Standard solutions:
   a) Aß(1-42)-globalomer
      Add 1 µl Aß (1-42)-globulomer standard stock solution to 1076 µl PBST+0.5% BSA=10 µg/ml
      Add 50 µl 10 µg/ml Aß(1-42)-globulomer standard solution to 4950 µl PBST+0.5% BSA=100 ng/ml
   b) Aß (1-42) monomer HFIP-treated
      Add 10 µl Aß(1-42) monomer HFIP-pretreated standard stock solution to 440 µl PBST+0.5% BSA=10 µg/ml
      Add 50 µg/ml 10 µg/ml Aß(1-42) monomer HFIP pretreated standard solution to 4950 µl PBST+0.5% BSA=100 ng/ml
   c) Aß (1-42) monomer in NH4OH
      Add 50 Aβ(1-42) monomer in NH4OH standard stock solution to 995 µl PBST+0.5% BSA=10 µg/ml
      Add 50 µl 10 µg/ml Aß(1-42) monomer in NH4OH standard solution to 4950 µl PBST+0.5% BSA=100 ng/ml
   d) Aß(1-40) monomer HFIP-pretreated
      Add 10 Aß(1-40) monomer HFIP pretreated standard stock solution to 49 µl PBST+0.5% BSA=430 µg/ml
      Add 10 µl 430 µg/ml Aß(1-40) monomer HFIP pretreated standard solution to 420 µl PBST+0.5% BSA=10 µg/ml
      Add 50 µl 10 µg/ml Aß(1-40) monomer HFIP pretreated standard solution to 4950 µl PBST+0.5% BSA=100 ng/ml Standard Curves:

| No Final Conc. | Stock. | | PBST + 0.5% BSA |
|---|---|---|---|
| 1 100 ng/ml | 2 ml S | | 0 ml |
| 2 31.6 ng/ml | 0.633 ml | (1) | 1.367 ml |
| 3 10 ng/ml | 0.633 ml | (2) | 1.367 ml |
| 4 3.16 ng/ml | 0.633 ml | (3) | 1.367 ml |
| 5 1 ng/ml | 0.633 ml | (4) | 1.367 ml |
| 6 0.32 ng/ml | 0.633 ml | (5) | 1.367 ml |
| 7 0.1 ng/ml | 0.633 ml | (6) | 1.367 ml |
| 8 0.0 ng/ml | 0 ml | | 2 ml |

1. Primary antibody: biotinylated mMAb 8F5:
   The concentrated biotinylated anti-Aß mAb 8F5 was diluted in PBST+0.5% BSA-buffer. The dilution factor was 1/1200=0.2 µg/ml. The antibody was used immediately.
2. Label Reagent:
   Reconstitute Streptavidin-POD conjugate lyophilizate in 0.5 ml water. Add 500 µl glycerol and store aliquots of 100 µl at −20° C. for further use.
   Dilute the concentrated label reagent in PBST-Buffer. The dilution factor is 1/10000. Use immediately.
3. Staining Solution TMB:
   Mix 20 ml 100 mM sodium acetate pH 4.9 with 200 µl of the TMB solution and 29.5 µl 3% peroxide solution. Use immediately.

Sample Plate Setup: (Note that all standards are run in duplicate)

|   | 1 | 2 | 3 | 4 | 5 | 6 | 7 | 8 | 9 | 10 | 11 | 12 |
|---|---|---|---|---|---|---|---|---|---|----|----|----|
| A | 100 | 100 | 100 | 100 | 100 | 100 | 100 | 100 | 100 | 100 | 100 | 100 |
| B | 31.6 | 31.6 | 31.6 | 31.6 | 31.6 | 31.6 | 31.6 | 31.6 | 31.6 | 31.6 | 31.6 | 31.6 |
| C | 10 | 10 | 10 | 10 | 10 | 10 | 10 | 10 | 10 | 10 | 10 | 10 |
| D | 3.16 | 3.16 | 3.16 | 3.16 | 3.16 | 3.16 | 3.16 | 3.16 | 3.16 | 3.16 | 3.16 | 3.16 |
| E | 1 | 1 | 1 | 1 | 1 | 1 | 1 | 1 | 1 | 1 | 1 | 1 |
| F | 0.32 | 0.32 | 0.32 | 0.32 | 0.32 | 0.32 | 0.32 | 0.32 | 0.32 | 0.32 | 0.32 | 0.32 |
| G | 0.1 | 0.1 | 0.1 | 0.1 | 0.1 | 0.1 | 0.1 | 0.1 | 0.1 | 0.1 | 0.1 | 0.1 |
| H | 0.0 | 0.0 | 0.0 | 0.0 | 0.0 | 0.0 | 0.0 | 0.0 | 0.0 | 0.0 | 0.0 | 0.0 |

Procedure Utilized:
1. Apply 1000 anti-Aß mMAb 6G1 solution per well and incubate overnight at 4° C.
2. Discard the antibody solution and wash the wells with 250 µl PBST-Buffer three times.
3. Add 260 µl block solution per well and incubate 2 h at room temperature.
4. Discard the block solution and wash the wells with 250 µl PBST-Buffer three times.
5. After preparation of standards, apply 100 µl per well of standards to the plate. Incubate 2 h at room temperature and overnight at 4° C.
6. Discard the standard solution and wash the wells with 250 µl PBST-Buffer three times.
7. Add 200 µl primary biotinylated antibody 8F5 solution per well and incubate 1.5 h at room temperature.
8. Discard the antibody solution and wash the wells with 2500 PBST-Buffer three times.
9. Add 200 µl label solution per well and incubate 1 h at room temperature,
10. Discard the label solution and wash the wells with 250 µl PBST-Buffer three times.
11. Add 100 µl of TMB solution to each well and incubate at room temperature (5-15 min).
12. Observe staining and apply 50 µl of the Stop Solution per well after beginning of background staining.
13. UV-read at 450 nm.
14. Calculate results from standard curve.
15. Evaluation The results are shown in FIG. 1 for the antibody 8F5 and in FIG. 8 for the antibody 8C5. Log EC50 values are significantly lowest for the Aß(1-42) globulomer antigen (1.958) compared to reduced values for two differently prepared Aß(1-42) monomers (2.745 and 3.003 respectively) and Aß(1-40) monomer (2.825). These data indicate about 10 fold selectivity of antibody 8F5 for Aß(1-42) globulomer versus Aß(1-42) monomer.

Almost identical results were obtained with antibody 8C5 and are shown in FIG. 8.

Example 2.2: Oligomer Selectivity of Monoclonal Antibody 8F5 and 8C5

Discrimination of Aβ monomer against Aβ globulomer by dot blot method: Comparison of 8F5 and 8C5 versus 4 GB.

Serial dilutions of Aβ(1-42) globulomer, Aβ1-42 monomer and Aβ1-40 monomer were made in the range from 100 pmol/µl-0.01 pmol/µl in PBS. Of each sample, 1 µl was dotted onto a nitrocellulose membrane. The mouse monoclonal antibodies 4G8 and 8F5 (0.2 µg/ml) were used for detection with an anti-mouse IgG coupled to alkaline phosphatase as secondary antibody and the staining reagent NBT/BCIP (Roche Diagnostics, Mannheim). The detection signal was analyzed in its intensity (reflective density=RD) via a densitometer (GS 800, Biorad, Hercules, Calif., USA) at an antigen concentration of 10 pmol. At this concentration for every Aβ-form, the measured reflective density was in the linear range of the densitometer detection. The other antibody 8C5 was used in an analogous protocol. The results are shown in Table 1 below:

|  | Reflective Density (RD) [10 pmol] | | | Ratio RD Aβ(1-42) globulomer/ | Ratio RD Aβ(1-42) globulomer/ |
|---|---|---|---|---|---|
|  | Aβ(1-42) globulomer | Aβ(1-42) monomer | Aβ(1-40) monomer | RD Aβ(1-42) monomer | RD Aβ(1-40) monomer |
| 8F5 | 1.6 | 1.1 | 0.1 | 1.4 | 16.9 |
| 8C5 | 1.3 | 0.2 | 0.3 | 5.1 | 4.1 |
| 4G8 | 3 | 3.1 | 0.7 | 1 | 4.2 |

Table 1: Discrimination of anti-Aβ-antibodies of Aβ1-40 monomer and Aβ1-42 monomer. The discrimination was calculated as the ratio of detection signal of Aβ1-42 globulomer and Aβ1-42 monomer, respectively Aβ1-40 monomer.

In particular, the above results indicate that 8F5 and 8C5 show a different binding profile compared to commercially available anti-Aβ(1-42) antibody to 4G8, which maps to Aβ (17-24) (i.e., a linear sequence). More specifically, 8F5 and 8C5 show a preference for globulomer binding versus Aβ42 monomer (see column 4; compare 1.4 versus 1) as well as a preference for globulomer binding versus Aβ40 (column 5; compare 16.9 versus 4.2). These two improved binding selectivities over standard 4 GB should result in the production of fewer side effects upon use of 8F5 and/or 8C5, as described above (e.g., plaque binding).

Example III

Binding of 8F5 and 8C5 to Aß(1-42) Fibrils

Since 8F5 antibody was generated against soluble globulomers, it was hypothesized that 8F5 should not bind to deposited plaque or fibril material. Therefore, binding of 8F5 to polymerized Aß fibril suspensions was tested as described in the following example:

Preparation of Aß(1-42) Fibrils:

1 mg Aß(1-42) (Bachem Inc., Catalog Nr.: H-1368) was dissolved in 500 µl aqueous 0.1% $NH_4OH$ (Eppendorff tube), and the sample was stirred for 1 min at room temperature followed by 5 min centrifugation at 10000 g. Supernatant was pipetted into a new Eppendorff tube Aß(1-42) concentration measured according to Bradford protein concentration assay (BIO-RAD Inc. assay procedure).

100 µl of this freshly prepared Aß(1-42) solution were neutralized with 300 µl 20 mM $NaH_2PO_4$; 140 mM NaCl;

pH 7.4 followed by 2% HCl to adjust pH 7.4. The sample was incubated for another 20 hrs at 37° C. and centrifuged (10 min, 10000 g). The supernatant was discarded and the fibril pellet resuspended with 400 µl 20 mM NaH2PO4; 140 mM NaCl; pH 7.4 under 1 min stirring on a Vortex mixer followed by centrifugation (10 min, 10000 g). After discarding the supernatant, this resuspending procedure was repeated, and the final fibril suspension spun down by another centrifugation (10 min, 10000 g). The supernatant was once again discarded and the final pellet resuspended in 380 µl 20 mM NaH2PO4; 140 mM NaCl; pH7.4 under 1 min stirring on a Vortex mixer. Aliquots of the sample were stored at −20° C. in a freezer.

80 µl fibril suspension were mixed with 320 µl 20 mM NaH2PO4; 140 mM NaCl; 0.05% Tween 20; pH 7.4, buffer and stirred for 5 min at room temperature followed by sonification (20 sec). After centrifugation (10 min, 10000 g), the pellet was resuspended with 190 µl 20 mM NaH2PO4; 140 mM NaCl; 0.05% Tween 20; pH 7.4 under stirring in a Vortex mixer.

Binding of Antibodies to Aß(1-42) Fibrils

10 µl aliquots of this fibril suspension was incubated with:
a) 10 µl 20 mM Na Pi; 140 mM NaCl; pH 7.4
b) 10 0.1 µg/µl mMAb 6E10 Signet Inc. Cat.#9320 in 20 mM
c) NaH2PO4; 140 mM NaCl; pH 7.4
d) 10 µl 0.1 µg/µl mMAb 4G8 SignetInc. Cat#9220 in 20 mM Na Pi; 140 mM NaCl; pH 7.4
e) 10 µl 0.1 µg/µl mMAb 8F5 (8C5) in 20 mM Na Pi; 140 mM NaCl; pH 7.4

Samples were incubated for 20 h at 37° C. Finally the samples were centrifuged (10 min at 10000 g). The supernatants containing the unbound antibody fraction were collected and mixed with 20 µl SDS-PAGE sample buffer. The pellet fractions were washed with 50 µl 20 mM NaH2PO4; 140 mM NaCl; pH 7.4 buffer under 1 min stirring in a Vortex mixer followed by centrifugation (10 min, 10000 g). The final pellets were resuspended in 20 µl 20 mM Na Pi; 140 mM NaCl; 0.025% Tween 20; pH 7.4 buffer and solved in 20 µl SDS-PAGE buffer.

SDS-PAGE Analysis

Supernatants and resuspended pellet samples were heated for 5 min at 98° C. and loaded onto a 4-20% Tris/Glycin Gel under the following conditions:

SDS-sample buffer: 0.3 g SDS; 0.77 g DTT; 4 ml 1M Tris/HCl pH 6.8; 8 ml glycerol; 1 ml 1% Bromphenolblue in Ethanol; add water to 50 ml 4-20% Tris/Glycin Gel: Invitrogen Inc., No.: EC6025BOX running buffer: 7.5 g Tris.; 36 g Glycine; 2.5 g SDS; add water to 2.5l The PAGE was run at 20 mA. Gels were stained by Coomassie Blue R250.

Figure 2:
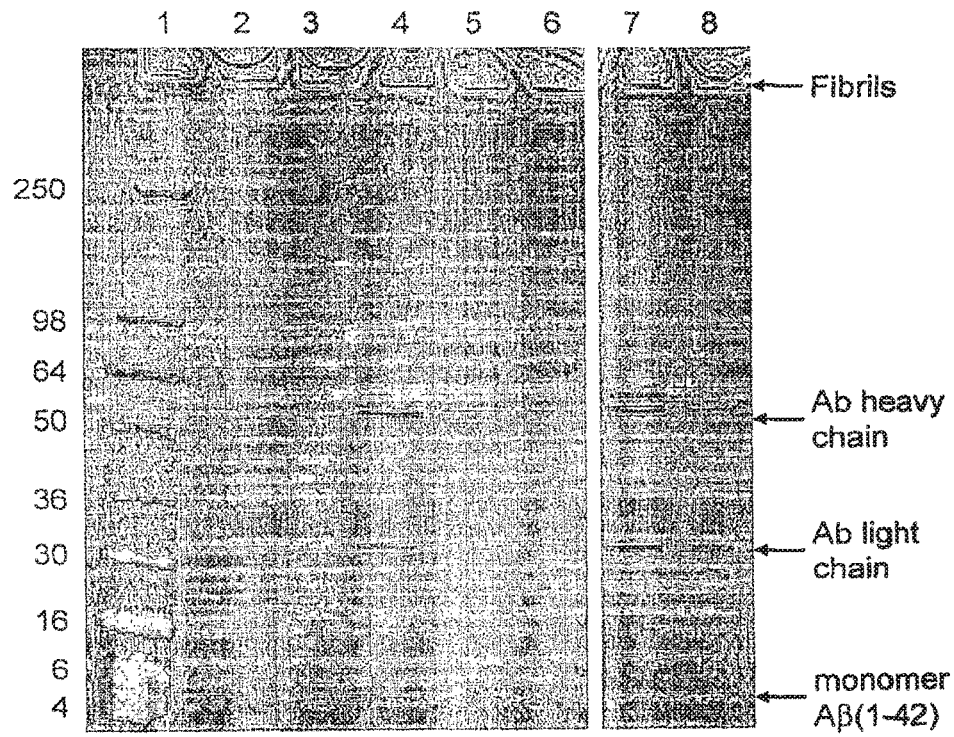
FIG. 2 illustrates SDS-PAGE analysis of fibril bound heavy and light chain antibodies (lanes 4, 6, 8) and corresponding non-bound free fractions (lanes 3, 5, 7) in the supernatants.

Results:

Coomassie staining of SDS-PAGE indicated the presence of heavy and light chains of antibodies predominantly in the supernatant of the fibril suspension (lane 7, FIG. 2), the remaining fibril suspension showed very little antibody material while also showing partly depolymerized Abeta at 4.5 kDa. In contrast to 8F5 and 8C5, other anti-Aßantibodies did not show up in the soluble fraction (6E10, lane 3, FIG. 2) or only partly (4G8, lane 5, FIG. 2) compared to fibril bound fraction (lane 6, FIG. 2).

The relative binding to fibril type Abeta was evaluated from SDS-PAGE analysis by measuring the Reflective Density values from the heavy chain of the antibodies in the fibril bound and the supernatant fractions and calculated according to the following formula:

Fibril bound $Ab$ fraction=$RD_{fibril\ faction} \times 100\%/(RD_{fibril\ faction}+RD_{supernatant\ fraction})$.

The following values were obtained:

| antibody | Fibril bound Ab fraction |
|---|---|
| 6E10 | 98% |
| 8F5 | 16% |
| 8C5 | 21% |

These data indicate a significant reduction of bound 8F5 and 8C5 compared to standard antibody 6E10.

Example IV

Preferential Binding of Endogenous Aß(1-42) Globulomers Compared to Aß(1-40)

Based upon the oligomer concept of Aß, it is important that anti-Aß oligomer antibodies also can demonstrate preferential binding for Aß (1-42) oligomers in vivo, in particular, over Aß(1-40) in Mild Cognitive Impairment and AD patients. The concept of lowering Aß(1-42) species over Aß(1-40) is used in a therapeutic approach for the treatment of AD via NSAIDs (Weggen et al., Nature 414, 212-216 (2001)). It is assumed that those NSAIDs which lower Aß(1-42) in relation to Aß(1-40) display the best efficacy in the treatment of Alzheimer Disease. The Aß(1-42)/Aß(1-40) ratio is important for a selective therapy as well as for diagnostic purposes.

An analysis was performed with CSF samples from Alzheimer's Disease patients and patients with MCI. From the results shown, in FIG. 3 and described below, it can be concluded that 8F5 has a major advantage over Aß antibodies like 6E10 because 8F5 detects a higher ratio of Aß(1-42) over less aggregating Aß(1-40). This advantage will allow one to more selectively diagnose and neutralize Aß(1-42) type oligomers in MCI and AD patients.

A) Endogenous Amyloid ß(1-42) and Amyloid ß(1-40) Levels in CSF of MCI and Ad Patients after Immunoprecipitation with Oligomer Selective Anti-Aß Murine MAB 8F5:

Immobilization of Anti-Aβ mMAB's to CNBr-Activated Sepharose 4B:
a) mMAb 6E10 Signet Inc., Cat.no. 9320
b) mMAb 8F5

0.4 g CNBr-activated Sepharose 4B (Amersham Pharmacia Bio-tech AB, Uppsala, Sweden, Inc., No.: 17-0430-01) were added to 10 ml aqueous 1 mM HCl and incubated for 30 min at room temperature. The CNBr-activated Sepharose 4B was washed three times with 10 ml 1 mM HCl and twice with 10 ml 100 mM NaHCO3; 500 mM NaCl; pH 8.3 For each of the immobilized antibodies, 100 µl CNBr-activated Sepharose 4B Matrix were added to 950 µl 0.5 mg/ml anti-Aß mMAb solution in 100 mM NaHCO3; 500 mM NaCl; pH 8.3. After 2 h of shaking at room temperature, samples were centrifuged for 5 min at 10000 g. Then, 500 µl 100 mM Ethanolamine; 100 mM NaHCO3; 500 mM NaCl; pH 8.3, buffer was added to the beads, and samples were shaken for 1 h at room temperature. The anti-Aß mMAb-Sepharose samples were centrifuged for 5 min at 10000 g and washed 5 times with 500 µl 20 mM NaH2PO4; 140 mM NaCl; pH 7.4. Before storage at 6° C., samples were stabilized by adding sodium azide to 0.02% final concentration.

Immunoprecipitation:
  a) mMAb 6E10-Sepharose
  b) mMAb 8F5-Sepharose
200 µl of the human Cerebral Spinal Fluid samples were diluted with 200 µl 20 mM $NaH_2PO_4NaH_2PO_4$; 140 mM NaCl; 0.05% Tween 20; pH 7.4. These samples were added to 2 µl anti-Aß mMAb-Sepharose Matrix and stirred for 2 h at room temperature. The samples were centrifuged for 5 min at 10000 g. The supernatants were discarded and the anti-Aß mMAb-Sepharose washed twice with 50 µl PBS, stirred for 1 min and centrifuged (5 min at 10000 g). The supernatants were discarded, and the Sepharose beads were now suspended in 50 µl 2 mM $NaH_2PO_4NaH2PO4$; 14 mM NaCl, pH7.4, followed by 1 min of stirring at room temperature and 5 min of centrifugation at 10000 g. In a next step, the anti-Aß mMAb-Sepharose beads were treated with 50 µl 50% $CH_3CN$; 0.2% TFA in water. After 10 min shaking at room temperature, samples were centrifuged 5 min at 10000 g. The supernatants were collected and transferred to 1.5 ml Eppendorf tubes. Samples were mixed with 50 µl water and evaporated in a Speed Vac concentrator. The pellet was redissolved in 4 µl 70% HCOOH, shaken for 10 min at room temperature and neutralized with 76 µl 1M Tris-solution and 720 µl 20 mM $NaH_2PO_4NaH2PO4$; 140 mM NaCl; 0.05% Tween 20; pH 7.4.

Samples for the Determination of Aß(1-40); (1-42) Monomer Forms in CSF:
a) Aß-content in CSF-samples without immunoprecipitation:
  158 µl CSF were diluted with 342 µl 20 mM $NaH_2PO_4$; 140 mM NaCl; 0.05% Tween 20; pH 7.4. This 1:3.16 dilution was taken for Sandwich ELISA's and taken into account during evaluation.
b) Aß-content in CSF-samples after immunoprecipitation: Samples from the above-mentioned procedure were taken for analysis.

Sandwich-ELISA Protocol Used for the Determination of Aß (1-40) in CSF

Reagent List:
1. F96 Cert. Maxisorp NUNC-Immuno Plate Cat.No.: 439454
2. Binding antibody
  Anti-Aß mAb clone 6E10; Signet Cat.No. 9320; conc.: 0.4 mg/ml Bradford (BioRad); store at −20° C.
3. Coupling-buffer
  100 mM sodiumhydrogencarbonate; pH9.6
4. Blocking Reagent for ELISA; Roche Diagnostics GmbH Cat.No.: 1112589
5. PBST-buffer
  20 mM $NaH_2PO_4NaH2PO4$; 140 mM NaCl; 0.05% Tween 20; pH7.4
6. Aß(1-40) Standard:
  Aß(1-40) solid powder; Bachem Cat.No.: H-1194; store at −20° C.
7. Primary antibody:
  anti-Aß (1-40) rabbit pAb; affinity purified; solution in PBS; conc.: 0.039 mg/ml; Signet Cat.No. 9130-005; store at −20° C.
8. Label reagent:
  anti-rabbit-POD conjugate; Fa. Jackson ImmunoResearch Cat.No.: 111-036-045;
9. Staining:
  TMB; Roche Diagnostics GmbH Cat.No.: 92817060; 42 mM in DMSO; 3% $H_2O_2$ in water; 100 mM sodium acetate pH 4.9
10. Stop Solution 2M Sulfonic Acid Protocols Used for Preparation of Reagents:
1. Binding antibody:
  anti-Aß mAb 6E10 (Signet Inc, Catalog #9320) is diluted to a final concentration of 0.7 microg/ml.
2. Blocking reagent:
  For preparation of the blocking stock solution the blocking reagent is dissolved in 100 ml $H_2O$ and stored at −20° C. in aliquots of 10 ml each. 3 ml of the blocking stock solution are diluted with 27 ml $H_2O$ for blocking one ELISA plate.
3. Aß(1-40) monomer form standard dilution:
  A) Aß(1-40) monomer Standard Stock: dissolve 0.5 mg Aß(1-40) in 250 µl 0.1% $NH_4OH$, conc.: 2 mg/ml; freshly prepared; use immediately.
  B) Add 5 µl Aß(1-40)-monomer standard stock solution to 995 µl PBST=10 µ/ml
  C) Add 5 µl, 10 µl/ml Aß(1-40)-monomer standard solution to 4995 µl PBST=10 ng/ml Standard Curve:

| No Final conc. | Stock | | PBST |
|---|---|---|---|
| 1<br>10000 pg/ml | 2 ml B | | 0 ml |
| 2<br>3160 pg/ml | 0.633 ml | (1) | 1.367 ml |
| 3<br>1000 pg/ml | 0.633 ml | (2) | 1.367 ml |
| 4<br>316 pg/ml | 0.633 ml | (3) | 1.367 ml |
| 5<br>100 pg/ml | 0.633 ml | (4) | 1.367 ml |
| 6<br>31.6 pg/ml | 0.633 ml | (5) | 1.367 ml |
| 7<br>10 pg/ml | 0.633 ml | (6) | 1.367 ml |
| 8<br>0.0 pg/ml | 0 ml | | 2 ml |

Samples:
  IP: immunoprecipitate Samples

| No dilution factor | sample | | PBST |
|---|---|---|---|
| 1<br>directly | 0.4 ml | IP | 0 ml |
| 2<br>1:5 | 0.1 ml | (1) | 0.4 ml |
| 3<br>1:25 | 0.1 ml | (2) | 0.4 ml |
| 4<br>1:125 | 0.1 ml | (3) | 0.4 ml |

4. Primary antibody:
  Dilute the concentrated anti-Aß (1-40) pAb in PBST buffer. The dilution factor is 1/200=0.2 µg/ml. Use immediately.
5. Secondary antibody:
  Lyophilized anti-rabbit-POD conjugate is dissolved in 0.5 ml $H_2O$ and mixed with 500 µl glycerol. The antibody concentrate is then stored at −20° C. in aliquots of 100 µl. The concentrate is diluted 1:10'000 in PBST buffer. The antibody solution is used immediately.
6. TMB solution:
  20 ml of 100 mN sodium acetate, pH 4.9, are mixed with 200 µl TMB solution and 29.5 µl of 3% hydrogen peroxide. This solution is used immediately.

Sample Plate Setup: (Note that all Standards and Samples are Run in Duplicate.)

|   | 1 | 2 | 3 | 4 | 5 | 6 | 7 | 8 | 9 | 10 | 11 | 12 |
|---|---|---|---|---|---|---|---|---|---|----|----|----|
| A | 10000 | 10000 | U1 | U1 | | | | | | | | |
| B | 3160 | 3160 | U2 | U2 | | | | | | | | |
| C | 1000 | 1000 | U3 | U3 | | | | | | | | |
| D | 316 | 316 | U4 | U4 | | | | | | | | |
| E | 100 | 100 | U5 | U5 | | | | | | | | |
| F | 31.6 | 31.6 | U6 | U6 | | | | | | | | |
| G | 10 | 10 | U7 | U7 | | | | | | | | |
| H | 0.0 | 0.0 | U8 | U8 | | | | | | | | |

U1-U# = Unknown samples

Procedure Used:
1. Apply 100 µl binding antibody solution per well and incubate overnight at 4° C.
2. Discard the antibody solution and wash the wells with 250 µl PBST-buffer for three times.
3. Add 260 µl block solution per well and incubate 2 h at room temperature.
4. Discard the block solution and wash the wells with 250 µl PBST-buffer for three times.
5. After preparation of standards and samples, apply 100 µl per well of standards and samples to the plate and incubate 2 h at room temperature and overnight at 4° C.
6. Discard the standard/sample solution and wash the wells with 250 µl PBST-buffer for three times.
7. Add 200 µl primary antibody solution per well and incubate 1.5 h at room temperature.
8. Discard the antibody solution and wash the wells with 250 µl PBST-buffer for three times.
9. Add 200 µl label solution per well and incubate 1 h at room temperature.
10. Discard the label solution and wash the wells with 250 µl PBST-buffer for three times.
11. Add 100 µl of TMB solution to each well and incubate at room temperature (5-15 min).
12. Observe colour development and apply 50 µl of the Stop solution per well.
13. Read at 450 nm.
14. Calculate results from standard curve.
15. Evaluation:
    If extinction from unknown samples is not in the linearity range of the calibration curve, repeat ELISA with appropriated sample dilution.

Sandwich-ELISA Protocol Used for the Determination of Aß (1-42) Monomer Form in CSF Reagent List:
1. F96 Cert. Maxisorp NUNC-Immuno Plate Cat.No.: 439454
2. Binding antibody
   Anti-Aß mAb clone 6E10; Signet Cat.No. 9320; conc.: 0.4 mg/ml Bradford (BioRad); store at −20° C.
3. Coating-Buffer
   100 mM sodiumhydrogencarbonate; pH9.6
4. Blocking Reagent for ELISA; Roche Diagnostics GmbH Cat.No.: 1112589
5. PBST-Buffer
   20 mM $NaH_2PO_4NaH_2PO_4$; 140 mM NaCl; 0.05% Tween 20; pH7.4
6. Aß(1-42) Standard:
   Aß(1-42) solid powder; Bachem Cat.No.: H-1368; store at −20° C.
7. Primary antibody:
   anti-Aß (1-42) rabbit pAb; affinity purified; biotinylated; solution in PBS with 50% glycerol; conc.: 0.25 mg/ml; Signet Cat.No. 9137-005; store at −20° C.
8. Label reagent:
   anti-rabbit-POD conjugate; Fa. Jackson ImmunoResearch Cat.No.: 111-036-045
9. Staining:
   TMB; Roche Diagnostics GmbH Cat. No.: 92817060; 42 mM in DMSO
   3% $H_2O_2$ in water
   100 mM sodium acetate, pH4.9
   Stop Solution: 2M Sulfonic Acid Method Used in Preparation of Reagents:
1. Binding antibody:
   Dilute anti-Aß mAb clone 6E10 1:400 in coating buffer.
2. Blocking reagent:
   Dissolve blocking reagent in 100 ml water to prepare the blocking stock solution and store aliquots of 10 ml at −20° C. Dilute 3 ml blocking stock solution with 27 ml water for each plate to block.
3. Aß(1-42) monomer form, standard dilution:
   Aß(1-42) Monomer Standard Stock: dissolve 0.5 mg Aß(1-42) in 250 µl 0.1% $NH_4OH$; conc.: 2 mg/ml; freshly prepared; use immediately.
   Add 5 µl Aß(1-42)-monomer standard stock solution to 995 µl PBST=10 µl/ml.
   Add 5 µl, 10 µg/ml Aß(1-42)-monomer standard solution to 4995 µl PBST=10 ng/ml.

Standard Curve:

| No Final conc. | Stock | | PBST |
|---|---|---|---|
| 1 10000 pg/ml | 2 ml B | | 0 ml |
| 2 3160 pg/ml | 0.633 ml | (1) | 1.367 ml |
| 3 1000 pg/ml | 0.633 ml | (2) | 1.367 ml |
| 4 316 pg/ml | 0.633 ml | (3) | 1.367 ml |
| 5 100 pg/ml | 0.633 ml | (4) | 1.367 ml |
| 6 31.6 pg/ml | 0.633 ml | (5) | 1.367 ml |
| 7 10 pg/ml | 0.633 ml | (6) | 1.367 ml |
| 8 0.0 pg/ml | 0 ml | | 2 ml |

Samples:

| IP: immunoprecipitate samples No dilution factor | sample | | PBST |
|---|---|---|---|
| 1 directly | 0.4 ml | IP | 0 ml |
| 2 1:5 | 0.1 ml | (1) | 0.4 ml |
| 3 1:25 | 0.1 ml | (2) | 0.4 ml |
| 4 1:125 | 0.1 ml | (3) | 0.4 ml |

Procedure Used:
1. Primary antibody:
   Dilute the concentrated anti-Aß(1-42) pAb in PBST buffer. The dilution factor is 1/1250=0.2 µg/ml. Use immediately.

2. Label Reagent:
   Reconstitute anti-rabbit-POD conjugate lyophilizate in 0.5 ml water. Add 500 µl glycerol and store aliquots of 100 µl at −20° C. for further use.
   Dilute the concentrated Label reagent in PBST-buffer. The dilution factor is 1/5000. Use immediately.
3. TMB solution:
   Mix 20 ml 100 mM sodium acetate pH4.9 with 200 µl of the TMB solution and 29.5 µl 3% Peroxide solution. Use immediately.

Sample Plate Setup: (Note that all Standards and Samples are Run in Duplicate.)

|   | 1 | 2 | 3 | 4 | 5 | 6 | 7 | 8 | 9 | 10 | 11 | 12 |
|---|---|---|---|---|---|---|---|---|---|----|----|----|
| A | 10000 | 10000 | U1 | U1 | | | | | | | | |
| B | 3160 | 3160 | U2 | U2 | | | | | | | | |
| C | 1000 | 1000 | U3 | U3 | | | | | | | | |
| D | 316 | 316 | U4 | U4 | | | | | | | | |
| E | 100 | 100 | U5 | U5 | | | | | | | | |
| F | 31.6 | 31.6 | U6 | U6 | | | | | | | | |
| G | 10 | 10 | U7 | U7 | | | | | | | | |
| H | 0.0 | 0.0 | U8 | U8 | | | | | | | | |

U1-U# = Unknown samples

Procedure Used:
1. Apply 1000 binding antibody solution per well and incubate overnight at 4° C.
2. Discard the antibody solution and wash the wells with 250 µl PBST-buffer for three times.
3. Add 260 µl block solution per well and incubate 2 h at room temperature.
4. Discard the block solution and wash the wells with 250 µl PBST-buffer for three times.
5. After preparation of standards and samples, apply 100 µl per well of standards and samples to the plate. Incubate 2 h at room temperature and overnight at 4° C.
6. Discard the standard/sample solution and wash the wells with 250 µl PBST-buffer for three times.
7. Add 200 µl primary antibody solution per well and incubate 1.5 h at room temperature.
8. Discard the antibody solution and wash the wells with 250 µl PBST-buffer for three times.
9. Add 200 µl label solution per well and incubate 1 h at room temperature.
10. Discard the label solution and wash the wells with 250 µl PBST-buffer for three times,
11. Add 1000 of TMB solution to each well and incubate at room temperature (5-15 min).
12. Observe color staining and apply 50 µl of the Stop Solution per well.
13. Read at 450 nm.
14. Calculate results from standard curve.
15 Evaluation:
   If extinction from unknown samples is not in the linearity range of the calibration curve, repeat ELISA with appropriate sample dilution.

Results:

|  | Aβ40 ELISA (Signet) | | Aβ42 ELISA (Signet) | | Aβ42/40 |
|---|---|---|---|---|---|
| MCI samples (n = 4) | Aβ(1-40) | SEM | Aβ(1-42) | SEM | |
| without IP | 11678.9 | 2879.4 | 1242.0 | 353.5 | 7.84% |
| 6E10 IP | 8282.4 | 2185.7 | 2035.1 | 280.9 | 17.35% |
| 8F5 IP | 8586.1 | 2396.8 | 2654.6 | 411.4 | 20.95% |

|  | Aβ40 ELISA (Signet) | | Aβ42 ELISA (Signet) | | Aβ42/40 |
|---|---|---|---|---|---|
| AD samples (n = 2) | Aβ (1-40) | SEM | Aβ(1-42) | SEM | |
| without IP | 7297.5 | 1464.5 | 843.0 | 157.5 | 10.95% |
| 6E10 IP | 5610.2 | 28.3 | 1453.0 | 14.5 | 20.57% |
| 8F5 IP | 4133.9 | 86.9 | 1670.2 | 12.3 | 28.78% |

Figure 3:
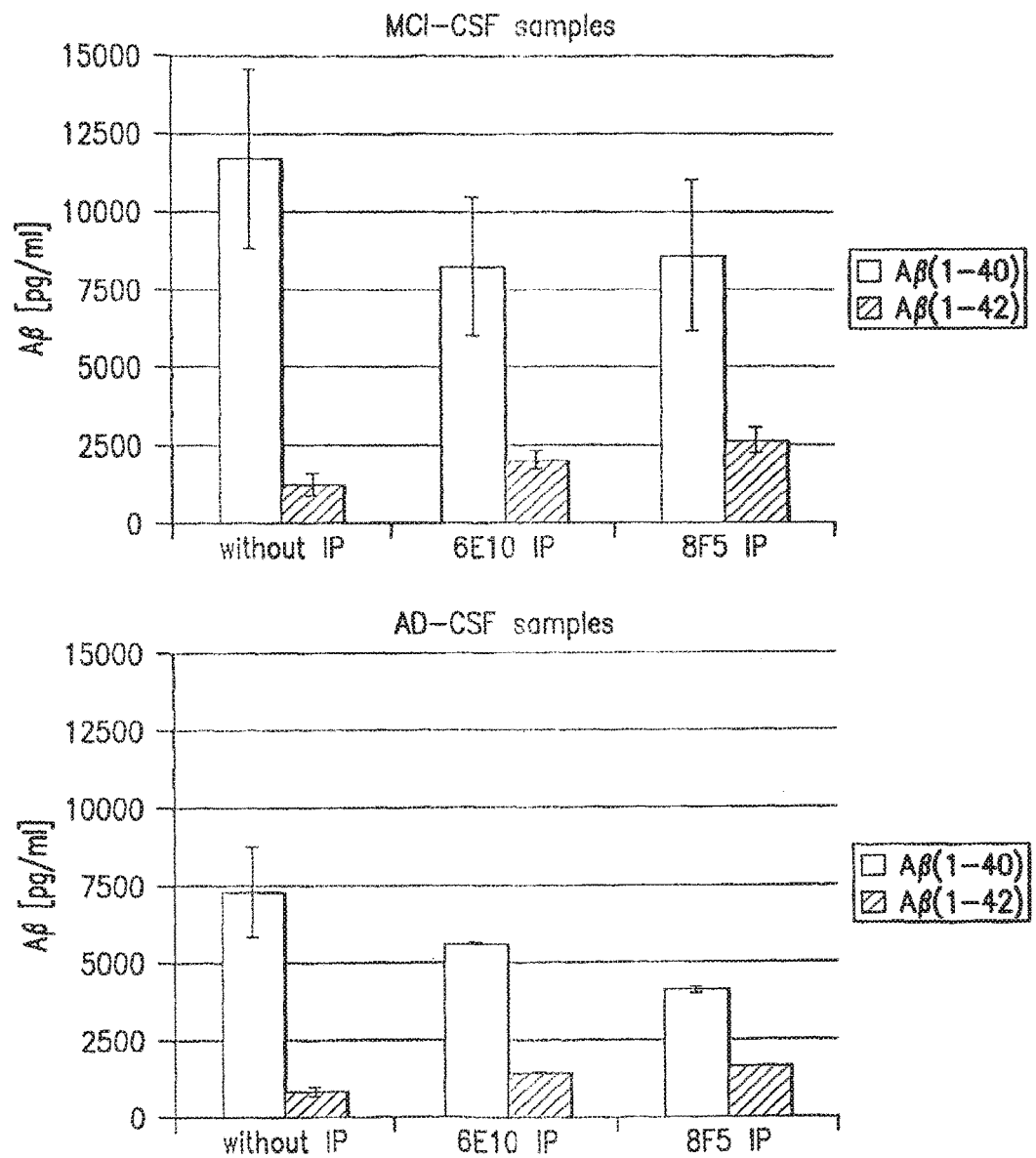
FIG. 3 illustrates Aß42 and Aß40 content in CSF samples from patients with Mild Cognitive Impairment (MCI, left) or Alzheimer's disease (AD, right). In both groups, it can be observed that 8F5 picks up a higher proportion of Aß(1-42) and less or an equal amount of Aß(1-40) if compared to a standard antibody 6E10 or compared to direct sample analysis with the same ELISAs.

The above results indicate the following:
a. A globulomer Preferential antibody like 8F5 (or 8C5), in comparison to a non-globulomer selective antibody like 6E10, binds preferentially to Aβ42 compared to Aβ40 independent from the disease state, This result is indicative of a successful treatment for Alzheimer's Disease because preferentially eliminating Aβ42 over Aβ40 is being followed as a concept in AD-treatment, e.g., by the use of R-flubiprofen, Flurizan which has demonstrated efficacy in AD treatment in a clinical trial published by Myriad Inc. This concept was published by S. Weggen et al. (J Biol Chem. (2003) 278(34):31831-7). The results are shown in FIG. 3.
b. A globulomer preferential antibody like 8F5 (or 8C5) binds to even more Aβ42 than Aβ40 in patients compared to healthy controls. This result is even more indicative of a successful treatment for Alzheimer's Disease because, as noted above, preferentially eliminating Aβ42 over Aβ40 is being followed as a concept in AD-treatment (e.g., by the use of non-steroidal anti-inflammatory drugs, like R-flubiprofen). (See FIG. 3.)

B) Endogenous Amyloid ß(1-42) and Amyloid ß(1-40) Levels in Human CSF after Immunoprecipitation with Globulomer Selective Anti-Aß Murine MAB 8F5 or 8C5 in Comparison with Globulomer Unselective Antibody 6E10:
b1) Immunoprecipitation (IP) with Dynabeads M-280 Sheep Anti-Mouse IgG
Abeta-Antibody Solutions
The following pure antibodies were obtained from hybridomas according to standard purification procedures:
   mMab 6E10; Fa.Signet Nr.: 9320; 1 mg/ml in PBS buffer
   mMab 8F5; 1.65 mg/ml in PBS buffer
   mMab 8C5; 1.44 mg/ml in PBS buffer
Dynabeads M-280 Sheep anti-Mouse IgG:
   Sheep anti-Mouse IgG (Invitrogen Inc., Cat. no.: 112.02) is covalently bound to magnetic beads (Dynabeads).
Activation of Dynabeads with monoclonal mouse antibodies
   The stock-suspension of dynabeads (Dynabeads M-280 Sheep anti-Mouse IgG, Invitrogen; Prod. No. 112.02) was shaken carefully to prevent foaming.
   1 mL was aseptically removed and transferred to a 1.5 mL reaction vial.
   The dynabeads were washed 3 times 5 min with 1 mL immunoprecipitation (IP)-wash buffer (IP-wash-buffer: PBS (20 mM $Na_2H_2PO_4$, 140 mM NaCl, pH 7.4), 0.1% (w/v) BSA). During the washing procedure, the supernatant was carefully removed while the dynabeads were immobilized at the side of the reaction vial with a magnetic separator stand (MSS).
   The washed dynabeads were incubated with 40 µg Abeta-antibody in 1 mL PBS, 0.1% (w/v) BSA.
   The activation was carried out by overnight incubation under shaking at 4° C.
   The activated dynabeads were washed 4 times 30 min (again using the MSS) with 1 mL IP-wash buffer (PBS (20 mM $NaH_2PO_4$, 140 mM NaCl, pH 7.4), 0.1% (w/v) BSA).

The activated dynabeads were resuspended with 1 mL PBS, 0.1% (w/v) BSA, 0.02 (w/v) % Na-Azide; vortexed and centrifuged briefly.

The antibody activated dynabeads were stored at 4° C. until further use.

CSF Sample Preparation:

400 µL CSF from an Alzheimer's disease patient were added to 4 µL Complete Protease Inhibitor Cocktail (Roche Inc. Cat. no.: 1697498, 1 tablet dissolved in 1 mL water) and 0.8 µL 500 mM PMSF dissolved in methanol. After 10 min., 1.6 mL 20 mM $NaH_2PO_4$, 140 mM NaCl, 0.05% Tween 20, pH 7.4 (PBST) was added.

Immunoprecipitation of Abeta Species from Human AD-CSF:

250 µL aliquot of the prepared CSF sample were added to 25 µL anti-Aß-Dynabeads suspension.

Immunoprecipitation occurred under stirring at 6° C. for 16 hours. Subsequent washing of the beads was performed 3 times 5 min. with 1 mL PBS/0.1% (w/v) BSA and finally once 3 min. with 1 mL 10 mM Tris/HCL pH 7.5 buffer. During the washing procedure, the supernatant was carefully removed while the dynabeads were immobilized at the side of the reaction vial with a magnetic separator stand (MSS).

The residual supernatant was thoroughly removed after the final washing step. The Abeta peptides and the corresponding antibody were removed from the Dynabeads by adding 25 µL sample buffer without β-Mercaptoethanol (0.36 M Bistris, 0.16 M Bicine, 1% SDS (w/v), 15% (w/v) sucrose, 0.004% (w/v) Bromphenolblue) to the Eppendorff tube and heating for 5 min at 95° C. in a heating block. After cooling to room temperature, the dynabeads were immobilized at the side of the reaction vial with a magnetic separator stand (MSS), and the supernatant was transferred to another Eppendorff tube (IP eluate).

Analysis of Abeta immunoprecipitates by urea-PAGE followed by Western Blot procedure:

The quantification of Aß-40 and Aß1-42 species was performed by a 8 M Urea Poly-Acrylamide-Gel-Electrophoresis system and subsequent Western Blot analysis according to the procedure first described by H. W. Klafki et al., Analytical Biochemistry 237, 24-29 (1996) and later also used by J. Wiltfang et al., J. of Neurochemistry 81, 481-496, 2002. There were only two minor changes made in the experimental procedure:

1) SDS concentration in the stacking gel was adjusted to 0.25% (w/v) instead of 0.1% (w/v).
2) For the Western blot the antibody 1E8 (Senetek Drug Delivery Technologies Inc. St. Louis, Mo., USA) was replaced by Anti-Human Amyloid β (N) (82E1) Mouse IgG mAb (IBL, Cat.no.: 10323)

15 µL IP eluate aliquots of the immunoprecipitated samples were loaded onto the 8 M Urea PAGE. Electrophoresis was performed at 100 V (15 min) and continued at 60 V. The electrophoresis was stopped when the running front of the blue sample loading dye was still 0.5 cm away from the end of the gel.

Western Blot Procedure:

Western blot analysis was performed in a Semi Dry Blotting chamber (BioRad Inc., 45 min at 75 mA) onto 7.5 cm×9 cm Nitrocellulose 0.45 µm (BioRad Inc.).

Blotting buffer: 6 g Tris; 28.1 g Glycin; 500 m L Methanol; adjust to 2.5 l with water.

The Nitrocellulose blot was boiled for 10 min in PBS at 100° C. The blot was saturated by treatment with 50 mL 5% (w/v) BSA in PBST for 1 hour at RT. After removal of the fluid phase, the following washing step was performed twice with: 50 mL TTBS (25 mM Tris/HCl; 150 mM NaCl Puffer; 0.05% Tween 20; pH 7.5) for 10 min at RT and subsequently with 50 mL TBS (25 mM Tris/HCl; 150 mM NaCl buffer; pH 7.5) for 10 min at RT.

For further development, the final washing buffer was discarded from the blot and 15 mL antibody I solution (0.2 µg/mL 82E1=1:500 in 3% (w/v) skimmed milk powder (Lasana Inc.), in 15 mL TBS) were added for 20 hours at 6° C. Removal of buffer was followed by the three wash steps as described above. The blot was incubated with Antibody solution II (1:10000 dilution of anti-Mouse-POD in 15 mL 3% (w/v) skimmed milk powder in 15 mL TBS) for 1 hour at RT. Removal of buffer was followed by the three wash steps as described above.

After removal of the last washing buffer, 2 mL Super Signal West Femto Maximum Sensitivity Substrate Enhancer and 2 mL Peroxide Solution was mixed. The freshly prepared solution was poured onto the blot which was preincubated in the dark for 5 min. Chemiluminescence was recorded using a VersaDoc Imaging system (BioRad).

Imaging Parameters:

exposure time 180 sec.

Picture records after 30 sec., 60 sec., 120 sec. and 180 sec.

The results were obtained from the picture with 180 sec. exposure time.

|  | Aβ40 urea-PAGE [pg/ml] | Aβ42 urea-PAGE [pg/ml] | Ratio Aβ42/Aβ40 + 42 x100% |
|---|---|---|---|
| 6E10 IP | 4389 | 202 | 4.4% |
| 8F5 IP | 1260 | 112 | 8.1% |
| 8C5 IP | 1202 | 211 | 14.9% |

The above results indicate that a globulomer preferential antibody like 8F5 or 8C5, in comparison to a non-globulomer selective antibody like 6E10, binds to more Aβ42 than Aβ40 in human CSF. This result is indicative of a successful treatment for Alzheimer's Disease because, as noted above, preferentially eliminating Aβ42 over Aβ40 is being following as a concept in AD-treatment (e.g., by the use of R-flubiprofen (see above)).

Example V

8F5 Improves Novel Object Recognition in APP Transgenic Mice

In order to test a positive effect on cognition by neutralizing internal Aß(1-42) globulomer epitope with antibody 8F5, a passive immunization experiment with APP transgenic mice was performed in which the mice were tested for their ability to remember objects they have investigated before. After some time, delay between first and second encounter of objects, APP transgenic mice are not able to recognize the already investigated object. This experiment is based on the natural curiosity of the animals, and a significant lack of interest in the already investigated object demonstrates recognition of the object.

Example V.1: Increased Recognition Index by Monoclonal Antibody 8F5

Animals:

Female mice of a single transgenic mouse model of Alzheimer's Disease in FVB×C57B1 background (APP/L, ReMYND, Leuven, Belgium) and negative litter mates as wild type controls in FVB×C57B1 background with an age of 3 months were used. All mice were genotyped by polymerase chain reaction (PCR) at the age of 3 weeks and received a unique identity number, once the PCR results were known and were double checked by a second PCR before the onset of the study. All mice were randomized and age-matched, i.e., they were given a random number by computer and allocated randomly to a treatment. Animals were caged by treatment group 18 days before the onset of the study in order to allow them to familiarize to the new cage context. Mice had free access to pre-filtered and sterile water (UV-lamp) and standard mouse chow. The food was stored under dry and cool conditions in a well-ventilated storage room. The amount of water and food was checked daily, supplied when necessary and refreshed twice a week. Mice were housed under a reversed day-night rhythm: 14 hours light/10 hours darkness starting at 7 p.m. in standard metal cages type RVS T2 (area of 540 cm2). The cages are equipped with solid floors and a layer of bedding litter. The number of mice per cage was limited in accordance with legislation on animal welfare. Five days before the onset of the behavior test, mice were replaced in macrolon Type 2 cages and transported to the laboratory in order to adapt to the laboratory environment in preparation for the behavior test.

Treatment (Passive Immunization):

Three individual experiments were performed in which the mice (at least 9 per group) received intraperitoneal injections (500 µg in 240 µL/mouse) at days 1, 8 and 15. Mice were treated with monoclonal antibodies 6G1, 8F5 and other non-disclosed antibodies, all dissolved in phosphate-buffered saline, or with 320 µL phosphate-buffered saline.

Novel Object Recognition Test:

The novel object recognition test was performed on the day of the third treatment. The protocol used followed the method as described by Dewachter et al. (Journal of Neuroscience, 2002, 22(9):3445-3453). Mice were familiarized for one hour to a Plexiglas open-field box (52×52×40 cm) with black vertical walls and a translucent floor, dimly illuminated by a lamp placed underneath the box. The next day, the animals were placed in the same box and submitted to a 10 minute acquisition trial. During this trial, mice were placed individually in the open field in the presence of 2 identical objects A (orange barrel or green cube, similar size of ±4 cm), and the duration (time$_{AA}$) and the frequency (Freq$_{AA}$) exploring object A (when the animals snout was directed towards the object at a distance of <1 cm and the mice were actively sniffing in the direction of the object) was recorded by a computerized system (Ethovision, Noldus information Technology, Wageningen, Netherlands). During a 10 minute retention trial (second trial) performed 2.5 hours later, a novel object (object B, green cube or orange barrel) was placed together with the familiar object (object A) into the open field (Freq$_A$ and Freq$_B$ and Time$_A$ and Time$_B$, respectively). The recognition index (RI), defined as the ratio of the duration in which the novel object was explored over the duration in which both objects were explored [Time$_B$/(Time$_A$+Time$_B$)×100], was used to measure non-spatial memory. The duration and frequency that object A was explored during the acquisition trial (Time$_{AA}$ and Freq$_{AA}$) was used to measure curiosity.

Figure 4:
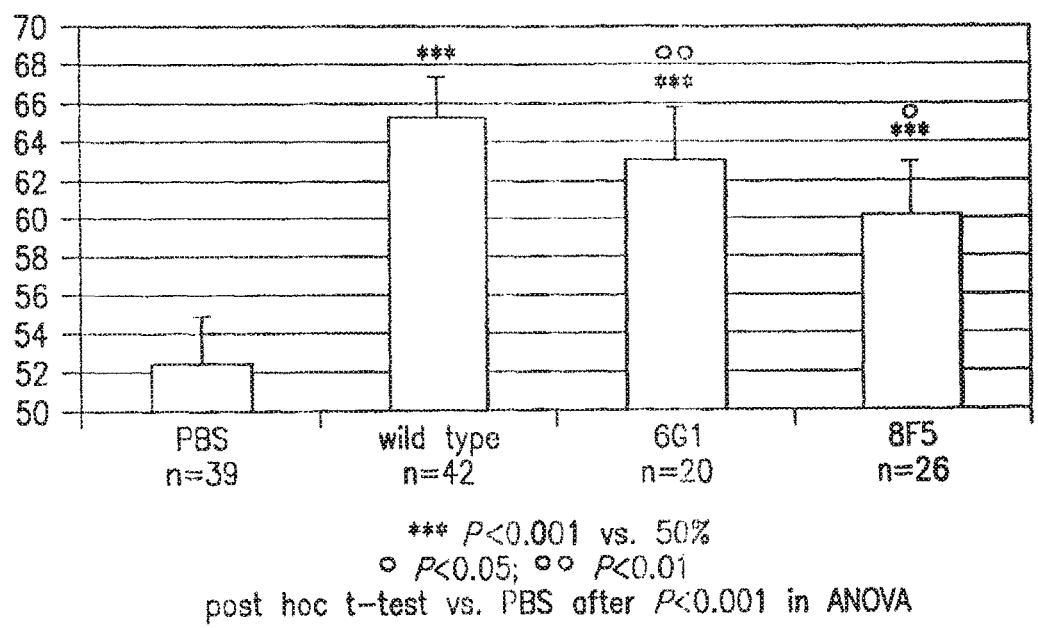
FIG. 4 illustrates novel object recognition index as time spent with unknown versus familiar object in three groups of APP transgenic mice (i.e., 6G1, 8F5, PBS) and one group of non-transgenic litter mates (wild type). The animals (number given below columns) were immunized with monoclonal antibodies 6G1 or 8F5 or treated with vehicle (i.e., phosphate-buffered saline; PBS, and wild type) by once weekly intraperitoneal injection for three weeks. On the day of the last injection, a novel object recognition task was performed. The difference between PBS and wild type groups indicated a cognitive deficit of APP transgenic mice in this paradigm. PBS-injected mice performed at chance level (i.e., not significantly different from 50) while all other mice showed object recognition (t-test; stars). When the performance of antibody-treated APP transgenic mice was compared with control groups, a significant difference was found versus PBS-treated but not versus wild-type mice (ANOVA with post-hoc t-test; circles) indicating that antibody treatment reversed the cognitive deficit in these APP transgenic mice.

Analysis of data was done by combining APP transgenic mice that received monoclonal antibodies 6G1 or 8F5 or phosphate-buffered saline, and non-transgenic littermates that received phosphate-buffered saline, from all three studies (FIG. 4). Mice that do not distinguish between an old object and a novel object have a recognition index of 50. Mice that recognize the old object will preferably explore the novel object and hence the recognition index becomes >50. Mice that exclusively explore the novel object have a recognition index of 100. The mean recognition index per group was compared against chance level, i.e., 50, by t-test. The mean recognition index of all groups was also compared by ANOVA followed by a post-hoc t-test. The difference between PBS and wild type groups indicated a cognitive deficit of APP transgenic mice in this paradigm. PBS-injected mice performed at chance level (i.e., not significantly different from 50) while all other mice showed object recognition (FIG. 4: stars). When the performance of antibody-treated APP transgenic mice was compared with control groups, a significant difference was found versus PBS-treated but not versus wild-type mice (FIG. 4: circles) indicating that treatment with antibody 8F5 reversed the cognitive deficit in these APP transgenic mice.

Example VI

In Situ Analysis of the Specific Reaction of Antibodies 8F5 and 8C5 to Fibrillar Amyloid Beta Peptide in the Form of Amyloid Plaques and Amyloid in Meningeal Vessels in Old APP Transgenic Mice and Alzheimer's Disease Patients Antibodies 8F5 and 8C5 show reduced staining to fibrillar Aβ peptide deposits suggesting that their therapeutic effect is mediated by binding to soluble globulomeric forms rather than fibrillar deposited forms of Aβ peptide. Since antibody binding to fibrillar Aβ peptide can lead to fast dissolution of aggregates and a subsequent increase of soluble Aβ concentration, which in turn is thought to be neurotoxic and could lead to microhemorrhages, an antibody therapy that effects the soluble globulomer rather than the monomer is preferred.

Methods:

For these experiments, several brain material samples were used: cortical tissue from 2 AD patients (RZ16 and RZ 55) and cortical tissue from 19 month old Tg2576 mice (APPSWE #001349, Taconic, Hudson, N.Y., USA) or 12 month old APP/L mice (ReMYND, Leuven, Belgium).

The mice overexpress human APP with a familial Alzheimer's disease mutation and form β-amyloid deposits in the brain parenchyma at about 11 months of age and β-amyloid deposits in larger cerebral vessels at about 18 months of age. The animals were deeply anaesthetized and transcardially perfused with 0.1 M phosphate-buffered saline (PBS) to flush the blood. Then, the brain was removed from the cranium and divided longitudinally. One hemisphere of the brain was shock-frozen and the other fixated by immersion into 4% paraformaldehyde. The immersion-fixated hemisphere was cryoprotected by soaking in 30% sucrose in PBS and mounted on a freezing microtome. The entire forebrain was cut into 40 µm transverse sections which were collected in PBS and used for the subsequent staining procedure. The neocortex samples from Alzheimer's disease patients were obtained from Brain-Net, Munich, Germany as frozen tissue, immersion-fixated in 4% paraformaldehyde during thawing, and subsequently treated like the mouse tissue.

Individual sections were stained with Congo Red using the following protocol:

Material:

Amyloid dye Congo Red kit (Sigma-Aldrich; HT-60), consisting of alcoholic NaCl solution, NaOH solution and Congo Red solution staining cuvettes
microscope slides SuperfrostPlus and coverslips
Ethanol, Xylol, embedding medium Reagents:
  NaOH diluted 1:100 with NaCl solution yields alkaline saline
  alkaline saline diluted 1:100 with Congo Red solution yields alkaline Congo Red solution (prepare no more than 15 min before use, filtrate)
  mount sections on slide and allow them to dry
  incubate slide in staining cuvette, first for 30-40 minutes in alkaline saline, then for 30-40 minutes in alkaline Congo Red solution
  rinse three times with fresh ethanol and embed over xylol Staining was first photographed using a Zeiss Axioplan microscope (Zeiss, Jena, Germany) and evaluated qualitatively. Red color indicated amyloid deposits both in the form of plaques and in larger meningeal vessels. Later on, evaluation of antibody staining focused on these structures.

Staining was performed by incubating the sections with a solution containing 0.07-0.7 µg/ml of the respective antibody in accordance with the following protocol:

Materials:
  TBST washing solution (Tris Buffered Saline with Tween 20; 10× concentrate; DakoCytomation 53306, DAKO, Hamburg, Germany) 1:10 in Aqua bidest.)
  0.3% $H_2O_2$ in methanol
  donkey serum (Serotec Dusseldorf, Germany), 5% in TBST, as blocking serum
  monoclonal mouse-anti-globulomer antibodies diluted at given concentrations in TBST
  secondary antibody: biotinylated donkey-anti-mouse antibody (Jackson Immuno/Dianova, Hamburg, Germany; 715-065-150; diluted 1:500 in TBST)
  StreptABComplex (DakoCytomation K 0377, DAKO, Hamburg, Germany)
  Peroxidase Substrate Kit diaminobenzidine (=DAB; SK-4100; Vector Laboratories, Burlingame, Calif., USA)
  SuperFrost Plus microscope slides and coverslips
  xylol free embedding medium (Medite, Burgdorf, Germany; X-tra Kitt)

Procedure:
  transfer floating sections into ice-cold 0.3% $H_2O_2$ and incubate for 30 min
  wash for 5 min in TBST buffer
  incubate with donkey serum/TBST for 20 minutes
  incubate with primary antibody for 24 hours at room temperature
  wash in TBST buffer for 5 minutes
  incubate with blocking serum for 20 minutes
  wash in TBST buffer for 5 minutes
  incubate with secondary antibody for 60 minutes at ambient temperature
  wash in TBST buffer for 5 minutes
  incubate with StreptABComplex for 60 minutes at ambient temperature
  wash in TBST buffer for 5 minutes
  incubate with DAB for 20 minutes
  mount the section on slides, air-dry slides, dehydrate slides with alcohol and embed slides Besides visual inspection of sections under the microscope, amyloid staining was additionally quantified by optically excising 10 randomly selected plaques from the histological images using the ImagePro 5.0 image analysis system and determining their average greyscale value. Optical density values (were calculated from the greyscale values by subtracting the mean background density of the stained material from the density of amyloid plaques (0% —no plaque staining above surrounding background, 100% —no transmission/maximal staining). The differences between antibodies 6E10/4G8 and 6G1, 8C5 and 8F5, respectively, were tested for statistical significance with ANOVA.

Figure 7A:
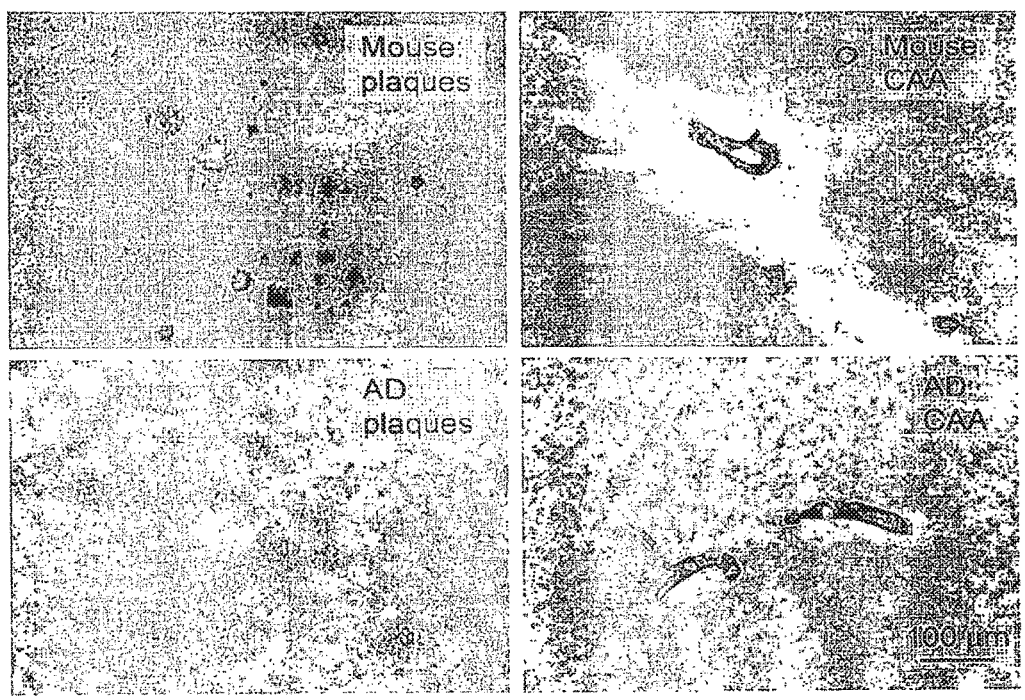
FIGS. 7A-7H show the binding of antibodies, at different concentrations, to transversal sections of the neocortices of Alzheimer's disease (AD) patients or old APP transgenic mice. In particular.
Figure 7B:
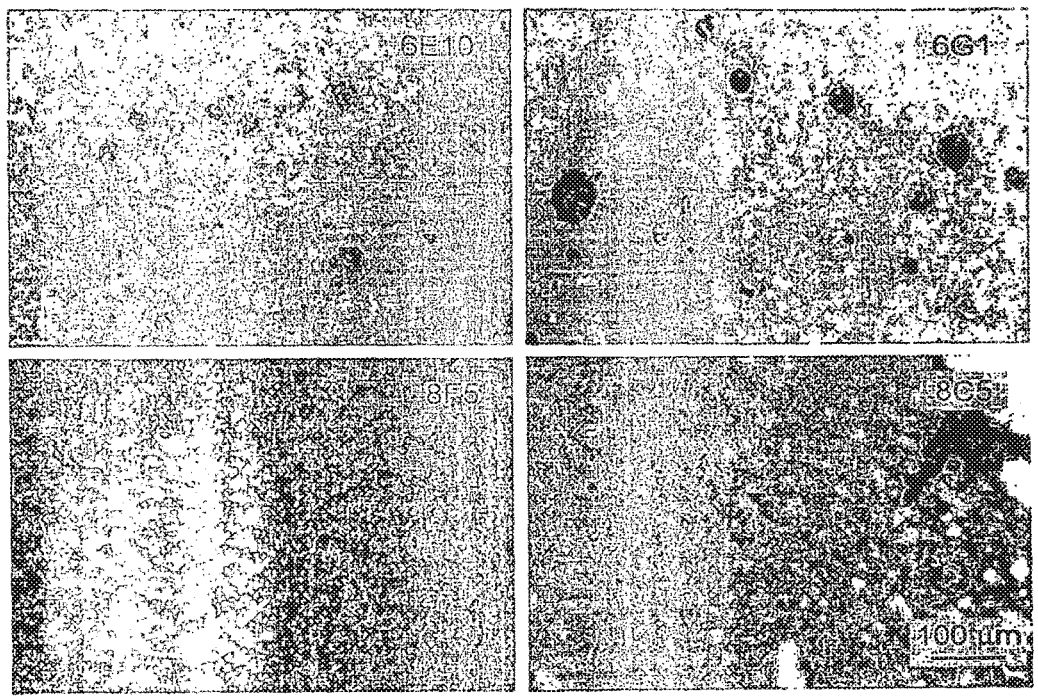
Figure 7C:
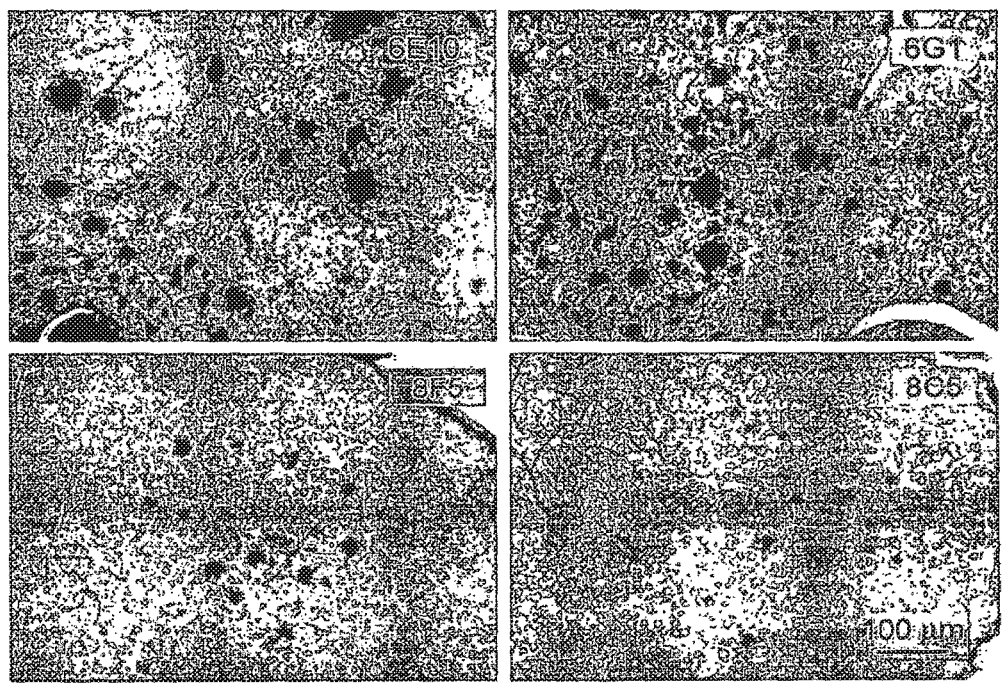
Figure 7D:
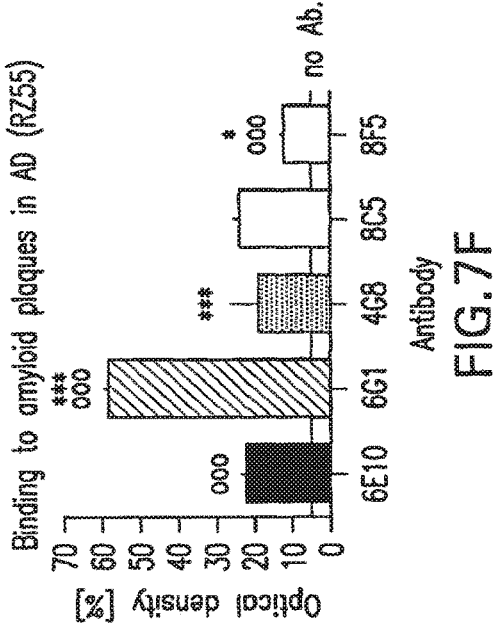
Figure 7F:
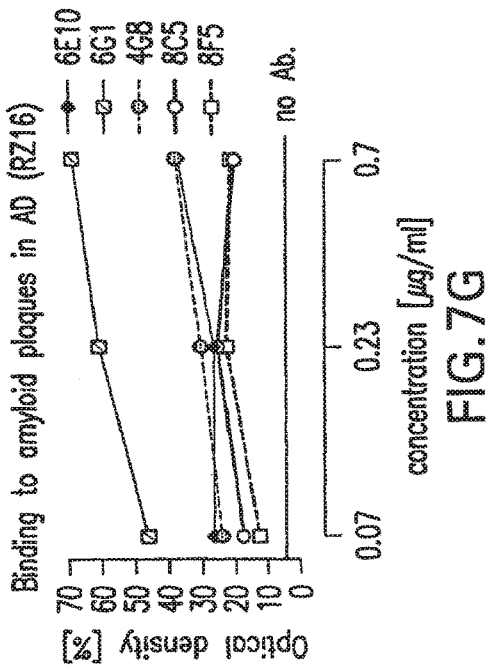
Figure 7E:
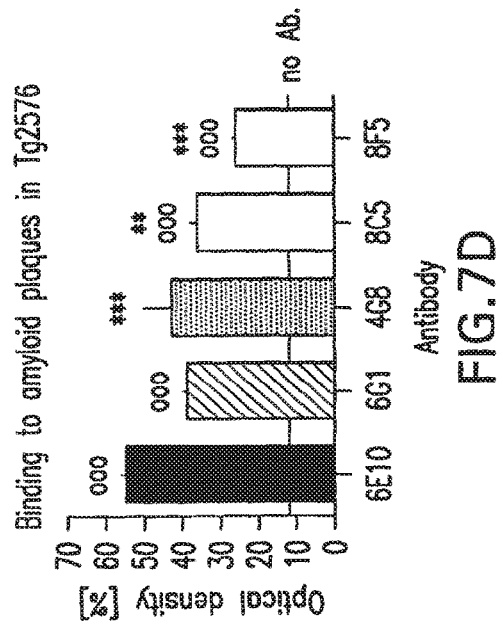
Figure 7G:
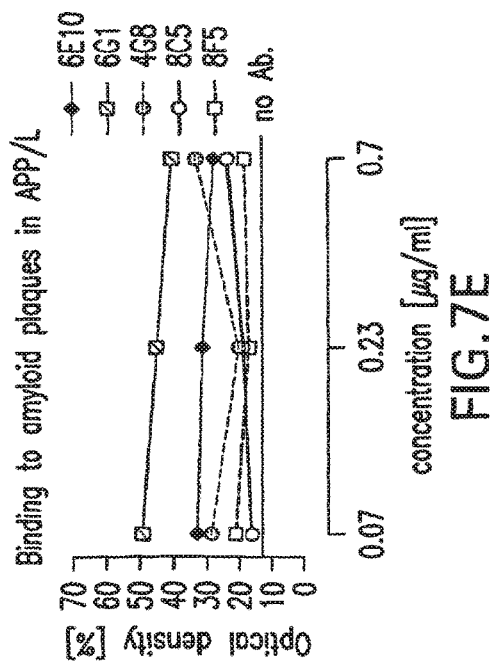
Figure 7H:
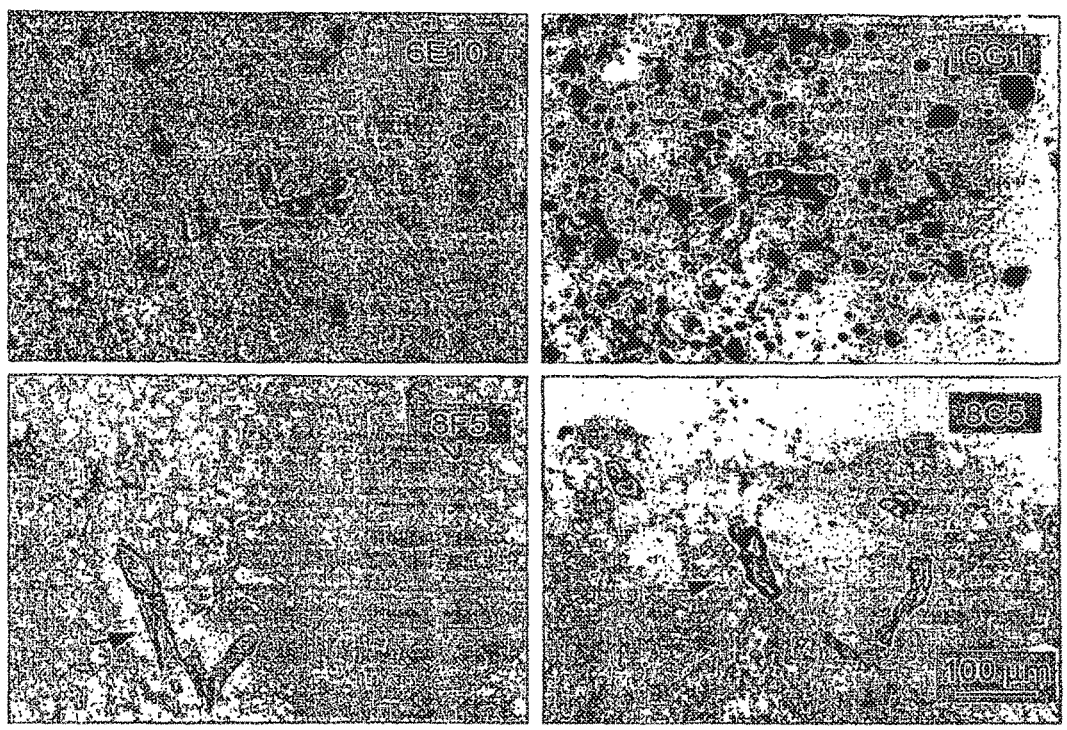

Results:
All antibody-stained material, described proved to be congophilic amyloid deposits (FIG. 7A). The globulomer-preferring antibodies 8F5 and 805 stained parenchymal and meningeal corigophilic deposits of AP peptide significantly less than the antibodies 6G1 and 6E10 (FIGS. 7B-7C, 7H). Quantitative analysis of parenchymal amyloid plaque staining revealed binding of all antibodies to plaques (statistically significant density above control), but binding of antibody 8-5 and 8C5 was significantly lower than binding of the reference antibody 6E10 (raised to N-terminal sequence of Aβ) and equal or lower than reference antibody 4G8 (raised to N-terminal sequence of Aβ (FIGS. 7D-7G).

Antibodies 8F5 and 8C5 bind less to amyloid deposits than antibodies which recognize Aβ monomer or part of the Aβ sequence. Treatment with antibodies binding to fibrillar Aβ peptide can lead to fast dissolution of amyloid plaques in brain tissue and a subsequent increase of soluble Aβ concentration, which in turn is thought to be neurotoxic and could lead to microhemorrhages, and/or a fast dissolution of vascular amyloid, which also could lead to microhemorrhages. Therefore, an antibody therapy that affects the soluble globulomer rather than the monomer is preferred.

What is claimed is:

1. A method of treating Alzheimer's Disease in a patient in need of said treatment comprising administering an isolated antibody that binds with greater specificity to an amyloid beta (Aβ) protein globulomer than to an amyloid beta protein monomer in an amount sufficient to effect said treatment, wherein the antibody comprises
   a) a light chain variable region CDR 1 comprising the amino acid sequence of SEQ ID NO:8;
   b) a light chain variable region CDR 2 comprising the amino acid sequence of SEQ ID NO:9;
   c) a light chain variable region CDR 3 comprising the amino acid sequence of SEQ ID NO:10;
   d) a heavy chain variable region CDR 1 comprising the amino acid sequence of SEQ ID NO:5;
   e) a heavy chain variable region CDR 2 comprising the amino acid sequence of SEQ ID NO:6; and
   f) a heavy chain variable region CDR 3 comprising the amino acid sequence of SEQ ID NO: 7.

2. The method of claim 1 wherein said isolated antibody is administered via a route selected from the group consisting of intramuscular administration, intravenous administration and subcutaneous administration.

3. The method of claim 1, wherein the antibody is humanized.

4. A method of treating Alzheimer's Disease in a patient in need of said treatment comprising the step of administering a composition comprising an antibody with greater specificity to an amyloid beta (Aβ) protein globulomer than to an amyloid beta protein monomer to said patient in an amount sufficient to effect said treatment wherein the antibody comprises
    a) a light chain variable region CDR 1 comprising the amino acid sequence of SEQ ID NO:8;
    b) a light chain variable region CDR 2 comprising the amino acid sequence of SEQ ID NO:9;
    c) a light chain variable region CDR 3 comprising the amino acid sequence of SEQ ID NO:10;
    d) a heavy chain variable region CDR 1 comprising the amino acid sequence of SEQ ID NO:5;
    e) a heavy chain variable region CDR 2 comprising the amino acid sequence of SEQ ID NO:6; and
    f) a heavy chain variable region CDR 3 comprising the amino acid sequence of SEQ ID NO: 7.

5. The method of claim 4, wherein the antibody is humanized.

6. A method of treating Alzheimer's Disease in a patient in need of said treatment comprising the step of administering a vaccine comprising an isolated antibody with greater specificity to an amyloid beta (Aβ) protein globulomer than to an amyloid beta protein monomer and a pharmaceutically acceptable adjuvant to said patient in an amount sufficient to effect said treatment, wherein the antibody comprises
    a) a light chain variable region CDR 1 comprising the amino acid sequence of SEQ ID NO:8;
    b) a light chain variable region CDR 2 comprising the amino acid sequence of SEQ ID NO:9;
    c) a light chain variable region CDR 3 comprising the amino acid sequence of SEQ ID NO:10;
    d) a heavy chain variable region CDR 1 comprising the amino acid sequence of SEQ ID NO:5;
    e) a heavy chain variable region CDR 2 comprising the amino acid sequence of SEQ ID NO:6; and
    f) a heavy chain variable region CDR 3 comprising the amino acid sequence of SEQ ID NO: 7.

7. The method of claim 6, wherein the antibody is humanized.

8. A method of treating Alzheimer's Disease in a patient in need of said treatment comprising administering an isolated antibody that binds with greater specificity to an amyloid beta (Aβ) protein globulomer than to an amyloid beta protein monomer in an amount sufficient to effect said treatment, wherein the antibody comprises the complementarity determining regions of SEQ ID NO:3 and SEQ ID NO:4, wherein the antibody is humanized.

9. A method of treating Alzheimer's Disease in a patient in need of said treatment comprising the step of administering a composition comprising an antibody with greater specificity to an amyloid beta (Aβ) protein globulomer than to an amyloid beta protein monomer to said patient in an amount sufficient to effect said treatment wherein the antibody comprises the complementarity determining regions of SEQ ID NO:3 and SEQ ID NO:4, wherein the antibody is humanized.

10. A method of treating Alzheimer's Disease in a patient in need of said treatment comprising the step of administering a vaccine comprising an isolated antibody with greater specificity to an amyloid beta (Aβ) protein globulomer than to an amyloid beta protein monomer and a pharmaceutically acceptable adjuvant to said patient in an amount sufficient to effect said treatment, wherein the antibody comprises the complementarity determining regions of SEQ ID NO:3 and SEQ ID NO:4, wherein the antibody is humanized.

11. A method of treating Alzheimer's Disease in a patient in need of said treatment comprising administering an isolated antibody that binds with greater specificity to an amyloid beta (Aβ) protein globulomer than to an amyloid beta protein monomer in an amount sufficient to effect said treatment, wherein
    the light chain variable region of the antibody comprises the amino acid sequence of RSSQSLVYSNGDTYLH (SEQ ID NO: 8); the amino acid sequence of KVSNRFS (SEQ ID NO: 9); and the amino acid sequence of SQSTHVPWT (SEQ ID NO: 10); and
    the heavy chain variable region of the antibody comprises the amino acid sequence of GFTFSSYGMS (SEQ ID NO: 24); the amino acid sequence of SINSNGGSTYYPDSVKG (SEQ ID NO: 6); and the amino acid sequence of GDY (SEQ ID NO: 25).

12. The method of claim 11, wherein the antibody is humanized.

13. A method of treating Alzheimer's Disease in a patient in need of said treatment comprising the step of administering a composition comprising an antibody with greater specificity to an amyloid beta (Aβ) protein globulomer than to an amyloid beta protein monomer to said patient in an amount sufficient to effect said treatment wherein
    the light chain variable region of the antibody comprises the amino acid sequence of RSSQSLVYSNGDTYLH (SEQ ID NO: 8); the amino acid sequence of KVSNRFS (SEQ ID NO: 9); and the amino acid sequence of SQSTHVPWT (SEQ ID NO: 10); and
    the heavy chain variable region of the antibody comprises the amino acid sequence of GFTFSSYGMS (SEQ ID NO: 24); the amino acid sequence of SINSNGGSTYYPDSVKG (SEQ ID NO: 6); and the amino acid sequence of GDY (SEQ ID NO: 25).

14. The method of claim 13, wherein the antibody is humanized.

15. A method of treating Alzheimer's Disease in a patient in need of said treatment comprising the step of administering a vaccine comprising an isolated antibody with greater specificity to an amyloid beta (Aβ) protein globulomer than to an amyloid beta protein monomer and a pharmaceutically acceptable adjuvant to said patient in an amount sufficient to effect said treatment, wherein
    the light chain variable region of the antibody comprises the amino acid sequence of RSSQSLVYSNGDTYLH (SEQ ID NO: 8); the amino acid sequence of KVSNRFS (SEQ ID NO: 9); and the amino acid sequence of SQSTHVPWT (SEQ ID NO: 10); and
    the heavy chain variable region of the antibody comprises the amino acid sequence of GFTFSSYGMS (SEQ ID NO: 24); the amino acid sequence of SINSNGGSTYYPDSVKG (SEQ ID NO: 6); and the amino acid sequence of GDY (SEQ ID NO: 25).

16. The method of claim 15, wherein the antibody is humanized.

\* \* \* \* \*

SEQUENCE LISTING

<160> NUMBER OF SEQ ID NOS: 25

<210> SEQ ID NO 1
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaggtgcagc tggtggagtc tgggggaggc ttagtgcagc ctggagggtc cctgaaactc      60
tcctgtgcag cctctggatt cactttcagt agctatggca tgtcttgggt tcgccagact     120

```
ccagacaaga ggctggaatt ggtcgcaagc atcaatagta atggtggtag cacctattat    180
ccagacagtg tgaagggccg attcaccatc tccagagaca tgccaagaa caccctgtac     240 ctgcaaatga gcagtctgaa gtctgaggac acagccatgt attactgtgc aagtggtgac    300
tactggggcc aaggctccac tctcacagtc tcctca                              336
```

```
<210> SEQ ID NO 2
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gatgttgtga tgacccaaac tccactctcc ctgcctgtca gtcttggaga tcaagcctcc    60
atctcttgca gatctagtca gagccttgta tatagtaatg agacaccta tttacattgg    120 tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttcct    300
tggacgttcg gtggaggcac caagctagaa atcaaacgg                           339
```

```
<210> SEQ ID NO 3
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Ser Gly Asp Tyr Trp Gly Gln Gly Ser Thr Leu Thr Val Ser Ser
            100                 105                 110
```

```
<210> SEQ ID NO 4
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Tyr Ser
            20                  25                  30
```

```
Asn Gly Asp Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Trp Thr Phe Gly Gly Gly Thr Lys Leu Glu Ile Lys
            100                 105                 110

Arg

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Tyr Gly Met Ser
 1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ile Asn Ser Asn Gly Gly Ser Thr Tyr Tyr Pro Asp Ser Val Lys
 1               5                  10                  15

Gly

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Gly Asp Tyr
 1

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ser Ser Gln Ser Leu Val Tyr Ser Asn Gly Asp Thr Tyr Leu His
 1               5                  10                  15

<210> SEQ ID NO 9
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Val Ser Asn Arg Phe Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Gln Ser Thr His Val Pro Trp Thr
1               5

<210> SEQ ID NO 11
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaggtgcagt tggtggagtc tgggggaggc ttagtgcagc ctggagggtc cctgaaactc      60
tcctgtacag cctctggatt cactttcagt agctatggca tgtcttgggt tcgccagact     120
ccagacaaga ggctggagtt ggtcgcaagt attaaaaata tggtggtag cacctattat     180 ccagacagtt tgaagggccg attcaccatc tccagagaca atgccaagaa caccctgtac     240
ctgcaaatga gcagtctgaa gtctgaggac acagccatgt attattgtgc aagtggggat     300
tactggggcc aaggcaccac tctcacagtc tcctca                              336

<210> SEQ ID NO 12
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gatgttgtga tgacccaaac tccactctcc ctgcctgtca gtcttggaga tcaagcctcc      60
atctcttgca gatctagtca gagccttgta cacagtaatg agacaccttt tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggaatt tatttctgct ctcagagtat acatgttccg     300
tggacgttcg gtggaggcac caagctggaa atcaaacgg                           339

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 13

Ser Tyr Gly Met Ser
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Ile Lys Asn Asn Gly Gly Ser Thr Tyr Tyr Pro Asp Ser Leu Lys
1               5                   10                  15

Gly

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Gly Asp Tyr
1

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Ser Gln Ser Leu Val His Ser Asn Gly Asp Thr Phe Leu His
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Val Ser Asn Arg Phe Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Gln Ser Ile His Val Pro Trp Thr
1               5
```

<210> SEQ ID NO 19
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Glu Val Gln Leu Val Glu Ser Gly Gly Gly Leu Val Gln Pro Gly Gly
1               5                   10                  15

Ser Leu Lys Leu Ser Cys Thr Ala Ser Gly Phe Thr Phe Ser Ser Tyr
            20                  25                  30

Gly Met Ser Trp Val Arg Gln Thr Pro Asp Lys Arg Leu Glu Leu Val
        35                  40                  45

Ala Ser Ile Lys Asn Asn Gly Gly Ser Thr Tyr Tyr Pro Asp Ser Leu
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Ser Gly Asp Tyr Trp Gly Gln Gly Thr Thr Leu Thr Val Ser Ser
            100                 105                 110
```

<210> SEQ ID NO 20
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asp Thr Phe Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Ile His Val Pro Trp Thr Phe Gly Gly Gly Thr Lys Leu Glu Ile Lys
            100                 105                 110

Arg
```

<210> SEQ ID NO 21
<211> LENGTH: 42
<212> TYPE: PRT
<213> ORGANISM: Homo sapiens

<400> SEQUENCE: 21

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30
```

```
Gly Leu Met Val Gly Gly Val Val Ile Ala
        35                  40

<210> SEQ ID NO 22
<211> LENGTH: 40
<212> TYPE: PRT
<213> ORGANISM: Homo sapiens

<400> SEQUENCE: 22

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Phe Thr Phe Ser Ser Tyr Gly Met Ser
1               5                   10

<210> SEQ ID NO 25
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Asp Tyr
1
```